United States Patent
Slomczynska et al.

(10) Patent No.: US 10,548,313 B2
(45) Date of Patent: *Feb. 4, 2020

(54) ACETYL-COA CARBOXYLASE MODULATORS

(71) Applicant: Monsanto Technology LLC, St. Louis, MO (US)

(72) Inventors: Urszula Slomczynska, Ballwin, MO (US); Matthew W. Dimmic, Wildwood, MO (US); William P. Haakenson, Jr., St. Louis, MO (US); Jennifer L. Bennett, St. Louis, MO (US); Barry J. Shortt, New Melle, MO (US); Christina M. Taylor, Chesterfield, MO (US); Deryck Jeremy Williams, University City, MO (US); Martin Slater, Sudbury (GB)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/820,644

(22) Filed: Nov. 22, 2017

(65) Prior Publication Data

US 2018/0070589 A1 Mar. 15, 2018

Related U.S. Application Data

(63) Continuation of application No. 14/896,605, filed as application No. PCT/US2014/042265 on Jun. 13, 2014, now Pat. No. 9,844,218.

(60) Provisional application No. 61/834,598, filed on Jun. 13, 2013.

(51) Int. Cl.
| | | |
|---|---|---|
| *A01N 37/22* | (2006.01) | |
| *A01N 43/40* | (2006.01) | |
| *C07D 409/14* | (2006.01) | |
| *C07D 405/14* | (2006.01) | |
| *C07D 413/14* | (2006.01) | |
| *C07D 215/54* | (2006.01) | |
| *C07D 217/26* | (2006.01) | |
| *C07D 401/04* | (2006.01) | |
| *C07D 405/04* | (2006.01) | |
| *C07D 409/04* | (2006.01) | |
| *C07D 417/14* | (2006.01) | |
| *C07D 471/04* | (2006.01) | |
| *A01N 25/00* | (2006.01) | |
| *A01N 35/10* | (2006.01) | |
| *A01N 37/10* | (2006.01) | |
| *A01N 37/28* | (2006.01) | |
| *A01N 43/42* | (2006.01) | |
| *A01N 43/84* | (2006.01) | |
| *A01N 43/90* | (2006.01) | |
| *A01N 57/20* | (2006.01) | |

(52) U.S. Cl.
CPC ............ *A01N 37/22* (2013.01); *A01N 25/00* (2013.01); *A01N 35/10* (2013.01); *A01N 37/10* (2013.01); *A01N 37/28* (2013.01); *A01N 43/40* (2013.01); *A01N 43/42* (2013.01); *A01N 43/84* (2013.01); *A01N 43/90* (2013.01); *A01N 57/20* (2013.01); *C07D 215/54* (2013.01); *C07D 217/26* (2013.01); *C07D 401/04* (2013.01); *C07D 405/04* (2013.01); *C07D 405/14* (2013.01); *C07D 409/04* (2013.01); *C07D 409/14* (2013.01); *C07D 413/14* (2013.01); *C07D 417/14* (2013.01); *C07D 471/04* (2013.01)

(58) Field of Classification Search
CPC ........ A01N 37/22; A01N 37/10; A01N 37/28; A01N 43/42; A01N 43/84; A01N 43/90; A01N 35/10; A01N 57/20; A01N 43/40; A01N 25/00; C07D 213/85; C07D 471/04; C07D 417/14; C07D 409/04; C07D 405/04; C07D 401/04; C07D 217/26; C07D 215/54; C07D 413/14; C07D 405/14; C07D 409/14

See application file for complete search history.

(56) References Cited

U.S. PATENT DOCUMENTS

| | | |
|---|---|---|
| 4,465,017 A | 8/1984 | Simmons |
| 4,759,945 A | 7/1988 | Nemecek et al. |
| 5,080,925 A | 1/1992 | Kouno |
| 5,107,787 A | 4/1992 | Kouno |
| 5,240,940 A | 8/1993 | Arnold et al. |
| 5,389,399 A | 2/1995 | Bazin et al. |
| 5,554,445 A | 9/1996 | Struszczyk et al. |

(Continued)

FOREIGN PATENT DOCUMENTS

| | | | |
|---|---|---|---|
| WO | 9834115 A1 | 8/1998 | |
| WO | 9952892 A1 | 10/1999 | |

(Continued)

OTHER PUBLICATIONS

Ling, L.L., Identification and Characterization of Inhibitors of Bacterial Enoyl-Acyl Carrier Protein Reductase, May 2004, Antimicrobial Agents and Chemotherapy, vol. 48, No. 5, pp. 1541-1547. (Year: 2004).*

(Continued)

*Primary Examiner* — John Pak
*Assistant Examiner* — Andriae M Holt
(74) *Attorney, Agent, or Firm* — Stinson LLP; Lawrence M. Lavin, Jr.

(57) ABSTRACT

Provided herein are compounds that exhibit activity as acetyl-CoA carboxylase modulators (e.g., inhibitors) and are useful, for example, in methods for the control of fungal pathogens in plants.

20 Claims, 1 Drawing Sheet

(56) References Cited

U.S. PATENT DOCUMENTS

| | | | |
|---|---|---|---|
| 5,891,246 | A | 4/1999 | Lund |
| 5,918,413 | A | 7/1999 | Otani et al. |
| 9,844,218 | B2 | 12/2017 | Slomczynska et al. |
| 2006/0128702 | A1 | 6/2006 | Pal et al. |
| 2007/0015799 | A1 | 1/2007 | Ashton et al. |
| 2007/0027190 | A1 | 2/2007 | Moir |
| 2008/0200461 | A1 | 8/2008 | Anderson et al. |
| 2008/0255150 | A1 | 10/2008 | Luker |
| 2008/0300303 | A1 | 12/2008 | Huse et al. |
| 2009/0048311 | A1 | 2/2009 | Williams et al. |
| 2009/0306133 | A1 | 12/2009 | Blomberg et al. |
| 2011/0028320 | A1 | 2/2011 | Slomczynska et al. |
| 2011/0046110 | A1 | 2/2011 | Vu et al. |
| 2011/0275645 | A1 | 11/2011 | Desai et al. |
| 2012/0252801 | A1 | 10/2012 | Bardiot et al. |
| 2013/0058980 | A1 | 3/2013 | Desai et al. |

FOREIGN PATENT DOCUMENTS

| | | |
|---|---|---|
| WO | 2004064837 A1 | 8/2004 |
| WO | 2004101506 A1 | 11/2004 |
| WO | 2007124544 A1 | 8/2007 |
| WO | 2007124545 A1 | 11/2007 |
| WO | 2012030887 A1 | 3/2012 |
| WO | 2013037735 A1 | 3/2013 |

OTHER PUBLICATIONS

Fedotov, K.V., et al., "Cyclization of Substituted (2-Pyridylthio)Phenylacetic Acids and Chromaticity of Mesoionic Thiazolo[3,2-a]Pyridinium-3-Olates," 2011, Chem Hetero Comp, 45/5:622-630.

Pakdaman, B.S., et al., "An in vitro Study on the Possibility of Rapeseed White Stem Rot Disease Control Through the Application of Prevalent Herbicides and Trichoderma Species," 2006, Pak J Biol Sci, 10:7-12.

Pakdaman, B.S., et al., "Cellular Membranes as the Sites for the Antifungal Activity of the Herbicide Sethoxydim," 2007, Pak J Biol Sci 10:2480-2484.

Reichenbach, H., et al. "Discovery of a new antifungal mechanism of action, soraphen: an almost-success story," 1994, In JH Walsdorff, ed, Scientific Annual Report. Gesellschaft für Biotechnologische Forschung mbH, Braunschweig, Germany, pp. 5-22.

Rodinovskaya, L.A., et al., "One-Pot Synthesis of Diverse 4-Di(tri)Fluoromethyl-3-Cyanopyridine-2(1H)Thiones and Their Utilities in the Cascade Synthesis of Annulated Heterocycles," 2008, J Comb Chem, 10:313-322.

Tong, L., et al., "Acetyl-Coenzyme A Carboxylases: Versatile Targets for Drug Discovery," 2006, J Cell Biochem, 99:1476-1488.

Biotechnology: Pharmaceutical Aspects, "Prodrugs: Challenges and Rewards Part 2", V. Stella et al. Editors, vol. V (2007) pp. 3-33, 41 pages.

"Current Methods in Medicinal Chemistry and Biological Physics" vol. 2 (2008) pp. 187-214.

PUBCHEM CID-1035635 Create Date: Jul. 10, 2005 (Jul. 10, 2005) p. 1.

PUBCHEM CID 16325401 Deposit Date Jul. 30, 2007 (Jul. 30, 2007) pp. 1-4.

PUBCHEM Substance Summary for CID 17391770 Deposit Date Nov. 13, 2007 (Nov. 13, 2007), pp. 1-4.

International Search Report issued in PCT/US2014/42265, dated Oct. 10, 2014, 6 pages.

* cited by examiner

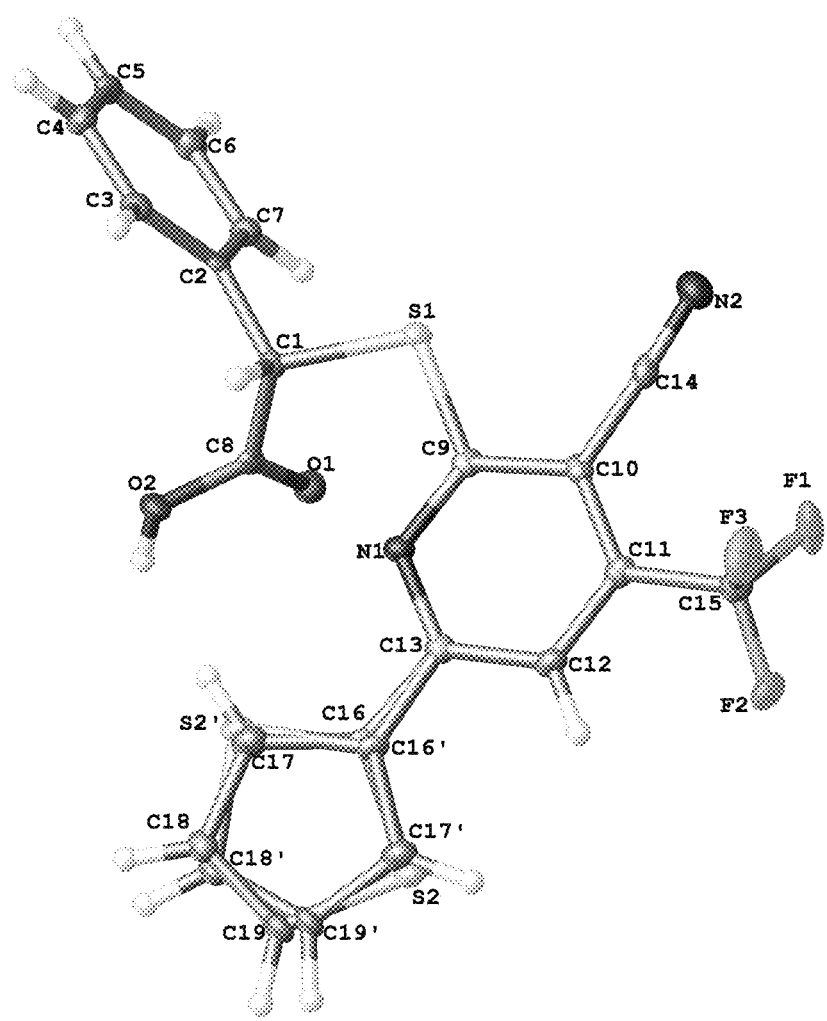

ACETYL-COA CARBOXYLASE MODULATORS

REFERENCE TO RELATED APPLICATIONS

The present application is a continuation of U.S. Ser. No. 14/896,605, filed Dec. 7, 2015, which is the 371 National Stage Application of International PCT Application No. PCT/US2014/042265, filed Jun. 13, 2014, which claims the benefit of U.S. Provisional Application No. 61/834,598, filed Jun. 13, 2013, the entire contents of which are incorporated herein by reference

FIELD

Provided herein are compounds that exhibit activity as acetyl-CoA carboxylase modulators (e.g., inhibitors) and are useful, for example, in methods for the control of fungal pathogens and diseases caused by fungal pathogens in plants.

BACKGROUND

Acetyl-CoA carboxylase ("ACCase") is an essential catalyst for the rate-limiting step of fatty acid biosynthesis in both eukaryotes and prokaryotes. Phytopathogenic fungi can infect crop plants either in the field or after harvesting, resulting in considerable economic losses to farmers and producers worldwide. In addition to the agricultural impact, when food and feed contaminated with fungi or the toxins they produce are ingested by humans or livestock, a number of debilitating diseases or death can occur. Approximately 10,000 species of fungi are known to damage crops and affect quality and yield. Crop rotation, breeding of resistant cultivars, the application of agrochemicals and combinations of these strategies is commonly employed to stem the spread of fungal pathogens and the diseases they cause. Additional chemistry and methods of using such as a modulator for ACCase or to control fungi are important for, among other things, protection in agriculture.

For example, the rapid onset of resistance to chemical fungicides has often lowered the efficacy of some chemical fungicides. This threat, as well as emergence and spread of additional fungal diseases, accentuates the need for new means of fungal control.

SUMMARY

In one aspect, therefore, the present disclosure is directed to a compound of Formula I or a salt thereof,

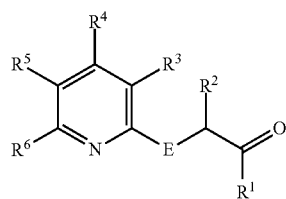

Formula I wherein $R^1$ is selected from the group consisting of OH, and $N(R^7R^8)$, wherein $R^7$ and $R^8$ are independently selected from the group consisting of hydrogen, OH, and $CH_3$;

$R^2$ is selected from the group consisting of alkyl, cycloalkyl, heterocycloalkyl, aryl, and heteroaryl, each of which may be optionally substituted with one or more substituents selected from the group consisting of halogen, $CH_3$, $OCH_3$, $CF_3$, $OCF_3$, and CN;

$R^3$ is selected from the group consisting of hydrogen, CN, ethynyl, $CH_2N(R^9R^{10})$, and $C(O)N(R^9R^{10})$, wherein $R^9$ and $R^{10}$ are each independently selected from the group consisting of hydrogen and alkyl;

$R^4$ is selected from the group consisting of haloalkyl, aryl, arylalkyl, heteroaryl, and heteroarylalkyl, each of which may be optionally independently substituted with one or more substituents selected from the group consisting of halogen, alkyl, alkoxy, haloalkyl, haloalkoxy, alkenyl, hydroxyalkyl, hydroxyl, $N(R^9R^{10})$, $NR^{11}C(O)R^{12}$, and $O(CO)R^{13}$, wherein $R^9$ and $R^{10}$ are independently selected from the group consisting of hydrogen and alkyl, $R^{11}$ is selected from the group consisting of hydrogen and alkyl, $R^{12}$ is alkyl, and $R^{13}$ is alkyl;

$R^5$ is selected from the group consisting of hydrogen and alkyl; or $R^4$ and $R^5$ together form a fused cycloalkyl or heterocycloalkyl ring having from 5 to 6 ring atoms selected from the group consisting of carbon, nitrogen, and oxygen;

$R^6$ is selected from the group consisting of alkyl, haloalkyl, aryl, arylalkyl, heteroaryl, and heteroarylalkyl, each of which may be optionally independently substituted with one or more substituents selected from the group consisting of halogen, alkyl, alkoxy, haloalkyl, and haloalkoxy; or $R^5$ and $R^6$ together form a fused cycloalkyl or heterocycloalkyl ring having from 5 to 6 ring atoms selected from the group consisting of carbon, nitrogen, and oxygen; and E is selected from the group consisting of S, O, N(H), $N(CH_3)$, and $CH_2$.

In another aspect, the present disclosure is directed to a compound of Formula II or a salt thereof,

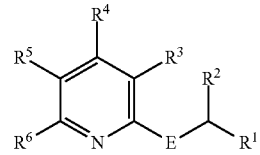

Formula II wherein $R^1$ is selected from the group consisting of a prodrug of a carboxylic acid and a carboxylic acid isostere;

$R^2$ is selected from the group consisting of alkyl, cycloalkyl, heterocycloalkyl, aryl and heteroaryl, each of which may be optionally independently substituted with one or more substituents selected from the group consisting of halogen, $CH_3$, $OCH_3$, $CF_3$, $OCF_3$, and CN;

$R^3$ is selected from the group consisting of hydrogen, CN, ethynyl, $CH_2N(R^9R^{10})$, and $C(O)N(R^9R^{10})$, wherein $R^9$ and $R^{10}$ are each independently selected from the group consisting of hydrogen and alkyl;

$R^4$ is selected from the group consisting of haloalkyl, aryl, arylalkyl, heteroaryl, and heteroarylalkyl, each of which may be optionally independently substituted with one or more substituents selected from the group consisting of halogen, alkyl, alkoxy, haloalkyl, haloalkoxy, alkenyl, hydroxyalkyl, hydroxyl, $N(R^9R^{10})$, $NR^{11}C(O)R^{12}$ and $O(CO)R^{13}$, wherein $R^9$ and $R^{10}$ are independently selected from the group consisting of hydrogen and alkyl, $R^{11}$ is selected from the group consisting of hydrogen and alkyl, $R^{12}$ is alkyl, and $R^{13}$ is alkyl;

$R^5$ is selected from the group consisting of hydrogen and alkyl; or $R^4$ and $R^5$ together form a fused cycloalkyl or heterocycloalkyl ring having from 5 to 6 ring atoms selected from the group consisting of carbon, nitrogen, and oxygen;

$R^6$ is selected from the group consisting of alkyl, haloalkyl, aryl, arylalkyl, heteroaryl, and heteroarylalkyl, each of which may be optionally independently substituted with one or more substitutents selected from the group consisting of halogen, alkyl, alkoxy, haloalkyl, and haloalkoxy; or $R^5$ and $R^6$ together form a fused cycloalkyl or heterocycloalkyl ring having from 5 to 6 ring atoms selected from the group consisting of carbon, nitrogen, and oxygen; and E is selected from the group consisting of S, O, N(H), N(CH$_3$), and CH$_2$.

Another aspect of the present disclosure is directed to a compound selected from the group consisting of: 2-((4-(4-chlorophenyl)-3-cyano-6-(thiophen-2-yl)pyridin-2-yl)thio)-2-phenylacetic acid, or a salt thereof, 2-((3-cyano-6-(thiophen-2-yl)-4-(trifluoromethyl)pyridin-2-yl)thio)-2-phenylacetic acid, or a salt thereof, 2-((3-cyano-4,6-di(thiophen-2-yl)pyridin-2-yl)thio)-2-phenylacetic acid, or a salt thereof, 2-((3-cyano-4-phenyl-6-(thiophen-2-yl)pyridin-2-yl)thio)-2-phenylacetic acid, or a salt thereof, 2-((3-cyano-4-(4-methoxyphenyl)-6-phenylpyridin-2-yl)thio)-2-phenylacetic acid, or a salt thereof, 2-((3-cyano-6-methyl-4-(thiophen-2-yl)-5,6,7,8-tetrahydro-1,6-naphthyridin-2-yl)thio)-2-phenylacetic acid, or a salt thereof, 2-((4-cyano-1-(thiophen-2-yl)-5,6,7,8-tetrahydroisoquinolin-3-yl)thio)-2-phenylacetic acid, or a salt thereof, 2-((3-cyano-6-(2,4-dimethoxyphenyl)-4-(trifluoromethyl)pyridin-2-yl)thio)-2-phenylacetic acid, or a salt thereof, 2-((3-cyano-6-(3,4-dimethoxyphenyl)-4-(trifluoromethyl)pyridin-2-yl)thio)-2-phenylacetic acid, or a salt thereof, 2-((6-(4-bromophenyl)-3-cyano-4-(trifluoromethyl)pyridin-2-yl)thio)-2-phenylacetic acid, or a salt thereof, 2-((3-cyano-6-(furan-2-yl)-4-(trifluoromethyl)pyridin-2-yl)thio)-2-phenylacetic acid, or a salt thereof, 2-((3-cyano-4,6-diphenylpyridin-2-yl)thio)-2-phenylacetic acid, or a salt thereof, 2-((3-cyano-4-(thiophen-2-yl)-5,6,7,8-tetrahydroquinolin-2-yl)thio)-2-phenylacetic acid, or a salt thereof, 2-((3-cyano-4-(4-methoxyphenyl)-6-(thiophen-2-yl)pyridin-2-yl)thio)-2-phenylacetic acid, or a salt thereof, 2-((4-cyano-1-ethyl-5,6,7,8-tetrahydroisoquinolin-3-yl)thio)-2-phenylacetic acid, or a salt thereof, 2-((3-cyano-6-methyl-4-(trifluoromethyl)pyridin-2-yl)thio)-2-phenylacetic acid, or a salt thereof, 2-((3-cyano-4-phenyl-5,6,7,8-tetrahydroquinolin-2-yl)thio)-2-phenylacetic acid or a salt thereof, 2-((4-(4-chlorophenyl)-3-cyano-5,6,7,8-tetrahydronaphthalen-2-yl)thio)-2-phenylacetic acid, or a salt thereof, 2-((4-(4-methoxyphenyl)-6-(thiophen-2-yl)pyridin-2-yl)thio)-2-phenylacetic acid, or a salt thereof, 2-((3-cyano-6-(furan-2-yl)-4-(4-methoxyphenyl)pyridin-2-yl)thio)-2-phenylacetic acid, or a salt thereof, 2-((3-cyano-6-(thiophen-2-yl)-4-(p-tolyl)pyridin-2-yl)thio)-2-phenylacetic acid, or a salt thereof, 2-((3-cyano-4-(4-fluorophenyl)-6-(thiophen-2-yl)pyridin-2-yl)thio)-2-phenylacetic acid, or a salt thereof, 2-((4-(4-bromophenyl)-3-cyano-6-(thiophen-2-yl)pyridin-2-yl)thio)-2-phenylacetic acid, or a salt thereof, 2-((3-cyano-6-(furan-2-yl)-4-(thiophen-2-yl)pyridin-2-yl)thio)-2-phenylacetic acid, or a salt thereof, 2-((3-cyano-4,6-di(furan-2-yl)pyridin-2-yl)thio)-2-phenylacetic acid, or a salt thereof, 2-((3-cyano-4-(4-methoxyphenyl)-5,6,7,8-tetrahydroquinolin-2-yl)thio)-2-phenylacetic acid, or a salt thereof, 2-((3-cyano-4-(thiophen-2-yl)-5,6,7,8-tetrahydroquinolin-2-yl)oxy)-2-phenylacetic acid, or a salt thereof, 2-((3-cyano-4-(4-methoxyphenyl)-6-(1-oxidothiophen-2-yl)pyridin-2-yl)oxy)-2-phenylacetic acid, or a salt thereof, 2-((3-cyano-4-(4-methoxyphenyl)-6-(thiophen-2-yl)pyridin-2-yl)thio)butanoic acid, or a salt thereof, 2-((3-cyano-4-(4-methoxyphenyl)-6-(pyrimidin-2-yl)pyridin-2-yl)thio)-2-phenylacetic acid, or a salt thereof, 2-((3-cyano-6-(3-methoxy-1-methyl-1H-pyrrol-2-yl)-4-(4-methoxyphenyl)pyridin-2-yl)thio)-2-phenylacetic acid, or a salt thereof, 2-((3-cyano-4-(furan-2-yl)-6-(thiophen-2-yl)pyridin-2-yl)thio)-2-phenylacetic acid, or a salt thereof, 2-((3-cyano-4-(thiophen-2-yl)-5,6,7,8-tetrahydroquinolin-2-yl)thio)-2-phenylacetamide, or a salt thereof, 2-((3-cyano-4-(4-methoxyphenyl)-6-(thiophen-2-yl)pyridin-2-yl)thio)-2-phenylacetamide, or a salt thereof, 2-((3-cyano-4-(4-methoxyphenyl)-6-(thiophen-2-yl)pyridin-2-yl)thio)-N-hydroxy-2-phenylacetamide, or a salt thereof, 4-(4-methoxyphenyl)-2-((phenyl(1H-tetrazol-5-yl)methyl)thio)-6-(thiophen-2-yl)nicotinonitrile, or a salt thereof, (((3-cyano-4-(4-methoxyphenyl)-6-(thiophen-2-yl)pyridin-2-yl)thio)(phenyl)methyl)phosphonic acid, or a salt thereof, (((3-cyano-4-(4-methoxyphenyl)-6-(thiophen-2-yl)pyridin-2-yl)thio)(phenyl)methyl)phosphinic acid, or a salt thereof, (((3-cyano-4-(4-methoxyphenyl)-6-(thiophen-2-yl)pyridin-2-yl)thio)(phenyl)methanesulfonic acid, or a salt thereof, (((3-cyano-4-(4-methoxyphenyl)-6-(thiophen-2-yl)pyridin-2-yl)thio)(phenyl)methanesulfonamide, or a salt thereof, 2-((3-cyano-4-(4-methoxyphenyl)-6-(thiophen-2-yl)pyridin-2-yl)thio)-N-(methylsulfonyl)-2-phenylacetamide, or a salt thereof, 2-(((2,4-dioxothiazolidin-5-yl)(phenyl)methyl)thio)-4-(4-methoxyphenyl)-6-(thiophen-2-yl)nicotinonitrile, or a salt thereof, 2-(((2,4-dioxooxazolidin-5-yl)(phenyl)methyl)thio)-4-(4-methoxyphenyl)-6-(thiophen-2-yl)nicotinonitrile, or a salt thereof, 4-(4-methoxyphenyl)-2-(((5-oxo-4,5-dihydro-1,2,4-oxadiazol-3-yl)(phenyl)methyl)thio)-6-(thiophen-2-yl)nicotinonitrile, or a salt thereof, 2-((2-hydroxy-1-phenylethyl)thio)-4-(4-methoxyphenyl)-6-(thiophen-2-yl)nicotinonitrile, or a salt thereof, 2-((2-hydroxy-1-phenylethyl)thio)-4-(thiophen-2-yl)-5,6,7,8-tetrahydroquinoline-3-carbonitrile, or a salt thereof, methyl 2-((3-cyano-6-(thiophen-2-yl)-4-(trifluoromethyl)pyridin-2-yl)thio)-2-phenylacetate, or a salt thereof, and 4-(furan-2-yl)-2-((2-hydroxy-1-phenylethyl)thio)-6-(thiophen-2-yl)nicotinonitrile, or a salt thereof.

Another aspect of the present disclosure is generally related to a method of controlling fungal pathogens comprising administering to a plant, a seed or soil a composition comprising an effective amount of a compound as described herein.

Another aspect of the present disclosure is generally related to a method for modulating ACCase in a biological organism comprising administering to the biological organism a composition comprising an effective amount of a compound as described herein.

Another aspect of the present disclosure is generally related to a composition comprising a compound as described herein.

Another aspect of the present disclosure is generally related to a seed comprising a coating comprising a compound or a composition as described herein.

Other objects and features will be in part apparent and in part pointed out hereinafter.

BRIEF DESCRIPTION OF THE DRAWINGS

FIG. 1 depicts the ORTEP plots (50% probability ellipsoids) for a compound of Formula Ia-ii-e2 using single crystal X-ray diffraction.

DETAILED DESCRIPTION

Described herein are compounds that exhibit activity as acetyl-CoA carboxylase modulators. The compounds described herein may be used, for example, in the preparation of compositions and in accordance with methods for control of fungal pathogens, as set forth in detail below.

For example, in one embodiment, the compound is a compound of Formula I or a salt thereof,

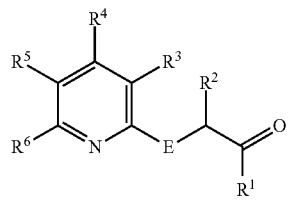

Formula I wherein $R^1$ is selected from the group consisting of OH and $N(R^7R^8)$, wherein $R^7$ and $R^8$ are independently selected from the group consisting of hydrogen, OH, and $CH_3$;

$R^2$ is selected from the group consisting of alkyl, cycloalkyl, heterocycloalkyl, aryl, and heteroaryl, each of which may be optionally substituted with one or more substituents selected from the group consisting of halogen, $CH_3$, $OCH_3$, $CF_3$, $OCF_3$, and CN;

$R^3$ is selected from the group consisting of hydrogen, CN, ethynyl, $CH_2N(R^9R^{10})$, and $C(O)N(R^9R^{10})$, wherein $R^9$ and $R^{10}$ are each independently selected from the group consisting of hydrogen and alkyl;

$R^4$ is selected from the group consisting of haloalkyl, aryl, arylalkyl, heteroaryl, and heteroarylalkyl, each of which may be optionally independently substituted with one or more substitutents selected from the group consisting of halogen, alkyl, alkoxy, haloalkyl, haloalkoxy, alkenyl, hydroxyalkyl, hydroxyl, $N(R^9R^{10})$, $NR^{11}C(O)R^{12}$, and $O(CO)R^{13}$, wherein $R^9$ and $R^{10}$ are independently selected from the group consisting of hydrogen and alkyl, $R^{11}$ is selected from the group consisting of hydrogen and alkyl, $R^{12}$ is alkyl, and $R^{13}$ is alkyl;

$R^5$ is selected from the group consisting of hydrogen and alkyl; or $R^4$ and $R^5$ together form a fused cycloalkyl or heterocycloalkyl ring having from 5 to 6 ring atoms selected from the group consisting of carbon, nitrogen, and oxygen;

$R^6$ is selected from the group consisting of alkyl, haloalkyl, aryl, arylalkyl, heteroaryl, and heteroarylalkyl, each of which may be optionally independently substituted with one or more substitutents selected from the group consisting of halogen, alkyl, alkoxy, haloalkyl, and haloalkoxy; or $R^5$ and $R^6$ together form a fused cycloalkyl or heterocycloalkyl ring having from 5 to 6 ring atoms selected from the group consisting of carbon, nitrogen, and oxygen; and E is selected from the group consisting of S, O, N(H), $N(CH_3)$, and $CH_2$.

In some embodiments, the compound is a compound of Formula I wherein $R^1$ is OH and $R^2$ is selected from the group consisting of aryl and heteroaryl.

For example, the compound of Formula I may be a compound of Formula Ia or a salt thereof,

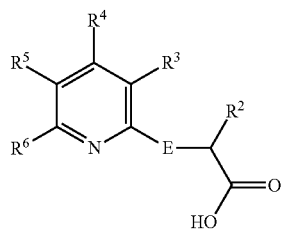

Formula Ia wherein $R^2$ is selected from the group consisting of alkyl, cycloalkyl, heterocycloalkyl, aryl and heteroaryl, each of which may be optionally independently substituted with one or more substituents selected from the group consisting of halogen, $CH_3$, $OCH_3$, $CF_3$, $OCF_3$, and CN;

$R^3$ is selected from the group consisting of hydrogen, CN, ethynyl, $CH_2N(R^9R^{10})$, and $C(O)N(R^9R^{10})$, wherein $R^9$ and $R^{10}$ are each independently selected from the group consisting of hydrogen and alkyl;

$R^4$ is selected from the group consisting of haloalkyl, aryl, arylalkyl, heteroaryl, and heteroarylalkyl, each of which may be optionally independently substituted with one or more substitutents selected from the group consisting of halogen, alkyl, alkoxy, haloalkyl, haloalkoxy, alkenyl, hydroxyalkyl, hydroxyl, $N(R^9R^{10})$, $NR^{11}C(O)R^{12}$, and $O(CO)R^{13}$, wherein $R^9$ and $R^{10}$ are independently selected from the group consisting of hydrogen and alkyl, $R^{11}$ is selected from the group consisting of hydrogen and alkyl, $R^{12}$ is alkyl, and $R^{13}$ is alkyl;

$R^5$ is selected from the group consisting of hydrogen and alkyl; or $R^4$ and $R^5$ together form a fused cycloalkyl or heterocycloalkyl ring having from 5 to 6 ring atoms selected from the group consisting of carbon, nitrogen, and oxygen;

$R^6$ is selected from the group consisting of alkyl, haloalkyl, aryl, arylalkyl, heteroaryl, and heteroarylalkyl, each of which may be optionally independently substituted with one or more substitutents selected from the group consisting of halogen, alkyl, alkoxy, haloalkyl, and haloalkoxy; or $R^5$ and $R^6$ together form a fused cycloalkyl or heterocycloalkyl ring having from 5 to 6 ring atoms selected from the group consisting of carbon, nitrogen, and oxygen; and E is selected from the group consisting of S, O, N(H), $N(CH_3)$, and $CH_2$.

In some embodiments, the compound of Formula I may be a compound of Formula Ib or a salt thereof,

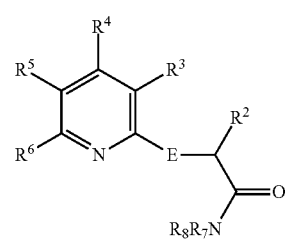

Formula Ib wherein $R^2$ is selected from the group consisting of alkyl, cycloalkyl, heterocycloalkyl, aryl and heteroaryl, each of which may be optionally independently substituted with one or more substituents selected from the group consisting of halogen, $CH_3$, $OCH_3$, $CF_3$, $OCF_3$, and CN;

$R^3$ is selected from the group consisting of hydrogen, CN, ethynyl, $CH_2N(R^9R^{10})$, and $C(O)N(R^9R^{10})$, wherein $R^9$ and $R^{10}$ are each independently selected from the group consisting of hydrogen and alkyl;

$R^4$ is selected from the group consisting of haloalkyl, aryl, arylalkyl, heteroaryl, and heteroarylalkyl, each of which may be optionally independently substituted with one or more substituents selected from the group consisting of halogen, alkyl, alkoxy, haloalkyl, haloalkoxy, alkenyl, hydroxyalkyl, hydroxyl, $N(R^9R^{10})$, $NR^{11}C(O)R^{12}$, and $O(CO)R^{13}$, wherein $R^9$ and $R^{10}$ are independently selected from the group consisting of hydrogen and alkyl, $R^{11}$ is selected from the group consisting of hydrogen and alkyl, $R^{12}$ is alkyl, and $R^{13}$ is alkyl;

$R^5$ is selected from the group consisting of hydrogen and alkyl; or $R^4$ and $R^5$ together form a fused cycloalkyl or heterocycloalkyl ring having from 5 to 6 ring atoms selected from the group consisting of carbon, nitrogen, and oxygen;

$R^6$ is selected from the group consisting of alkyl, haloalkyl, aryl, arylalkyl, heteroaryl, and heteroarylalkyl, each of which may be optionally independently substituted with one or more substituents selected from the group consisting of halogen, alkyl, alkoxy, haloalkyl, and haloalkoxy; or $R^5$ and $R^6$ together form a fused cycloalkyl or heterocycloalkyl ring having from 5 to 6 ring atoms selected from the group consisting of carbon, nitrogen, and oxygen;

$R^7$ and $R^8$ are independently selected from the group consisting of hydrogen, OH, and $CH_3$; and E is selected from the group consisting of S, O, N(H), $N(CH_3)$, and $CH_2$.

In some embodiments, the compound is a compound of Formula I wherein $R^1$ is OH.

In some embodiments, the compound is a compound of Formula I, Ia, or Ib wherein $R^2$ is phenyl. In another embodiment, the compound is a compound of Formula I, Ia, or Ib wherein $R^2$ is alkyl. In other embodiments, the compound may be a compound of Formula I, Ia, or Ib wherein $R^2$ is unsubstituted heteroaryl. For example, $R^2$ may be pyridyl, pyrimidyl (e.g., 2,6-pyrimidyl), or thienyl (e.g., 2-thienyl).

In some embodiments, the compound is a compound of Formula I, Ia, or Ib wherein $R^3$ is CN.

In some embodiments, the compound is a compound of Formula I, Ia, or Ib wherein $R^4$ is selected from the group consisting of $CF_3$, thienyl, and optionally substituted phenyl. For example, $R^4$ may be 4-halophenyl (e.g., 4-chlorophenyl) or 4-alkoxyphenyl (e.g., 4-methoxyphenyl).

In some embodiments, the compound is a compound of Formula I, Ia, or Ib wherein $R^5$ is hydrogen.

In some embodiments, the compound is a compound of Formula I, Ia, or Ib wherein $R^6$ is selected from the group consisting of methyl, ethyl, thienyl, furanyl, and optionally substituted phenyl. In one embodiment, $R^6$ may be 4-halophenyl (e.g., 4-bromophenyl) or 4-alkoxyphenyl (e.g., 4-methoxyphenyl). In some embodiments, $R^6$ may be disubstituted phenyl (e.g., 2,4-disubstituted phenyl or 3,4-disubstituted phenyl). In one embodiment, $R^6$ may be 2,4-dimethoxyphenyl or 3,4-dimethoxyphenyl.

In some embodiments, the compound is a compound of Formula I, Ia, or Ib wherein E is selected from the group consisting of S, O, and $CH_2$. For example, E may be S.

In another embodiment, the compound is a compound of Formula II or a salt thereof,

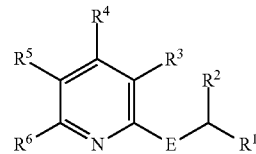

Formula II wherein $R^1$ is selected from the group consisting of a prodrug of a carboxylic acid and a carboxylic acid isostere;

$R^2$ is selected from the group consisting of alkyl, cycloalkyl, heterocycloalkyl, aryl and heteroaryl, each of which may be optionally indepentently substituted with one or more substituents selected from the group consisting of halogen, $CH_3$, $OCH_3$, $CF_3$, $OCF_3$, and CN;

$R^3$ is selected from the group consisting of hydrogen, CN, ethynyl, $CH_2N(R^9R^{10})$, and $C(O)N(R^9R^{10})$, wherein $R^9$ and $R^{10}$ are each independently selected from the group consisting of hydrogen and alkyl;

$R^4$ is selected from the group consisting of haloalkyl, aryl, arylalkyl, heteroaryl, and heteroarylalkyl, each of which may be optionally independently substituted with one or more substituents selected from the group consisting of halogen, alkyl, alkoxy, haloalkyl, haloalkoxy, alkenyl, hydroxyalkyl, hydroxyl, $N(R^9R^{10})$, $NR^{11}C(O)R^{12}$, and $O(CO)R^{13}$, wherein $R^9$ and $R^{10}$ are independently selected from the group consisting of hydrogen and alkyl, $R^{11}$ is selected from the group consisting of hydrogen and alkyl, $R^{12}$ is alkyl, and $R^{13}$ is alkyl;

$R^5$ is selected from the group consisting of hydrogen and alkyl; or $R^4$ and $R^5$ together form a fused cycloalkyl or heterocycloalkyl ring having from 5 to 6 ring atoms selected from the group consisting of carbon, nitrogen, and oxygen;

$R^6$ is selected from the group consisting of alkyl, haloalkyl, aryl, arylalkyl, heteroaryl, and heteroarylalkyl, each of which may be optionally independently substituted with one or more substituents selected from the group consisting of halogen, alkyl, alkoxy, haloalkyl, and haloalkoxy; or $R^5$ and $R^6$ together form a fused cycloalkyl or heterocycloalkyl ring having from 5 to 6 ring atoms selected from the group consisting of carbon, nitrogen, and oxygen; and E is selected from the group consisting of S, O, N(H), $N(CH_3)$, and $CH_2$.

For example, the compound of Formula II may be a compound of Formula IIa or a salt thereof,

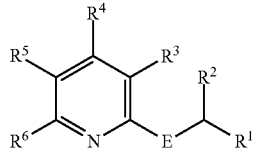

Formula IIa wherein $R^1$ is a carboxylic acid isostere;

$R^2$ is selected from the group consisting of alkyl, cycloalkyl, heterocycloalkyl, aryl and heteroaryl, each of which may be optionally independently substituted with one or more substituents selected from the group consisting of halogen, $CH_3$, $OCH_3$, $CF_3$, $OCF_3$, and CN;

$R^3$ is selected from the group consisting of hydrogen, CN, ethynyl, $CH_2N(R^9R^{10})$, and $C(O)N(R^9R^{10})$, wherein $R^9$ and $R^{10}$ are each independently selected from the group consisting of hydrogen and alkyl;

$R^4$ is selected from the group consisting of haloalkyl, aryl, arylalkyl, heteroaryl, and heteroarylalkyl, each of which may be optionally independently substituted with one or more substitutents selected from the group consisting of halogen, alkyl, alkoxy, haloalkyl, haloalkoxy, alkenyl, hydroxyalkyl, hydroxyl, $N(R^9R^{10})$, $NR^{11}C(O)R^{12}$, and $O(CO)R^{13}$, wherein $R^9$ and $R^{10}$ are independently selected from the group consisting of hydrogen and alkyl, $R^{11}$ is selected from the group consisting of hydrogen and alkyl, $R^{12}$ is alkyl, and $R^{13}$ is alkyl;

$R^5$ is selected from the group consisting of hydrogen and alkyl; or $R^4$ and $R^5$ together form a fused cycloalkyl or heterocycloalkyl ring having from 5 to 6 ring atoms selected from the group consisting of carbon, nitrogen, and oxygen;

$R^6$ is selected from the group consisting of alkyl, haloalkyl, aryl, arylalkyl, heteroaryl, and heteroarylalkyl, each of which may be optionally independently substituted with one or more substitutents selected from the group consisting of halogen, alkyl, alkoxy, haloalkyl, and haloalkoxy; or $R^5$ and $R^6$ together form a fused cycloalkyl or heterocycloalkyl ring having from 5 to 6 ring atoms selected from the group consisting of carbon, nitrogen, and oxygen; and E is selected from the group consisting of S, O, N(H), $N(CH_3)$, and $CH_2$.

Alternatively, the compound of Formula II may be a compound of Formula IIb or a salt thereof, Formula IIb

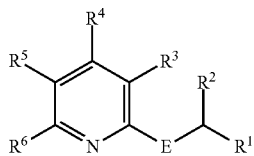

wherein $R^1$ is a prodrug of carboxylic acid;

$R^2$ is selected from the group consisting of alkyl, cycloalkyl, heterocycloalkyl, aryl and heteroaryl, each of which may be optionally independently substituted with one or more substitutents selected from the group consisting of halogen, $CH_3$, $OCH_3$, $CF_3$, $OCF_3$, and CN;

$R^3$ is selected from the group consisting of hydrogen, CN, ethynyl, $CH_2N(R^9R^{10})$, and $C(O)N(R^9R^{10})$, wherein $R^9$ and $R^{10}$ are each independently selected from the group consisting of hydrogen and alkyl;

$R^4$ is selected from the group consisting of haloalkyl, aryl, arylalkyl, heteroaryl, and heteroarylalkyl, each of which may be optionally independently substituted with one or more substitutents selected from the group consisting of halogen, alkyl, alkoxy, haloalkyl, haloalkoxy, alkenyl, hydroxyalkyl, hydroxyl, $N(R^9R^{10})$, $NR^{11}C(O)R^{12}$, and $O(CO)R^{13}$, wherein $R^9$ and $R^{10}$ are independently selected from the group consisting of hydrogen and alkyl, $R^{11}$ is selected from the group consisting of hydrogen and alkyl, $R^{12}$ is alkyl, and $R^{13}$ is alkyl;

$R^5$ is selected from the group consisting of hydrogen or alkyl; or $R^4$ and $R^5$ together form a fused cycloalkyl or heterocycloalkyl ring having from 5 to 6 ring atoms selected from the group consisting of carbon, nitrogen, and oxygen;

$R^6$ is selected from the group consisting of alkyl, haloalkyl, aryl, arylalkyl, heteroaryl, and heteroarylalkyl, each of which may be optionally independently substituted with one or more substitutents selected from the group consisting of halogen, alkyl, alkoxy, haloalkyl, and haloalkoxy; or $R^5$ and $R^6$ together form a fused cycloalkyl or heterocycloalkyl ring having from 5 to 6 ring atoms selected from the group consisting of carbon, nitrogen, and oxygen; and E is selected from the group consisting of S, O, N(H), $N(CH_3)$, and $CH_2$.

In some embodiments, the compound is a compound of Formula II, IIa, or IIb wherein $R^2$ is phenyl.

In some embodiments, the compound is a compound of Formula II, IIa, or IIb wherein $R^3$ is CN.

In some embodiments, the compound is a compound of Formula II, IIa, or IIb wherein $R^4$ is selected from the group consisting of $CF_3$, thienyl, and optionally substituted phenyl. For example, $R^4$ may be 4-halophenyl (e.g., 4-chlorophenyl) or 4-alkoxyphenyl (e.g., 4-methoxyphenyl).

In some embodiments, the compound is a compound of Formula II, IIa, or IIb wherein $R^5$ is hydrogen.

In some embodiments, the compound is a compound of Formula II, IIa, or IIb wherein $R^6$ is selected from the group consisting of methyl, ethyl, thienyl, furanyl, and optionally substituted phenyl. In one embodiment, $R^6$ may be 4-halophenyl (e.g., 4-bromophenyl) or 4-alkoxyphenyl (e.g., 4-methoxyphenyl). In some embodiments, $R^6$ may be disubstituted phenyl (e.g., 2,4-disubstituted phenyl or 3,4-disubstituted phenyl). In other embodiments, $R^6$ may be 2,4-dimethoxyphenyl or 3,4-dimethoxyphenyl.

In some embodiments, the compound is a compound of Formula II, IIa, or IIb wherein E is selected from the group consisting of S, O, and $CH_2$. In other embodiments, E may be S.

In some embodiments, the compound is a compound of Formula II or IIa wherein $R^1$ is a carboxylic acid isostere selected from the group consisting of tetrazolyl, aminosulfonyl, acylaminosulfonyl, methyl sulfonylcarbamyl, thiazolidinedionyl, oxazolidinedionyl, oxadiazolonyl, $P(O)(OH)_2$, P(O)(OH)H, and $SO_3H$.

In some embodiments, the compound is a compound of Formula II or IIb wherein $R^1$ is a prodrug of carboxylic acid selected from the group consisting of $CH_2OH$ and ester group $C(O)OR^{14}$, wherein $R^{14}$ is selected from the group consisting of methyl, ethyl, 2-oxopropyl, 2-morpholinoethyl, and pivaloyloxymethyl. For example, in some embodiments, $R^1$ is $C(O)OCH_3$. In other embodiments, $R^1$ is $CH_2OH$.

As used herein, the term "halo" or "halogen" refers to any radical of fluorine, chlorine, bromine or iodine.

The term "alkyl" as employed herein, by itself or as part of another group, refers to both straight and branched chain radicals of up to ten carbons, which may be optionally independently substituted. Non-limiting examples of $C_1$-$C_{10}$ alkyl groups include methyl, ethyl, propyl, isopropyl, butyl, sec-butyl, tert-butyl, 3-pentyl, hexyl and octyl groups. For example, in some embodiments, the term "alkyl" as used herein, by itself or as part of another group, refers to a straight or branched chain radical comprising from one to six carbon atoms.

The term "hydroxyalkyl" as employed herein, refers to both straight and branched chain alkyl radicals having a hydroxyl substituent. The hydroxyl substituent can be bound to any carbon of the alkyl chain. Non-limiting examples include $CH_2OH$, $CH_2CH_2OH$, $CH_2CH(OH)CH_3$ and $CH_2CH(OH)CH_2CH_3$. For example, in some embodiments, the term "hydroxyalkyl" as employed herein refers to a straight or branched chain radical comprising from one to four carbon atoms and having one or more hydroxyl substituents.

The term "haloalkyl" as employed herein, by itself or as part of another group, refers to an alkyl group, as defined herein, substituted with at least one halogen. Non-limiting examples of haloalkyl groups include trifluromethyl and 2,2,2-trifluoroethyl.

The term "alkoxy" as employed herein, by itself or as part of another group, refers to an alkyl group, as defined herein, appended to the parent molecular moiety through an oxygen atom. Non-limiting examples of alkoxy groups include methoxy, ethoxy, propoxy, 2-propoxy, butoxy, tert-butoxy, pentyloxy, and hexyloxy.

The term "haloalkoxy" as employed herein, by itself or as part of another group, refers to an alkoxy group as defined herein, wherein the alkyl moiety of the alkoxy group is further substituted with at least one halogen. Non-limiting example of haloalkoxy groups include trifluoromethoxy, and 2,2-dichloroethoxy.

The term "cycloalkyl" as used herein refers to an alkyl group comprising a closed ring comprising from 3 to 8 carbon atoms. Non-limiting examples of cycloalkyl groups include cyclopropyl, cyclobutyl, cyclopentyl, cyclohexyl and cycloheptyl.

As used herein, the term "heterocyclyl," "heterocycloalkyl," or "heterocycle" refers to a saturated or partially saturated 3 to 7 membered monocyclic, or 7 to 10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and includes any bicyclic group in which any of the above-defined heterocyclic rings is fused to a benzene ring, and wherein the heterocyclic ring can be substituted on carbon or on a nitrogen atom if the resulting compound is stable. Non-limiting examples of common saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

The term "aryl" as employed herein by itself or as part of another group refers to monocyclic, bicyclic or tricyclic aromatic groups containing from 6 to 14 carbons in the ring. Common aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroactoms. Example heteroaryl groups include thienyl (thiophenyl), benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-α]pyrimidin-4-one, pyrazolo[1,5-α]pyrimidinyl, including without limitation pyrazolo[1,5-α]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "prodrug of a carboxylic acid" as employed herein refers to any compound or moiety that can be transformed through chemical or metabolic (enzymatic) processes in vivo to produce carboxylic acid. The prodrug of a carboxylic acid may be an inactive or less active compound than the parent compound containing the carboxylic acid. A prodrug of a carboxylic acid may have physicochemical properties which result in improved uptake, distribution or metabolism. In a non-limiting example of a prodrug of a carboxylic acid, the carboxylic acid can be esterified with a methyl or ethyl group to yield an ester and when the carboxylic acid ester is administered to a biological system (e.g. plant or human subject) the ester group may be, for example, converted enzymatically, non-enzymatically, oxidatively or hydrolytically to the carboxylate group. Additionally, cleavable carboxylic acid prodrug moieties include, but are not limited to, substituted and unsubstituted, branched and unbranched lower alkyl ester moieties (methyl ester, ethyl esters, propyl esters, butyl esters, pentyl esters, cyclopentyl esters, hexyl esters and cyclohexyl esters), lower alkenyl esters, acyloxy lower alkyl esters (e.g. pivaloyloxymethyl ester), aryl esters, and aryl lower alkyl esters (e.g. benzyl esters). Alternatively, hydroxyalkyl groups may be oxidized in vivo to a carboxylic acid. Additionally, conventional procedures for selection and preparation of suitable prodrug of a carboxylic acid derivatives are known in the art including, for example, as described in "Prodrugs: Challengs and Rewards", Part 2, Volume 5 (2007) pages 3-29 and "Current Methods in Medicinal Chemistry and Biological Physics" Volume 2 (2008) pages 187-214", which are incorporated herein by reference.

The term "carboxylic acid isostere" as employed herein includes each and all of (1) carboxylic acid isosteres having one or more of the following, the same number of atoms, the same number of valence electrons, and exhibiting similar reactive electron shells, volumes and shapes as compared to a carboxylic acid substituent, and (2) non-classical isosteres which fit the broadest definition of isosters and produce biological effects similar to a carboxylic acid substituent. Non-limiting examples of carboxylic acid isosteres include tetrazolyl, aminosulfonyl, acylaminosulfonyl, methyl sulfonyl carbamyl, thiazolidinedionyl, oxazolidinedionyl, oxadiazolonyl, $P(O)(OH)_2$, $P(O)(OH)H$, and $SO_3H$. The concept of carboxylic acid isostere in drug design and the properties of several isosters are known in the art and described, for example, by Ballatore at al in ChemMedChem 2013, 8, pages 385-395, which is incorporated herein by reference.

Non-limiting examples of species include 2-((4-(4-chlorophenyl)-3-cyano-6-(thiophen-2-yl)pyridin-2-yl)thio)-2-phenylacetic acid of Formula Ia-i, or a salt thereof,

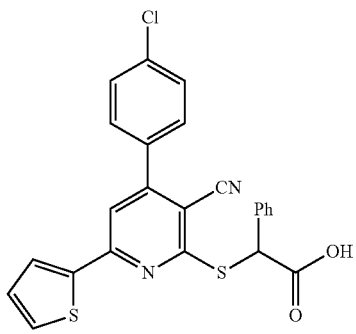

Formula Ia-i 2-((3-cyano-6-(thiophen-2-yl)-4-(trifluoromethyl)pyridin-2-yl)thio)-2-phenylacetic acid of Formula Ia-ii, or a salt thereof,

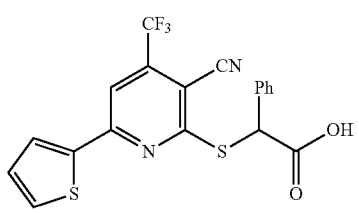

Formula Ia-ii 2-((3-cyano-4,6-di(thiophen-2-yl)pyridin-2-yl)thio)-2-phenylacetic acid of Formula Ia-iii, or a salt thereof,

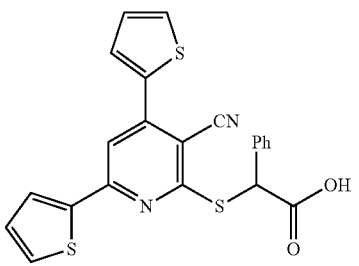

Formula Ia-iii 2-((3-cyano-4-phenyl-6-(thiophen-2-yl)pyridin-2-yl)thio)-2-phenylacetic acid of Formula Ia-iv, or a salt thereof,

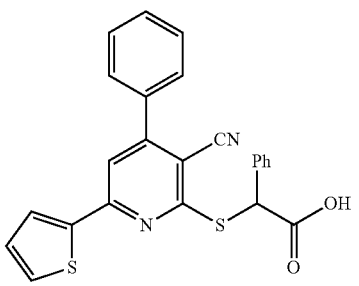

Formula Ia-iv 2-((3-cyano-4-(4-methoxyphenyl)-6-(thiophen-2-yl)pyridin-2-yl)thio)-2-phenylacetic acid of Formula Ia-v, or a salt thereof,+

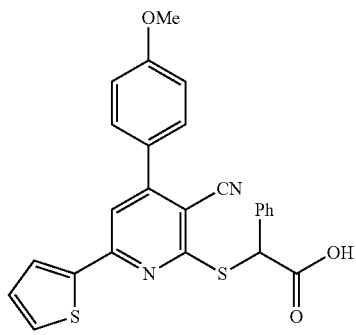

Formula Ia-v 2-((3-cyano-8-methyl-4-(thiophen-2-yl)-5,6,7,8-tetrahydro-1,8-naphthyridin-2-yl)thio)-2-phenylacetic acid of Formula Ia-vi, or a salt thereof,

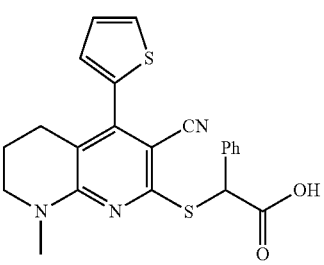

Formula Ia-vi 2-((4-cyano-1-(thiophen-2-yl)-5,6,7,8-tetrahydroisoquinolin-3-yl)thio)-2-phenylacetic acid of Formula Ia-vii, or a salt thereof,

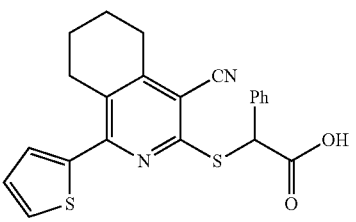

Formula Ia-vii 2-((3-cyano-6-(2,4-dimethoxyphenyl)-4-(trifluoromethyl)pyridin-2-yl)thio)-2-phenylacetic acid of Formula Ia-viii, or a salt thereof,

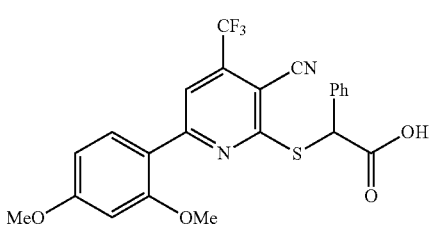

Formula Ia-viii 2-((3-cyano-6-(3,4-dimethoxyphenyl)-4-(trifluoromethyl)pyridin-2-yl)thio)-2-phenylacetic acid of Formula Ia-ix, or a salt thereof,

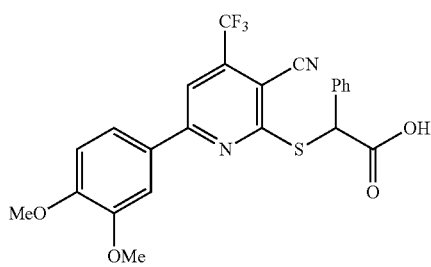

Formula Ia-ix 2-((6-(4-bromophenyl)-3-cyano-4-(trifluoromethyl)pyridin-2-yl)thio)-2-phenylacetic acid of Formula Ia-x, or a salt thereof,

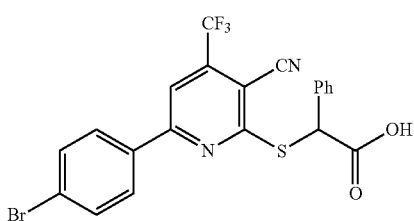

Formula Ia-x 2-((3-cyano-6-(furan-2-yl)-4-(trifluoromethyl)pyridin-2-yl)thio)-2-phenylacetic acid of Formula Ia-xi, or a salt thereof,

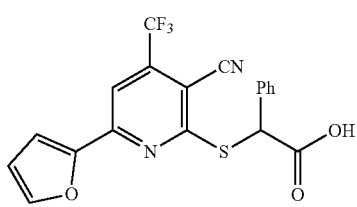

Formula Ia-xi 2-((3-cyano-4,6-diphenylpyridin-2-yl)thio)-2-phenylacetic acid of Formula Ia-xii, or a salt thereof,

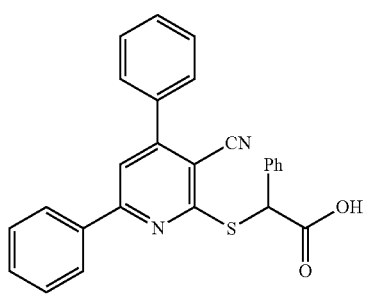

Formula Ia-xii 2-((3-cyano-4-(thiophen-2-yl)-5,6,7,8-tetrahydroquinolin-2-yl)thio)-2-phenylacetic acid of Formula Ia-xiii, or a salt thereof,

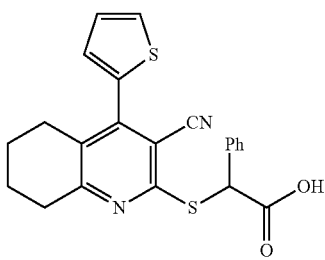

Formula Ia-xiii 2-((3-cyano-4-(4-methoxyphenyl)-6-(thiophen-2-yl)pyridin-2-yl)thio)-2-phenylacetic acid of Formula Ia-xiv, or a salt thereof,

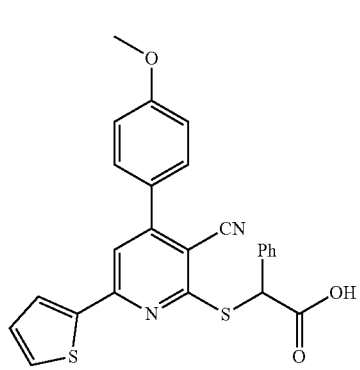

Formula Ia-xiv 2-((4-cyano-1-ethyl-5,6,7,8-tetrahydroisoquinolin-3-yl)thio)-2-phenylacetic acid of Formula Ia-xv, or a salt thereof,

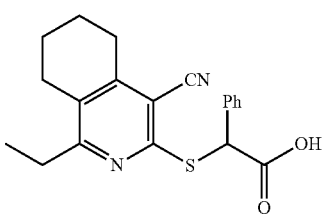

Formula Ia-xv 2-((3-cyano-6-methyl-4-(trifluoromethyl)pyridin-2-yl)thio)-2-phenylacetic acid of Formula Ia-xvi, or a salt thereof,

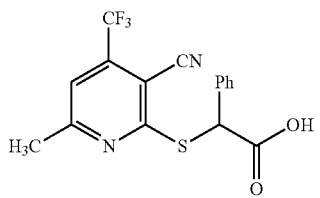

Formula Ia-xvi 2-((3-cyano-4-phenyl-5,6,7,8-tetrahydroquinolin-2-yl)thio)-2-phenylacetic acid of Formula Ia-xvii, or a salt thereof,

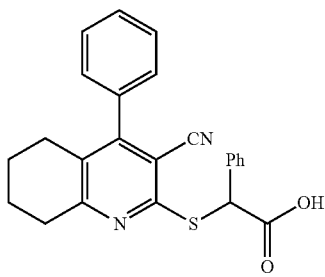

Formula Ia-xvii

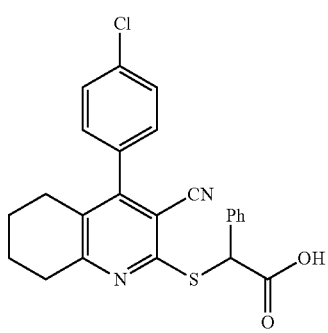

Formula Ia-xviii 2-((4-(4-chlorophenyl)-3-cyano-5,6,7,8-tetrahydronaph-thalen-2-yl)thio)-2-phenylacetic acid of Formula Ia-xviii, or a salt thereof, 2-((4-(4-methoxyphenyl)-6-(thiophen-2-yl)pyridin-2-yl)thio)-2-phenylacetic acid of Formula Ia-xix or a salt thereof,

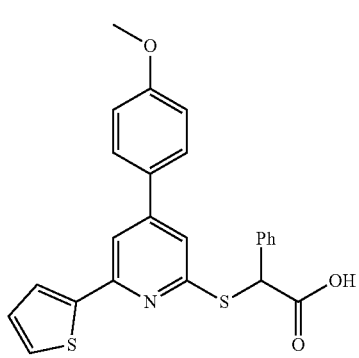

Formula Ia-xix 2-((3-cyano-6-(furan-2-yl)-4-(4-methoxyphenyl)pyridin-2-yl)thio)-2-phenylacetic acid of Formula Ia-xx, or a salt thereof,

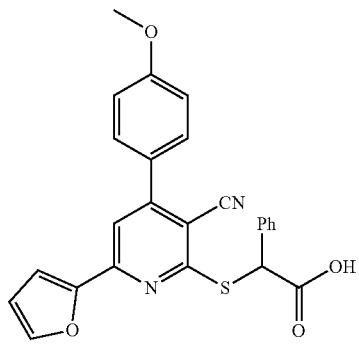

Formula Ia-xx 2-((3-cyano-6-(thiophen-2-yl)-4-(p-tolyl)pyridin-2-yl)thio)-2-phenylacetic acid of Formula Ia-xxi, or a salt thereof,

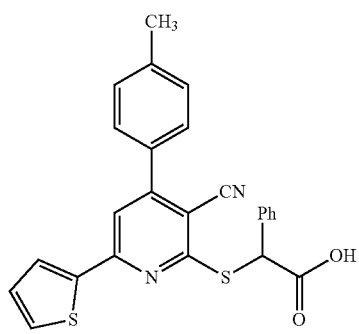

Formula Ia-xxi 2-((3-cyano-4-(4-fluorophenyl)-6-(thiophen-2-yl)pyridin-2-yl)thio)-2-phenylacetic acid of Formula Ia-xxii, or a salt thereof,

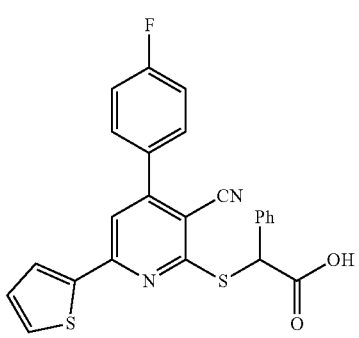

Formula Ia-xxii 2-((4-(4-bromophenyl)-3-cyano-6-(thiophen-2-yl)pyridin-2-yl)thio)-2-phenylacetic acid of Formula Ia-xxiii, or a salt thereof,

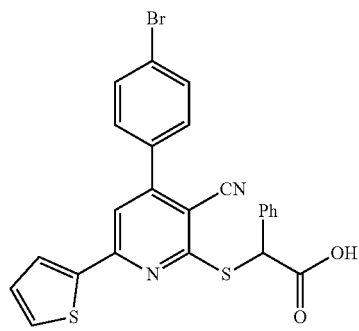

2-((3-cyano-6-(furan-2-yl)-4-(thiophen-2-yl)pyridin-2-yl)thio)-2-phenylacetic acid of Formula Ia-xxiv, or a salt thereof,

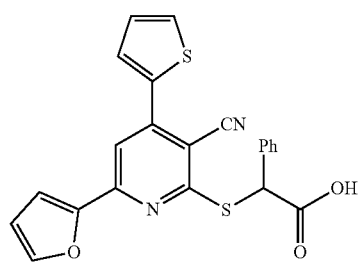
Formula Ia-xxiv 2-((3-cyano-4,6-di(furan-2-yl)pyridin-2-yl)thio)-2-phenylacetic acid of Formula Ia-xxv, or a salt thereof,

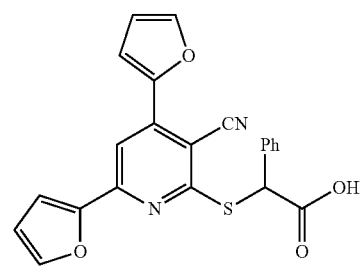
Formula Ia-xxv 2-((3-cyano-4-(4-methoxyphenyl)-5,6,7,8-tetrahydroquinolin-2-yl)thio)-2-phenylacetic acid of Formula Ia-xxvi, or a salt thereof

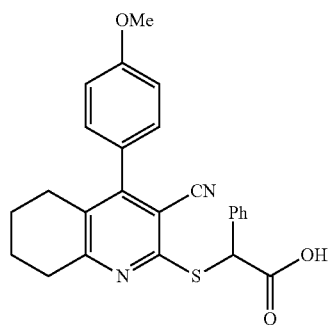
Formula Ia-xxvi 2-((3-cyano-4-(thiophen-2-yl)-5,6,7,8-tetrahydroquinolin-2-yl)oxy)-2-phenylacetic acid of Formula Ia-xxvii, or a salt thereof,

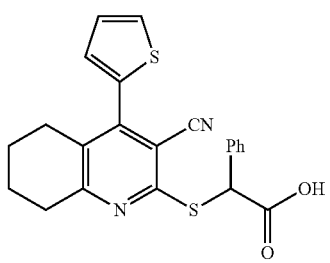
Formula Ia-xxvii 2-((3-cyano-4-(4-methoxyphenyl)-6-(1-oxidothiophen-2-yl)pyridin-2-yl)oxy)-2-phenylacetic acid of Formula Ia-xxviii, or a salt thereof,

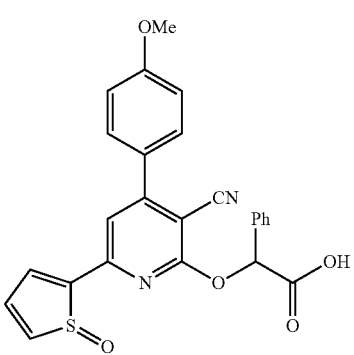
Formula Ia-xxviii 2-((3-cyano-4-(4-methoxyphenyl)-6-(thiophen-2-yl)pyridin-2-yl)thio)butanoic acid of Formula Ia-xxix, or a salt thereof,

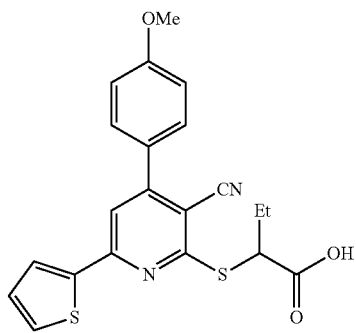

Formula Ia-xxix 2-((3-cyano-4-(4-methoxyphenyl)-6-(pyrimidin-2-yl)pyridin-2-yl)thio)-2-phenylacetic acid of Formula Ia-xxx, or a salt thereof

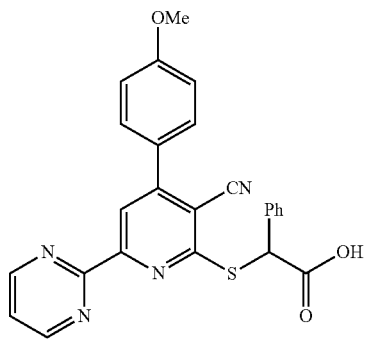

Formula Ia-xxx 2-((3-cyano-6-(3-methoxy-1-methyl-1H-pyrrol-2-yl)-4-(4-methoxyphenyl)pyridin-2-yl)thio)-2-phenylacetic acid of Formula Ia-xxxi, or a salt thereof,

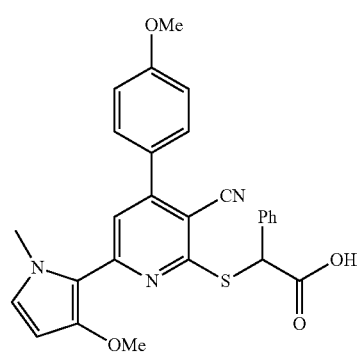

Formula Ia-xxxi 2-((3-cyano-4-(furan-2-yl)-6-(thiophen-2-yl)pyridin-2-yl)thio)-2-phenylacetic acid of Formula Ia-xxxii, or a salt thereof,

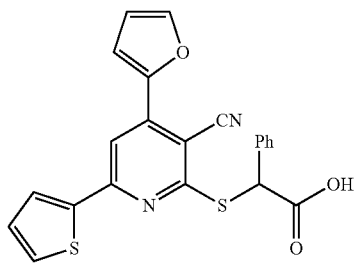

Formula Ia-xxxii 2-((3-cyano-4-(thiophen-2-yl)-5,6,7,8-tetrahydroquinolin-2-yl)thio)-2-phenylacetamide of Formula Ib-i, or a salt thereof,

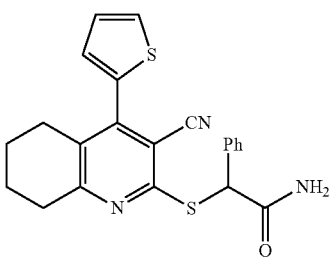

Formula Ib-i 2-((3-cyano-4-(4-methoxyphenyl)-6-(thiophen-2-yl)pyridin-2-yl)thio)-2-phenylacetamide of Formula Ib-ii, or a salt thereof,

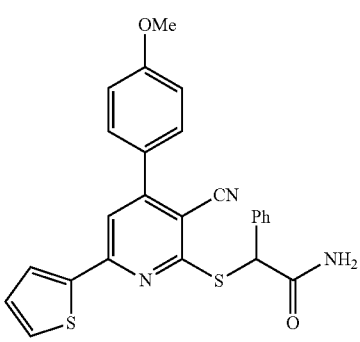

Formula Ib-ii 2-((3-cyano-4-(4-methoxyphenyl)-6-(thiophen-2-yl)pyridin-2-yl)thio)-N-hydroxy-2-phenylacetamide of Formula Ib-iii, or a salt thereof, Formula Ib-iii

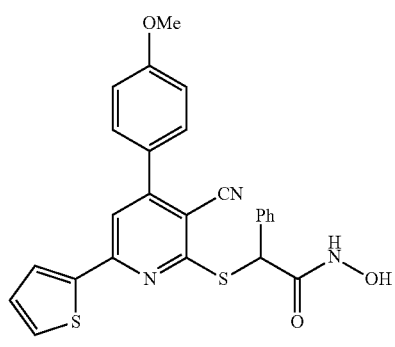

4-(4-methoxyphenyl)-2-((phenyl(1H-tetrazol-5-yl)methyl)thio)-6-(thiophen-2-yl)nicotinonitrile of Formula IIa-i, or a salt thereof, Formula IIa-i

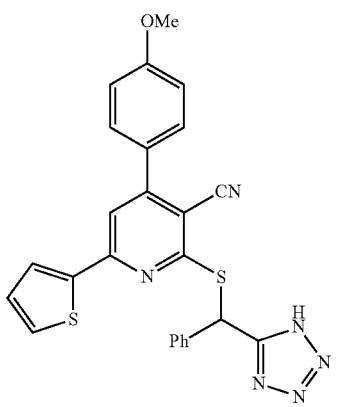

(((3-cyano-4-(4-methoxyphenyl)-6-(thiophen-2-yl)pyridin-2-yl)thio)(phenyl)methyl)phosphonic acid of Formula IIa-ii, or a salt thereof, Formula IIa-ii

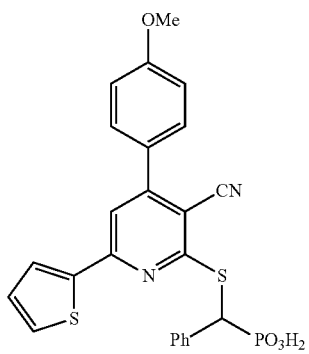

(((3-cyano-4-(4-methoxyphenyl)-6-(thiophen-2-yl)pyridin-2-yl)thio)(phenyl)methyl)phosphinic acid of Formula IIa-iii, or a salt thereof, Formula IIa-iii

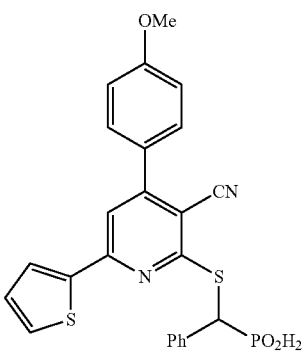

((3-cyano-4-(4-methoxyphenyl)-6-(thiophen-2-yl)pyridin-2-yl)thio)(phenyl)methanesulfonic acid of Formula IIa-iv, or a salt thereof, Formula IIa-iv

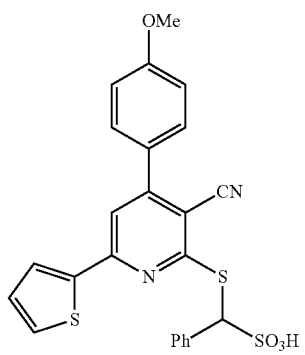

((3-cyano-4-(4-methoxyphenyl)-6-(thiophen-2-yl)pyridin-2-yl)thio)(phenyl)methanesulfonamide of Formula IIa-v, or a salt thereof, Formula IIa-v

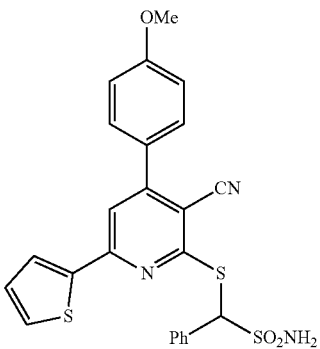

2-((3-cyano-4-(4-methoxyphenyl)-6-(thiophen-2-yl)pyridin-2-yl)thio)-N-(methylsulfonyl)-2-phenylacetamide of Formula IIa-vi, or a salt thereof,

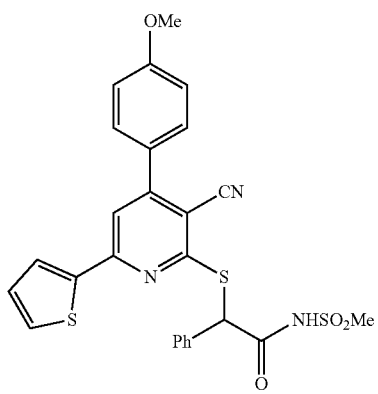

2-(((2,4-dioxothiazolidin-5-yl)(phenyl)methyl)thio)-4-(4-methoxyphenyl)-6-(thiophen-2-yl)nicotinonitrile of Formula IIa-vii, or a salt thereof,

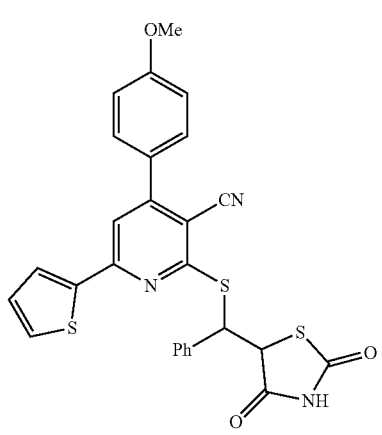

2-(((2,4-dioxooxazolidin-5-yl)(phenyl)methyl)thio)-4-(4-methoxyphenyl)-6-(thiophen-2-yl)nicotinonitrile of Formula IIa-viii, or a salt thereof,

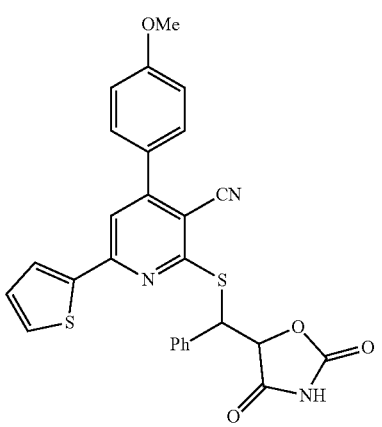

4-(4-methoxyphenyl)-2-(((5-oxo-4,5-dihydro-1,2,4-oxadiazol-3-yl)(phenyl)methyl)thio)-6-(thiophen-2-yl)nicotinonitrile of Formula IIa-ix, or a salt thereof,

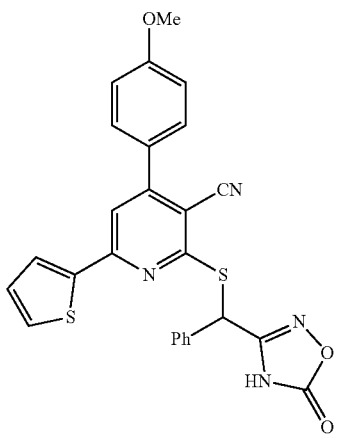

2-((2-hydroxy-1-phenylethyl)thio)-4-(4-methoxyphenyl)-6-(thiophen-2-yl)nicotinonitrile of Formula IIb-i, or a salt thereof,

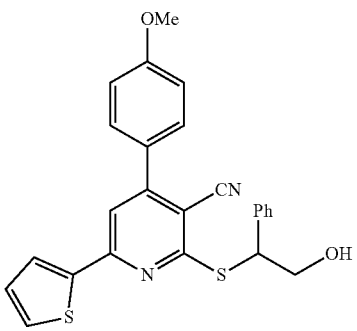

2-((2-hydroxy-1-phenylethyl)thio)-4-(thiophen-2-yl)-5,6,7,8-tetrahydroquinoline-3-carbonitrile of Formula IIb-ii, or a salt thereof,

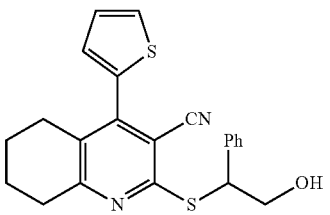

methyl 2-((3-cyano-6-(thiophen-2-yl)-4-(trifluoromethyl)pyridin-2-yl)thio)-2-phenylacetate of Formula IIb-iii, or a salt thereof, and

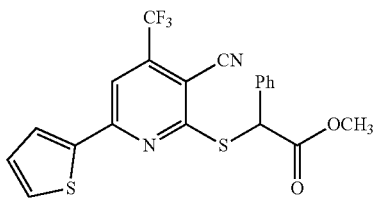

Formula IIb-iii 4-(furan-2-yl)-2-((2-hydroxy-1-phenylethyl)thio)-6-(thiophen-2-yl)nicotinonitrile of Formula IIb-iv, or a salt thereof.

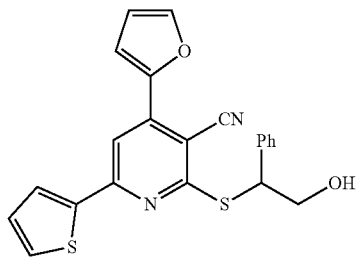

Formula IIb-iv

Enantiomers

The compounds described herein can be present as a racemic mixture, as a mixture of two enantiomers at different ratios, or as a single enantiomer. Compositions that are enriched with respect to one enantiomer, or which comprise substantially a single enantionmer, may be prepared using any technique known in the art, including chiral separation techniques known in the art (e.g., chiral chromatography or asymmetric synthesis).

Compositions

In another aspect, the present disclosure is generally related to a composition comprising an effective amount of a compound (e.g., a compound of Formula I, Ia, Ib, II, IIa, or IIb) as described herein as an ACCase modulator or inhibitor for use in administration to a plant, a seed, or soil to control fungal pathogens.

For example, the composition may be an aqueous composition.

Generally, compositions described herein can comprise any adjuvants, excipients, or other desirable components known in the art.

Non-limiting examples of additional ingredients include surfactants, co-surfactants, permeation enhancers, and co-solvents. For example, the composition may comprise as SPAN surfactants, TWEEN surfactants, TRITON surfactants, MAKON surfactants, IGEPAL surfactants, BRIJ surfactants, MORWET surfactants, PLURONIC surfactants, LANEXOL surfactants, ATLOX surfactants, ATLAS surfactants, SURFYNOL surfactants, TERGITOL surfactants, DOWFAX surfactants, TOXIMUL surfactants, SILWET surfactants, SYLGARD surfactants, BREAK THRU surfactants, PHYTOSAN, SOLUPLUS, cyclodextrans, polypropylene glycol, ethyl lactate, methyl soyate/ethyl lactate co-solvent blends (e.g., STEPOSOL), isopropanol, acetone, ethylene glycol, propylene glycol, n-alkylpyrrolidones (e.g., the AGSOLEX series), a petroleum based-oil (e.g., AROMATIC 200) or a mineral oil (e.g., paraffin oil)).

For example, in some embodiments, a composition comprises a surfactant. Non-limiting examples of surfactants include SPAN 20, SPAN 40, SPAN 80, SPAN 85, TWEEN 20, TWEEN 40, TWEEN 80, TWEEN 85, TRITON X 100, MAKON 10, IGEPAL CO 630, BRIJ 35, BRIJ 97, TERGITOL TMN 6, DOWFAX 3B2, PHYSAN and TOXIMUL TA 15.

In some embodiments, a composition comprises a co-solvent. Examples of co-solvents that can be used include ethyl lactate, methyl soyate/ethyl lactate co-solvent blends (e.g., STEPOSOL), isopropanol, acetone, 1,2-propanediol, n-alkylpyrrolidones (e.g., the AGSOLEX series), a petroleum based-oil (e.g., AROMATIC 200) or a mineral oil (e.g., paraffin oil)).

In some embodiments, a composition may be formulated, mixed in a tank, combined on a seed by overcoating, or recommended for use with one or more additional active ingredients on a seed, plant, or soil. The additional active ingredient may be, for example, an additional pesticide. The pesticide may be, for example, an insecticide, a fungicide, an herbicide, or an additional nematicide.

Non-limiting examples of insecticides and nematicides include carbamates, diamides, macrocyclic lactones, neonicotinoids, organophosphates, phenylpyrazoles, pyrethrins, spinosyns, synthetic pyrethroids, tetronic and tetramic acids. In another embodiment, insecticides and nematicides include abamectin, aldicarb, aldoxycarb, bifenthrin, carbofuran, chlorantraniliprole, clothianidin, cyfluthrin, cyhalothrin, cypermethrin, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, spinetoram, spinosad, spirodichlofen, spirotetramat, tefluthrin, thiacloprid, thiamethoxam, and thiodicarb.

In some embodiments, a composition comprises an insecticide and/or acaricide that inhibits ACCase activity. Non-limiting examples include tetramic acids such as spirotetramat, and tetronic acids including spiromesifen and spirodiclofen.

In some embodiments, the composition comprises one or more nematicidal compounds as described in U.S. Pub. Nos. 2009/0048311 A1 or 2011/028320 A1, or WO 2012/030887 A1, the contents of which are herein incorporated by reference.

For example, in some embodiments, the composition comprises 3-phenyl-5-(thiophen-2-yl)-1,2,4-oxadiazole.

Non-limiting examples of herbicides include ACCase inhibitors, acetanilides, AHAS modulators or inhibitors, carotenoid biosynthesis inhibitors, EPSPS modulators or inhibitors, glutamine synthetase modulators or inhibitors, PPO modulators or inhibitors, PS II modulators or inhibitors, and synthetic auxins. Non-limiting examples of herbicides include acetochlor, clethodim, dicamba, flumioxazin, fomesafen, glyphosate, glufosinate, mesotrione, quizalofop, saflufenacil, sulcotrione, and 2,4-D.

In one embodiment, an herbicide is selected that inhibits ACCase activity. Non-limiting examples include herbicidal aryloxyphenoxypropionates such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, kuicaoxi, metamifop, propaquizafop, quizalofop, quizalofop-P, and trifop, herbicidal cyclohexanediones such as alloxydim, butroxydim, clethodim, cloproxydim, cycloxydim, profoxydim, sethoxydim, tepraloxydim, and tralkoxydim, as well as the herbicide pinoxaden.

The herbicides cycloxydim and sethoxydim are known to exhibit moderate antifungal activity alone, and, without being bound to a particular theory, it is believed that the combination of these species with the compounds described herein may enhance fungal control by the additional suppression of ACCase.

A composition may comprise one or more additional fungicides. Non-limiting examples of additional fungicides include aromatic hydrocarbons, benzimidazoles, benzothiadiazole, carboxamides, carboxylic acid amides, morpholines, phenylamides, phosphonates, quinine outside inhibitors (e.g. strobilurins), thiazolidines, thiophanates, thiophene carboxamides, and triazoles, Particular examples of fungicides include acibenzolar-S-methyl, azoxystrobin, benalaxyl, bixafen, boscalid, carbendazim, cyproconazole, dimethomorph, epoxiconazole, fluopyram, fluoxastrobin, flutianil, flutolanil, fluxapyroxad, fosetyl-Al, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thifluzamide, thiophanate, tolclofos-methyl, trifloxystrobin, and triticonazole.

In some embodiments, the composition comprises one or more additional fungicides that modulate or inhibit ACCase activity.

A composition may also comprise one or more additional active substances, including biological control agents, microbial extracts, natural products, plant growth activators and/or plant defense agents. Non-limiting examples of biological control agents include bacteria, fungi, beneficial nematodes, and viruses.

For example, in certain embodiments, the biological control agent can be a bacterium of the genus *Actinomycetes, Agrobacterium, Arthrobacter, Alcaligenes, Aureobacterium, Azobacter, Beijerinckia, Brevibacillus, Burkholderia, Chromobacterium, Clostridium, Clavibacter, Comamonas, Corynebacterium, Curtobacterium, Enterobacter, Flavobacterium, Gluconobacter, Hydrogenophage, Klebsiella, Methylobacterium, Paenibacillus, Pasteuria, Photorhabdus, Phyllobacterium, Pseudomonas, Rhizobium, Serratia, Sphingobacterium, Stenotrophomonas, Variovax,* and *Xenorhabdus.*

In some embodiments, the biological control agent can be a fungus of the genus *Alternaria, Ampelomyces, Aspergillus, Aureobasidium, Beauveria, Colletotrichum, Coniothyrium, Gliocladium, Metarhizium, Muscodor, Paecilomyces, Trichoderma, Typhula, Ulocladium,* and *Verticillium.* In particular embodiments the fungus is *Beauveria bassiana, Coniothyrium minitans, Gliocladium virens, Muscodor albus, Paecilomyces lilacinus,* or *Trichoderma polysporum.*

In further embodiments, the biological control agents can be plant growth activators or plant defense agents including, but not limited to harpin, Reynoutria sachalinensis, jasmonate, lipochitooligosaccharides, and isoflavones.

Methods of Use

ACCase is an essential catalyst for the rate-limiting step of fatty acid biosynthesis in both eukaryotes and prokaryotes. Without being bound to a particular theory, it is believed that the compounds disclosed herein modulate or inhibit ACCase. In one embodiment, a compound (e.g., a compound of Formula I, Ia, Ib, II, IIa, or IIb) as described herein is used as a ACCase modulator. Additionally, compounds as described herein of Formulas I, Ia, Ib, II, IIa, and IIb are also believed to exhibit control of phytopathogenic fungi as described herein. In one embodiment, the compounds disclosed herein are administered to a plant, a seed, or soil in a composition as described herein to control fungal pathogens, including using the compounds as described herein with any adjuvants, excipients, or other desirable components as described herein or known in the art and formulating, mixing, or combining one or more additional active ingredients. The additional active ingredient may be, for example, an additional pesticide. The pesticide may be, for example, an insecticide, a fungicide, an herbicide, or an additional nematicide as described herein or otherwise known in the art.

Compounds and compositions described herein can be administered to seeds, plants, or the environment of plants (e.g., soil) wherein the control of phytopathogenic fungi is desired. For example, in one embodiment, the disclosure is generally related to a method of controlling fungal pathogens, the method comprising administering to a plant, a seed or soil a composition comprising an effective amount of a compound as described herein.

Non-limiting examples of plants that may be protected from fungal pathogens in accordance with the methods described herein include monocotyledon crops such as corn, wheat, barley, rye, rice, sorghum, oat; sugarcane and turf; and dicotyledon crops such as cotton, sugar beet, peanut, potato, sweet potato, yam, sunflower, soybean, alfalfa, canola, grapes, tobacco; vegetables including Solanaceae vegetables such as eggplant, tomato, green pepper and pepper; Cucurbitaceae vegetables such as cucumber, pumpkin, zucchini, watermelon, melon and squash; Brassicaceae vegetables such as radish, turnip, horseradish, Chinese cabbage, cabbage, leaf mustard, broccoli and cauliflower; Asteraceae vegetables such as artichoke and lettuce; Liliaceae vegetables such as leek, onion, garlic and asparagus; Apiaceae vegetables such as carrot, parsley, celery and parsnip; Chenopodiaceae vegetables such as spinach and chard; Lamiaceae vegetables such as mint and basil; flowers such as petunia, morning glory, carnation, chrysanthemum and rose; foliage plants; fruit trees such as pome fruits (e.g., apple, pear and Japanese pear), stone fruits (e.g., peach, plum, nectarine, cherry, apricot and prune), citrus (e.g., orange, lemon, lime and grapefruit), tree nuts (e.g., chestnut, pecan, walnut, hazel, almond, pistachio, cashew and macadamia), berries such as blueberry, cranberry, blackberry, strawberry and raspberry; persimmon; olive; loquat; banana; coffee; palm; coco; the other trees such tea, mulberry, flower trees, and landscape trees (e.g., ash, birch, dogwood, eucalyptus, ginkgo, lilac, maple, oak, poplar, Formosa sweetgum, sycamore, fir, hemlock fir, needle juniper, pine, spruce, yew).

Non-limiting examples of the plant diseases that may be controlled by the methods described herein include diseases caused by phytopathogenic fungi (in particular of the classes of *Ascomycetes, Deuteromycetes, Oomycetes* and *Basidiomycetes*) such as *Magnaporthe grisea, Cochliobolus miyabeanus, Rhizoctonia solani* and *Gibberella fujikuroi* on rice; *Erysiphe graminis, Fusarium graminearum, F. avenacerum, F. culmorum, Microdochium nivale, Puccinia striiformis, P. graminis, P. recondita, P. hordei, Typhula* sp., *Micronectriella nivalis, Ustilago tritici, U. nuda, Tilletia caries, Pseudocercosporella herpotrichoides, Rhynchosporium secalis, Septoria tritici, Leptosphaeria nodorum* and *Pyrenophora teres* on wheat and barley; *Diaporthe citri, Elsinoe fawcetti, Penicillium digitatum, P. italicum, Phytophthora parasitica* and *Phytophthora citrophthora* on citrus; *Monilinia mali, Valsa ceratosperma, Podosphaera leucotricha, Alternaria alternata* apple pathotype, *Venturia inaequalis, Colletotrichum acutatum* and *Phytoptora cactorum* on apple; *Venturia nashicola, V. pirina, Alternaria alternata* Japanese pear pathotype, *Gymnosporangium haraeanum* and *Phytophthora cactorum* on pear; *Monilinia fructicola, Cladosporium carpophilum* and *Phomopsis* sp. on peach; *Elsi-*

*noe ampelina, Glomerella cingulata, Uncinula necator, Phakopsora ampelopsidis, Guignardia bidwellii* and *Plasmopara viticola* on grape; *Gloeosporium kaki, Cercospora kaki* and *Mycosphaerella nawae* on persimmon; *Colletotrichum lagenarium, Sphaerotheca fuliginea, Mycosphaerella melonis, Fusarium oxysporum, Pseudoperonospora cubensis* and *Phytophthora* sp. on *Cucurbitales* vegetables; *Alternaria solani, Cladosporium fulvum* and *Phytophthora infestans* on tomato; *Phomopsis vexans* and *Erysiphe cichoracearum* on eggplant; *Alternaria japonica, Cercosporella brassicae, Plasmodiophora brassicae* and *Peronospora parasitica* on *Brassicaceae* vegetables; *Puccinia allii* and *Peronospora destructor* on leek; *Cercospora kikuchii, Elsinoe glycines, Diaporthe phaseolorum* var. *sojae, Phakopsora pachyrhizi* and *Phytophthora sojae* on soybean; *Colletotrichum lindemuthianum* of kidney bean; *Cercospora personata, Cercospora arachidicola* and *Sclerotium rolfsii* on peanut; *Erysiphe pisi* on pea; *Alternaria solani, Phytophthora infestans, Phytophthora erythroseptica* and *Spongospora subterranean* f. sp. *subterranean* on potato; *Sphaerotheca humuli* and *Glomerella cingulata* on strawberry; *Exobasidium reticulatum, Elsinoe leucospila, Pestalotiopsis* sp. and *Colletotrichum theae-sinensis* on tea; *Alternaria longipes, Erysiphe cichoracearum, Colletotrichum tabacum, Peronospora tabacina* and *Phytophthora nicotianae* on tobacco; *Cercospora beticola, Thanatephorus cucumeris,* and *Aphanidermatum cochlioides* on sugar beet; *Diplocarpon rosae, Sphaerotheca pannosa* and *Peronospora sparsa* on rose; *Bremia lactucae, Septoria chrysanthemi-indici* and *Puccinia horiana* on chrysanthemum and *Compositae* vegetables; *Alternaria brassicicola* on radish; *Sclerotinia homeocarpa* and *Rhizoctonia solani* on turf; *Mycosphaerella fijiensis* and *Mycosphaerella musicola* on banana; *Plasmopara halstedii* on sunflower; and various diseases on crops caused by *Aspergillus* spp., *Alternaria* spp., *Cephalosporium* spp., *Cercospora* spp., *Cochliobolus* spp., *Diaporthe* spp., *Phomopsis* spp., *Diplodia* spp., *Fusarium* spp., *Gibberella* spp., *Helminthosporium* spp., *Phakopsora* spp., *Phytophthora* spp., *Blumeria* spp., *Oidium* spp., *Erysiphe* spp., *Uncinula* spp., *Podosphaera* spp., *Microsphaera* spp., *Colletotrichum* spp., *Corynespora* spp., *Peronospora* spp., *Plasmopara* spp., *Pythium* spp., *Pyrenophora* spp., *Pythium* spp., *Rhizoctonia* spp., *Rhynchosporium* spp., *Botryotinia* spp., *Botrytis* spp., *Botryosphaeria* spp., *Sphaerotheca* spp., *Septoria* spp., *Thielaviopsis* spp., *Typhula* spp., *Pseudocercosporella* spp., *Cochliobolus* spp., *Gaeumannomyces* spp., *Mucor* spp., *Puccinia* spp., *Tilletia* spp., *Ustilago* spp., *Venturia* spp., *Gymnosporangium* spp., *Claviceps* spp., *Cladosporium* spp., *Physalospora* spp., *Pyricularia* spp., *Magnaporthe* spp., *Rhizopus* spp., *Monilinia* spp., *Cladosporium* spp., *Curvularia* spp., *Sclerotinia* spp., *Sclerotium* sp., *Corticum* spp., *Corticium* spp., *Phoma* spp., *Polymyxa* spp., and *Olpidium* spp.

Application to Plants and/or Soil

Generally, the methods described herein can be used to modulate, inhibit or eradicate fungal pathogens as described herein that cause disease on various parts of agricultural crop plants (e.g., fruit, blossoms, leaves, stems, tubers, roots) or other useful plants as described herein. For example, the methods described herein may be used to modulate, inhibit, and/or control any of the fungal pathogens and/or plant diseases listed above.

For example, methods described herein may be used to modulate, inhibit or eradicate plant fungal pathogens in vegetable crops, row crops, trees, nuts, vines, turf, and ornamental plants.

In some embodiments, a composition comprising a compound as described herein may be supplied to a plant exogenously. The composition may be applied to the plant and/or the surrounding soil through sprays, drips, and/or other forms of liquid application.

The compounds described herein may penetrate the plant through the roots via the soil (systemic action); by drenching the locus of the plant with a liquid composition; or by applying the compounds in solid form to the soil, e.g. in granular form (soil application).

As used herein, the term "locus" broadly encompasses the fields on which the treated plants are growing, or where the seeds of cultivated plants are sown, or the place where the seed will be placed into the soil.

For example, in some embodiments, a composition is applied to a plant, including plant leaves, shoots, roots, or seeds. In one embodiment, a composition comprising a compound as described herein applied to a foliar surface of a plant. Foliar applications may require 50 to 500 g per hectare of a compound as described herein.

As used herein, the term "foliar surface" broadly refers to any green portion of a plant having surface that may permit absorption of silicon, including petioles, stipules, stems, bracts, flowerbuds, and leaves. Absorption commonly occurs at the site of application on a foliar surface, but in some cases, the applied composition may run down to other areas and be absorbed there.

Compositions described herein can be applied to the foliar surfaces of the plant using any conventional system for applying liquids to a foliar surface. For example, in some embodiments, application by spraying will be found most convenient. Any conventional atomization method can be used to generate spray droplets, including hydraulic nozzles and rotating disk atomizers. In some embodiments, alternative application techniques, including application by brush or by rope-wick, may be utilized.

In some embodiments, a composition comprising a compound as described herein is directly applied to the soil surrounding the root zone of a plant. Soil applications may require 0.5 to 5 kg per hectare of a compound as described herein on a broadcast basis (rate per treated area if broadcast or banded).

For example, in some embodiments, a composition may be applied directly to the base of the plants or to the soil immediately adjacent to the plants.

In some embodiments, a sufficient quantity of the composition is applied such that it drains through the soil to the root area of the plants.

Generally, application of a composition may be performed using any method or apparatus known in the art, including but not limited to hand sprayer, mechanical sprinkler, or irrigation, including drip irrigation.

In some embodiments, a composition is applied to plants and/or soil using a drip irrigation technique. For example, the composition may be applied through existing drip irrigation systems. This procedure is used in some embodiments in connection with cotton, strawberries, tomatoes, potatoes, vegetables, and ornamental plants.

In other embodiments, a composition is applied to plants and/or soil using a drench application. The drench application technique is used in some embodiments in connection with crop plants and turf grasses.

In some embodiments, a composition is applied to soil after planting. In other embodiments, however, a composition may be applied to soil during planting, or a composition may be applied to soil before planting.

For example, in some embodiments, a composition may be tilled into the soil or applied in furrow.

In crops of water, such as rice, solid granulates comprising the compounds described herein may be applied to the flooded field or locus of the crop plants to be treated.

Application to Seeds

One embodiment of the disclosure is generally related to a method of protecting a seed, and/or the roots of a plant grown from the seed, against damage by phytopathogenic fungi. The seed treatment methods described herein may be used to modulate, inhibit, and/or control any of the fungal pathogens and/or plant diseases described above. In one embodiment, the method comprises treating a seed with a composition comprising a compound as described herein. As used herein, the term "seed" broadly encompasses plant propagating material such as, tubers cuttings, seedlings, seeds, and germinated or soaked seeds.

In one embodiment, the disclosure relates to a method of administering to a seed a compound (e.g., a compound of Formula I, Ia, Ib, II, IIa, or IIb) as described to control fungal pathogens in a composition as described herein, including using the compounds as described herein with the any adjuvants, excipients, or other desirable components as described herein or known in the art and formulating, mixing, or combining one or more additional active ingredients. The additional active ingredient may be, for example, an additional pesticide. The pesticide may be, for example, an insecticide, a fungicide, an herbicide, or an additional nematicide as described herein or otherwise known in the art.

For example, a compound as described herein may be applied to seeds or tubers by impregnating them with a liquid seed treatment composition comprising a compound described herein, or by coating them with a solid or liquid composition comprising a compound described herein.

Seed treatment methods described herein can be used in connection with any species of plant and/or the seeds thereof as described herein. In some embodiments, however, the methods are used in connection with seeds of plant species that are agronomically important. In particular, the seeds can be of corn, peanut, canola/rapeseed, soybean, cucurbits, crucifers, cotton, beets, rice, sorghum, sugar beet, wheat, barley, rye, sunflower, tomato, sugarcane, tobacco, oats, as well as other vegetable and leaf crops. In some embodiments, the seed is corn, soybean, or cotton seed. The seed may be a transgenic seed from which a transgenic plant can grow and incorporate a transgenic event that confers, for example, tolerance to a particular herbicide or combination of herbicides, insect resistance, increased disease resistance, enhanced tolerance to stress and/or enhanced yield. Transgenic seeds include, but are not limited to, seeds of corn, soybean and cotton.

A seed treatment method may comprise applying the seed treatment composition to the seed prior to sowing the seed, so that the sowing operation is simplified. In this manner, seeds can be treated, for example, at a central location and then dispersed for planting. This permits the person who plants the seeds to avoid the complexity and effort associated with handling and applying the compositions, and to merely handle and plant the treated seeds in a manner that is conventional for regular untreated seeds.

A composition can be applied to seeds by any standard seed treatment methodology, including but not limited to mixing in a container (e.g., a bottle or bag), mechanical application, tumbling, spraying, immersion, and solid matrix priming. Seed coating methods and apparatus for their application are disclosed in, for example, U.S. Pat. Nos. 5,918,413; 5,891,246; 5,554,445; 5,389,399; 5,107,787; 5,080,925; 4,759,945 and 4,465,017, among others. Any conventional active or inert material can be used for contacting seeds with the composition, such as conventional film-coating materials including but not limited to water-based film coating materials.

For example, in one embodiment, a composition can be introduced onto or into a seed by use of solid matrix priming. For example, a quantity of the composition can be mixed with a solid matrix material and then the seed can be placed into contact with the solid matrix material for a period to allow the composition to be introduced to the seed. The seed can then optionally be separated from the solid matrix material and stored or used, or the mixture of solid matrix material plus seed can be stored or planted directly. Non-limiting examples of solid matrix materials which are useful include polyacrylamide, starch, clay, silica, alumina, soil, sand, polyurea, polyacrylate, or any other material capable of absorbing or adsorbing the composition for a time and releasing the active compound of the composition into or onto the seed. It is useful to make sure that the active compound and the solid matrix material are compatible with each other. For example, the solid matrix material should be chosen so that it can release the active compound at a reasonable rate, for example over a period of minutes, hours, days, or weeks.

Imbibition is another method of treating seed with the composition. For example, a plant seed can be directly immersed for a period of time in the composition. During the period that the seed is immersed, the seed takes up, or imbibes, a portion of the composition. Optionally, the mixture of plant seed and the composition can be agitated, for example by shaking, rolling, tumbling, or other means. After imbibition, the seed can be separated from the composition and optionally dried, for example by patting or air drying.

A composition may be applied to the seeds using conventional coating techniques and machines, such as fluidized bed techniques, the roller mill method, rotostatic seed treaters, and drum coaters. Other methods, such as spouted beds may also be useful. The seeds may be pre-sized before coating. After coating, the seeds may be dried and then transferred to a sizing machine for sizing. Such procedures are generally known in the art.

If a composition is applied to the seed in the form of a coating, the seeds can be coated using a variety of methods known in the art. For example, the coating process can comprise spraying the composition onto the seed while agitating the seed in an appropriate piece of equipment such as a tumbler or a pan granulator.

In one embodiment, when coating seed on a large scale (for example a commercial scale), the seed coating may be applied using a continuous process. For example, seed may be introduced into the treatment equipment (such as a tumbler, a mixer, or a pan granulator) either by weight or by flow rate. The amount of treatment composition that is introduced into the treatment equipment can vary depending on the seed weight to be coated, surface area of the seed, the concentration of the fungicide and/or other active ingredients in a composition, the desired concentration on the finished seed, and the like. A composition can be applied to the seed by a variety of means, for example by a spray nozzle or revolving disc. The amount of liquid may be determined by the assay of the formulation and the required rate of active ingredient necessary for efficacy. As the seed falls into the treatment equipment the seed can be treated (for example by misting or spraying with the composition)

and passed through the treater under continual movement/ tumbling where it can be coated evenly and dried before storage or use.

In another embodiment, the seed coating may be applied using a batch process. For example, a known weight of seeds can be introduced into the treatment equipment (such as a tumbler, a mixer, or a pan granulator). A known volume of the composition can be introduced into the treatment equipment at a rate that allows the composition to be applied evenly over the seeds. During the application, the seed can be mixed, for example by spinning or tumbling. The seed can optionally be dried or partially dried during the tumbling operation. After complete coating, the treated sample can be removed to an area for further drying or additional processing, use, or storage.

In an alternative embodiment, the seed coating may be applied using a semi-batch process that incorporates features from each of the batch process and continuous process embodiments set forth above.

In still another embodiment, seeds can be coated in laboratory size commercial treatment equipment such as a tumbler, a mixer, or a pan granulator by introducing a known weight of seeds in the treater, adding the desired amount of the composition, tumbling or spinning the seed and placing it on a tray to thoroughly dry.

In another embodiment, seeds can also be coated by placing the known amount of seed into a narrow neck bottle or receptacle with a lid. While tumbling, the desired amount of the composition can be added to the receptacle. The seed is tumbled until it is coated with the composition. After coating, the seed can optionally be dried, for example on a tray.

In some embodiments, the treated seeds may also be enveloped with a film overcoating to protect the fungicidal coating. Such overcoatings are known in the art and may be applied using conventional fluidized bed and drum film coating techniques. The overcoatings may be applied to seeds that have been treated with any of the seed treatment techniques described above, including but not limited to solid matrix priming, imbibition, coating, and spraying, or by any other seed treatment technique known in the art.

Treated Seeds

In one embodiment the disclosure is generally related to a seed that has been treated with a composition as described herein comprising a compound (e.g., a compound of Formula I, Ia, Ib, II, IIa, or IIb) as described herein. In some embodiments, the seed has been treated with the composition using one of the seed treatment methods set forth above, including but not limited to solid matrix priming, imbibition, coating, and spraying. The treated seed may be of any plant species, as described above. In other embodiments, a seed is treated with a composition as described herein, including formulating, mixing in a seed treater tank, or combining on a seed by overcoating one or more additional active ingredients. The additional active ingredient may be, for example, an additional pesticide. The pesticide may be, for example, an insecticide, a fungicide, an herbicide, or an additional nematicide as described herein.

The amount of a compound present on a treated seed sufficient to protect the seed, and/or the roots of a plant grown from the seed, against damage by phytopathogenic fungi can be readily determined by one of ordinary skill in the art. In an embodiment, treated seeds comprise a compound of Formula I, Ia, Ib, II, IIa, or IIb in an amount of at least about 0.005 mg/seed. In another embodiment, treated seeds comprise a compound of Formula I, Ia, Ib, II, IIa, or IIb in an amount of from about 0.005 to about 2 mg/seed, or from about 0.005 to about 1 mg/seed.

Administration

In some embodiments, a compound (e.g., a compound of Formula I, Ia, Ib, II, IIa, or IIb) as described herein is used as a ACCase modulator. For example, in some embodiments, the present disclosure is directed to a method of modulating acetyl-CoA carboxylase (ACCase) in a biological organisim, wherein the method comprises administering to the biological organism a composition comprising an effective amount of a compound.

In some embodiments, the biological organism is an animal. For example, in some embodiments, the biological organism is a warm-blooded animal. In some embodiments, the biological organism is a mammal, including, for example, humans.

A compound described herein may generally be formulated in a composition comprising one or more biologically acceptable excipients and, optionally, another pharmaceutically active agent known to those skilled in the art.

Any suitable dosage may be administered. The compound or salt thereof chosen for a particular application, the carrier and the amount will vary widely depending on the species of the warm blooded animal or human or the particular disease condition being treated, and depending upon the effective modulatory concentrations observed in trial studies. The dosage administered will, of course, vary depending upon known factors, such as the pharmacodynamic characteristics of the particular compound or salt thereof and its mode and route of administration; the age, health, or weight of the subject; the nature and extent of symptoms; the metabolic characteristics of the composition and patient, the kind of concurrent treatment; the frequency of treatment; or the effect desired.

A dosage unit may comprise a single compound, or mixtures thereof, with other compounds. The dosage unit may comprise diluents, extenders, carriers, liposomes, or the like. The unit may be in solid or gel form such as pills, tablets, capsules and the like or in liquid form suitable for oral, rectal, topical, intravenous injection or parenteral administration or injection into or around the treatment site.

Having described the disclosure in detail, it will be apparent that modifications and variations are possible without departing from the scope of the claims.

EXAMPLES

The following non-limiting examples are provided for further illustration.

Example 1

ACCase Enzymatic Assay

Ustilago maydis acetyl CoA carboxylase (ACCase) was cloned, expressed, and purified as described (Weatherly et al, Biochem. J., 2004) and the test compounds were tested in a 96-well plate format. Primary in vitro screening consisted of obtaining dose response data at 100, 33, 10, and 1 µM inhibitor. Actives in the primary screen were re-tested to establish IC50 values.

Direct detection of the conversion of acetyl CoA to malonyl CoA by ACCase was not feasible, but during this process ATP is converted to ADP which allowed for detection through a standard reaction coupling with ADP recycling to the oxidation of NADH. Thus, ACCase activity was measured via kinetic OD340 measurements of the conversion of NADH to NAD in a coupled reaction involving the conversion of phosphoenolpyruvate (PEP) to lactate.

The complete 200 ul reaction mixture contained 52.5 mM HEPES (pH8), 2.625 mM $MgCl_2$, 1 mM ATP, 0.525 mM DTT, 11 mM $NaHCO_3$, 1% DMSO with or without inhibitor, 1× pyruvate kinase/lactate dehydrogenase (PK/LDH), 0.3 mM NADH, 0.5 mM PEP, and 5 μg ACCase. The reactions were incubated at 30° C. for 10 minutes and then initiated by the addition of 0.33 mM acetyl CoA. The initiated reactions were read immediately via plate reader at OD340 and kinetic readings were acquired every 20 s for 15 minutes while keeping the temperature at 30° C.

A slope of the kinetic curve was determined by using the 2 to 7 minute data which was then calculated as percent inhibition relative to the no inhibitor control.

The primary screens were conducted in duplicate and the IC50's conducted in triplicate. Averages were reported along with standard deviation calculation to generate error bars.

Each plate contained its own controls and consisted of a DMSO only control, 5-fold titration series of soraphen from 2 μM to 3.2 nM, and an ADP coupled reaction control.

In order to effectively screen out non-specific modulators of pyruvate kinase and lactate dehydrogenase (the coupled portion of the reaction), a PK/LDH inhibition test was developed. The complete 200 μl reaction mixture contained 52.5 mM HEPES (pH8), 2.625 mM $MgCl_2$, 0.525 mM DTT, 11 mM $NaHCO_3$, 1% DMSO with or without inhibitor, 1× pyruvate kinase/lactate dehydrogenase (PK/LDH), 0.3 mM NADH, and 0.5 mM PEP. The reactions were incubated at 30° C. for 10 minutes and then initiated by the addition of 66 μM ADP. The initiated reactions were read immediately via plate reader at OD340 and kinetic readings were acquired every 20 s for 15 minutes while remaining at 30° C.

A slope of the kinetic curve was determined by using the 2 to 7 minute data which was then calculated as percent inhibition relative to the no inhibitor control. Those compounds which had no significant PK/LDH inhibition at or above the IC50 in the ACCase assay, were considered to be valid modulators of only ACCase. The IC50 data for compounds of Formulas I and II are shown in Table 1A below.

TABLE 1A

ACCase Inhibitory Activity

| Formula | Name | Structure | IC50 (μM) |
|---|---|---|---|
| Ia-i | 2-((4-(4-chlorophenyl)-3-cyano-6-(thiophen-2-yl)pyridine-2-yl)thio)-2-phenylacetic acid | 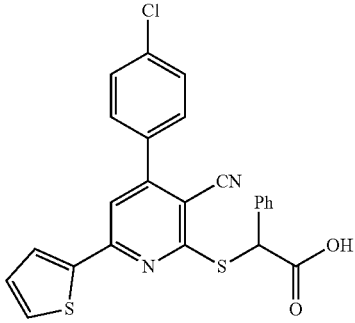 [SMILES: N#Cc1c(-c2ccc(Cl)cc2)cc(-c2cccs2)nc1SC(C(=O)O)c1ccccc1] | 0.370[a] |
| Ia-ii | 2-((3-cyano-6-(thiophen-2-yl)-4-(trifluoromethyl)pyridin-2-yl)thio)-2-phenylacetic acid | 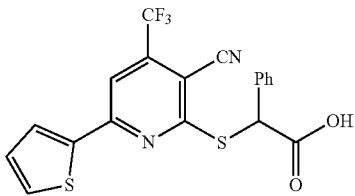 | 2.015[a] |
| Ia-iii | 2-((3-cyano-4,6-di(thiophen-2-yl)pyridin-2-yl)thio)-2-phenylacetic acid | 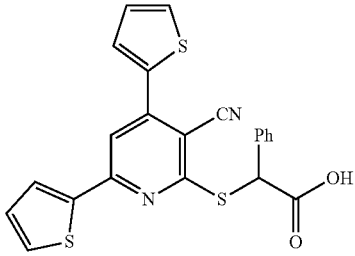 [SMILES: N#Cc1c(-c2cccs2)cc(-c2cccs2)nc1SC(C(=O)O)c1ccccc1] | 0.616[a] |

TABLE 1A-continued

ACCase Inhibitory Activity

| Formula | Name | Structure | IC50 (μM) |
|---|---|---|---|
| Ia-iv | 2-((3-cyano-4-phenyl-6-(thiophen-2-yl)pyridin-2-yl)thio)-2-phenylacetic acid | 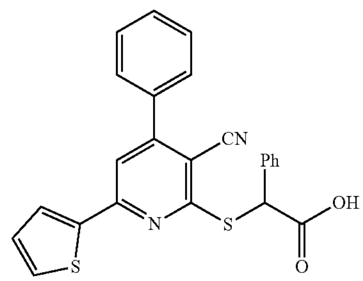 [SMILES: N#Cc1c(-c2ccccc2)cc(-c2cccs2)nc1SC(C(=O)O)c1ccccc1] | 0.492[a] |
| Ia-v | 2-((3-cyano-4-(4-methoxyphenyl)-6-(thiophen-2-yl)pyridin-2-yl)thio)-2-phenylacetic acid | 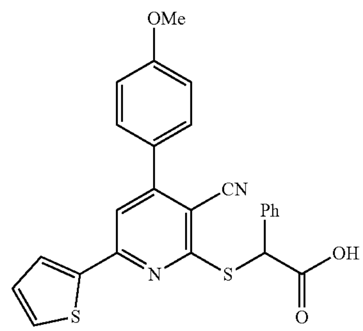 [SMILES: COc1ccc(-c2cc(-c3cccs3)nc(SC(C(=O)O)c3ccccc3)c2C#N)cc1] | 0.119 |
| Ia-vi | 2-((3-cyano-8-methyl-4-(thiophen-2-yl)-5,6,7,8-tetrahydro-1,8-naphthyridin-2-yl)thio)-2-phenylacetic acid | 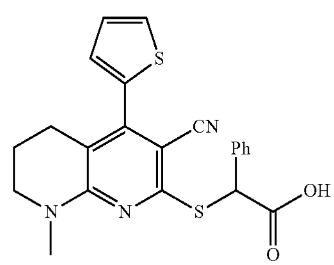 [SMILES: CN1CCCc2c1nc(SC(C(=O)O)c1ccccc1)c(C#N)c2-c1cccs1] | 3.549 |
| Ia-vii | 2-((4-cyano-1-(thiophen-2-yl)-5,6,7,8-tetrahydroisoquinolin-3-yl)thio)-2-phenylacetic acid | 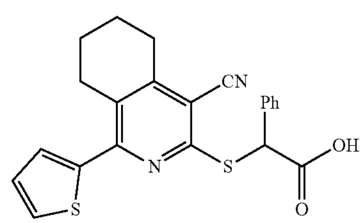 [SMILES: N#Cc1c(SC(C(=O)O)c2ccccc2)nc(-c2cccs2)c2c1CCCC2] | 3.805 |
| Ia-viii | 2-((3-cyano-6-(2,4-dimethoxyphenyl)-4-(trifluoromethyl)pyridin-2-yl)thio)-2-phenylacetic acid | 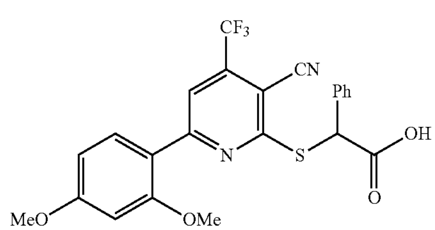 [SMILES: COc1ccc(-c2cc(C(F)(F)F)c(C#N)c(SC(C(=O)O)c3ccccc3)n2)c(OC)c1] | 1.718 |

TABLE 1A-continued

ACCase Inhibitory Activity

| Formula | Name | Structure | IC50 (μM) |
|---|---|---|---|
| Ia-ix | 2-((3-cyano-6-(3,4-dimethoxyphenyl)-4-(trifluoromethyl)pyridin-2-yl)thio)-2-phenylacetic acid | 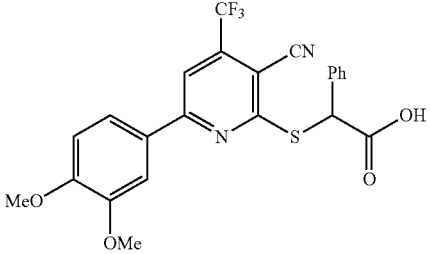 [SMILES: COc1ccc(-c2cc(C(F)(F)F)c(C#N)c(SC(C(=O)O)c3ccccc3)n2)cc1OC] | 1.600 |
| Ia-x | 2-((6-(4-bromophenyl)-3-cyano-4-(trifluoromethyl)pyridin-2-yl)thio)-2-phenylacetic acid | 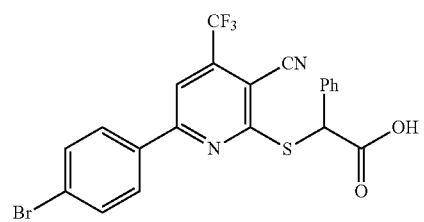 [SMILES: N#Cc1c(C(F)(F)F)cc(-c2ccc(Br)cc2)nc1SC(C(=O)O)c1ccccc1] | 1.946 |
| Ia-xi | 2-((3-cyano-6-(furan-2-yl)-4-(trifluoromethyl)pyridin-2-yl)thio)-2-phenylacetic acid | 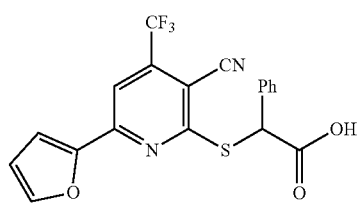 | 5.432 |
| Ia-xii | 2-((3-cyano-4,6-diphenylpyridin-2-yl)thio)-2-phenylacetic acid | 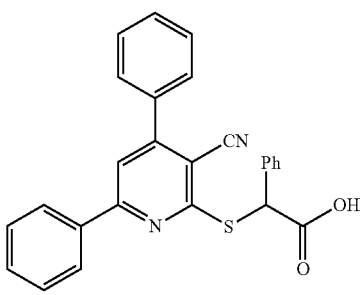 [SMILES: N#Cc1c(-c2ccccc2)cc(-c2ccccc2)nc1SC(C(=O)O)c1ccccc1] | 0.266 |
| Ia-xiii | 2-((3-cyano-4-(thiophen-2-yl)-5,6,7,8-tetrahydroquinolin-2-yl)thio)-2-phenylacetic acid | 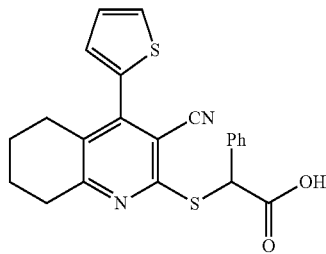 [SMILES: N#Cc1c(SC(C(=O)O)c2ccccc2)nc2c(c1-c1cccs1)CCCC2] | 0.274 |

TABLE 1A-continued

ACCase Inhibitory Activity

| Formula | Name | Structure | IC50 (μM) |
|---|---|---|---|
| Ia-xiv | 2-((3-cyano-4-(4-methoxyphenyl)-6-(thiophen-2-yl)pyridin-2-yl)thio)-2-phenylacetic acid | 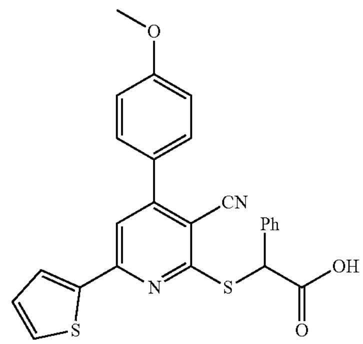 [SMILES: COc1ccc(-c2cc(-c3cccs3)nc(SC(C(=O)O)c3ccccc3)c2C#N)cc1] | 0.060 |
| Ia-xv | 2-((4-cyano-1-ethyl-5,6,7,8-tetrahydroisoquinolin-3-yl)thio)-2-phenylacetic acid | 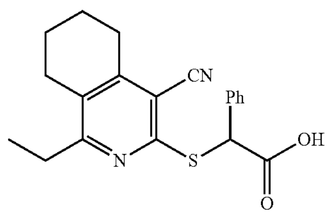 [SMILES: CCc1nc(SC(C(=O)O)c2ccccc2)c(C#N)c2c1CCCC2] | 10.24 |
| Ia-xvi | 2-((3-cyano-6-methyl-4-(trifluoromethyl)pyridin-2-yl)thio)-2-phenylacetic acid | 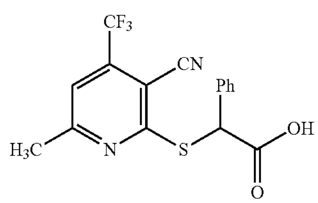 [SMILES: Cc1cc(C(F)(F)F)c(C#N)c(SC(C(=O)O)c2ccccc2)n1] | 7.729 |
| Ia-xvii | 2-((3-cyano-4-phenyl-5,6,7,8-tetrahydroquinolin-2-yl)thio)-2-phenylacetic acid | 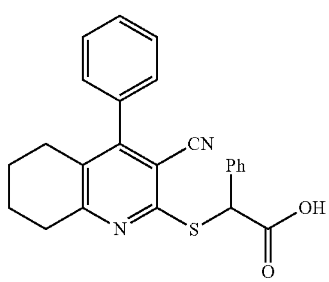 [SMILES: N#Cc1c(SC(C(=O)O)c2ccccc2)nc2c(c1-c1ccccc1)CCCC2] | 0.906 |
| Ia-xviii | 2-((4-(4-chlorophenyl)-3-cyano-5,6,7,8-tetrahydronaphthalen-2-yl)thio)-2-phenylacetic acid | 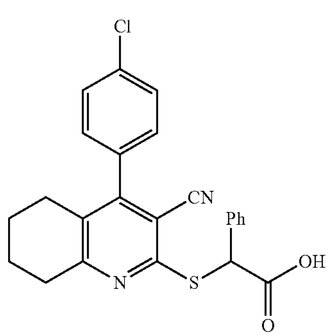 [SMILES: N#Cc1c(SC(C(=O)O)c2ccccc2)nc2c(c1-c1ccc(Cl)cc1)CCCC2] | 1.385 |

TABLE 1A-continued

ACCase Inhibitory Activity

| Formula | Name | Structure | IC50 (μM) |
|---|---|---|---|
| Ia-xix | 2-((4-(4-methoxypheny)-6-(thiophen-2-yl)pyridin-2-yl)thio)-2-phenylacetic acid | 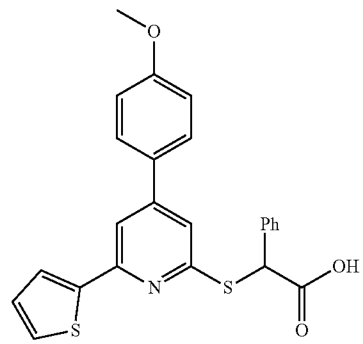 [SMILES: COc1ccc(-c2cc(SC(C(=O)O)c3ccccc3)nc(-c3cccs3)c2)cc1] | 9.059 |
| Ia-xx | 2-((3-cyano-6-(furan-2-yl)-4-(4-methoxyphenyl)pyridin-2-yl)thio)-2-phenylacetic acid | 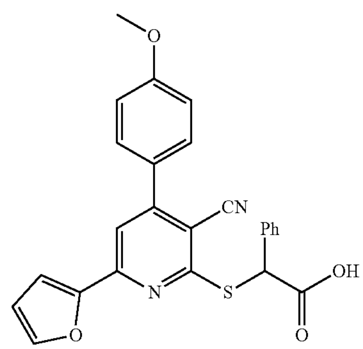 | 0.345 |
| Ia-xxi | 2-((3-cyano-6-(thiophen-2-yl)-4-(p-tolyl)pyridin-2-yl)thio)-2-phenylacetic acid | 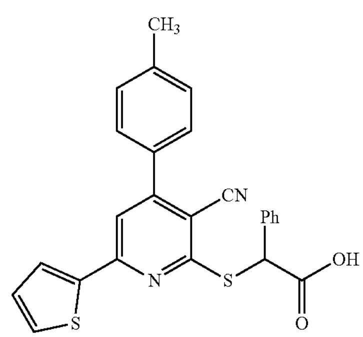 [SMILES: Cc1ccc(-c2cc(-c3cccs3)nc(SC(C(=O)O)c3ccccc3)c2C#N)cc1] | 0.353 |
| Ia-xxii | 2-((3-cyano-4-(4-fluorophenyl)-6-(thiophen-2-yl)pyridin-2-yl)thio)-2-phenylacetic acid | 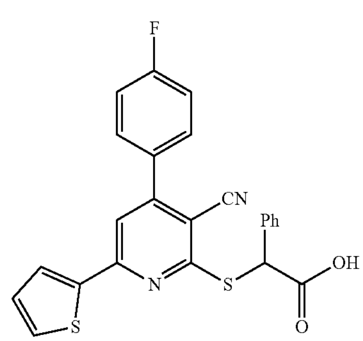 [SMILES: N#Cc1c(-c2ccc(F)cc2)cc(-c2cccs2)nc1SC(C(=O)O)c1ccccc1] | 0.563 |

TABLE 1A-continued

ACCase Inhibitory Activity

| Formula | Name | Structure | IC50 (μM) |
| --- | --- | --- | --- |
| Ia-xxiii | 2-((4-(4-bromophenyl)-3-cyano-6-(thiophen-2-yl)pyridin-2-yl)thio)-2-phenylacetic acid | 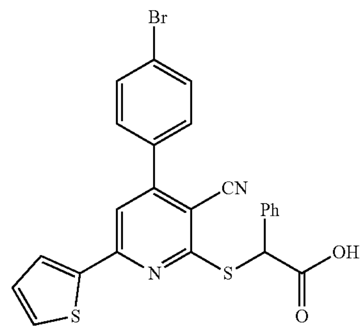 [SMILES: N#Cc1c(-c2ccc(Br)cc2)cc(-c2cccs2)nc1SC(C(=O)O)c1ccccc1] | 0.212 |
| Ia-xxiv | 2-((3-cyano-6-(furan-2-yl)-4-(thiophen-2-yl)pyridin-2-yl)thio)-2-phenylacetic acid | 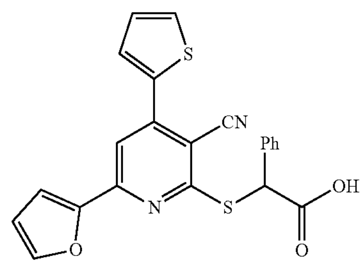 [SMILES: N#Cc1c(-c2cccs2)cc(-c2ccco2)nc1SC(C(=O)O)c1ccccc1] | 0.958 |
| Ia-xxv | 2-((3-cyano-4,6-di(furan-2-yl)pyridin-2-yl)thio)-2-phenylacetic acid | 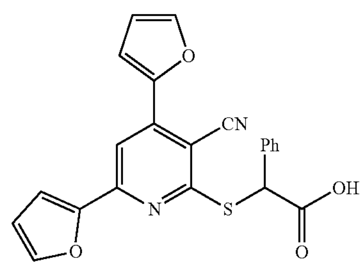 [SMILES: N#Cc1c(-c2ccco2)cc(-c2ccco2)nc1SC(C(=O)O)c1ccccc1] | 4.035 |
| Ia-xxvi | 2-((3-cyano-4-(4-methoxyphenyl)-5,6,7,8-tetrahydroquinolin-2-yl)thio)-2-phenylacetic acid | 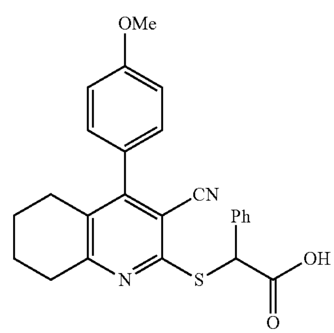 [SMILES: COc1ccc(-c2c(C#N)c(SC(C(=O)O)c3ccccc3)nc3c2CCCC3)cc1] | 0.56 |
| Ia-xxvii | 2-((3-cyano-4-(thiophen-2-yl)-5,6,7,8-tetrahydroquinolin-2-yl)oxy)-2-phenylacetic acid | 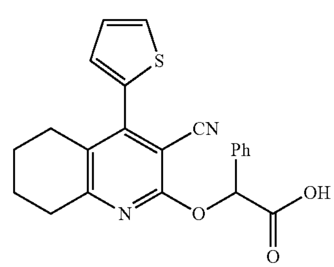 [SMILES: N#Cc1c(OC(C(=O)O)c2ccccc2)nc2c(c1-c1cccs1)CCCC2] | 0.249 |

TABLE 1A-continued

ACCase Inhibitory Activity

| Formula | Name | Structure | IC50 (μM) |
| --- | --- | --- | --- |
| Ia-xxviii | 2-((3-cyano-4-(4-methoxyphenyl)-6-(1-oxidothiophen-2-yl)pyridin-2-yl)oxy)-2-phenylacetic acid | 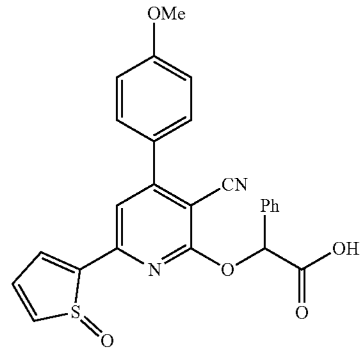 [SMILES: COc1ccc(-c2cc(C3=CC=CS3=O)nc(OC(C(=O)O)c3ccccc3)c2C#N)cc1] | 0.196 |
| Ia-xxix | 2-((3-cyano-4-(4-methoxyphenyl)-6-(thiophen-2-yl)pyridin-2-yl)thio)butanoic acid | 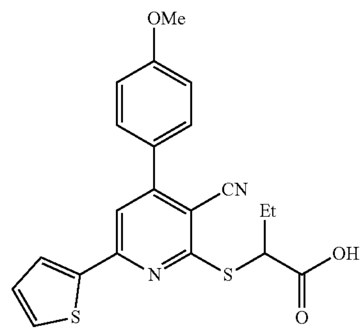 [SMILES: CCC(Sc1nc(-c2cccs2)cc(-c2ccc(OC)cc2)c1C#N)C(=O)O] | 0.113 |
| Ib-i | 2-((3-cyano-4-(thiophen-2-yl)-5,6,7,8-tetrahydroquinolin-2-yl)thio)-2-phenylacetamide | 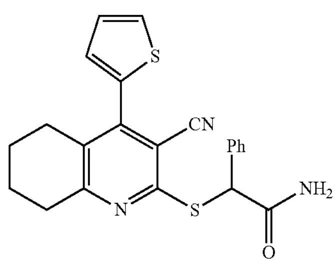 [SMILES: N#Cc1c(SC(C(N)=O)c2ccccc2)nc2c(c1-c1cccs1)CCCC2] | 0.712 |
| Ib-ii | 2-((3-cyano-4-(4-methoxyphenyl)-6-(thiophen-2-yl)pyridin-2-yl)thio)-2-phenylacetamide | 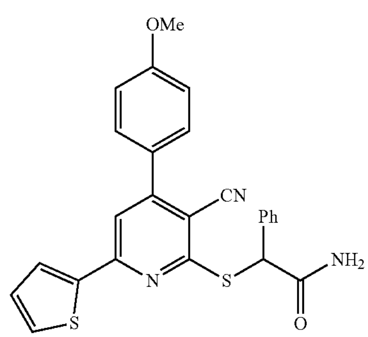 [SMILES: COc1ccc(-c2cc(-c3cccs3)nc(SC(C(N)=O)c3ccccc3)c2C#N)cc1] | >33 |

TABLE 1A-continued

ACCase Inhibitory Activity

| Formula | Name | Structure | IC50 (μM) |
|---|---|---|---|
| Ib-iii | 2-((3-cyano-4-(4-methoxyphenyl)-6-(thiophen-2-yl)pyridin-2-yl)thio)-N-hydroxy-2-phenylacetamide | (structure) | 0.882 |
| IIb-i | 2-((2-hydroxy-1-phenylethyl)thio)-4-(4-methoxyphenyl)-6-(thiophen-2-yl)nicotinonitrile | (structure) | 0.625 |
| IIb-ii | 2-((2-hydroxy-1-phenylethyl)thio)-4-(thiophen-2-yl)-5,6,7,8-tetrahydroquinoline-3-carbonitrile | (structure) | 4.093 |
| IIb-iv | 4-(furan-2-yl)-2-((2-hydroxy-1-phenylethyl)thio)-6-(thiophen-2-yl)nicotinonitrile | (structure) | 2.184 |
| | Soraphen | | 0.0458[a] |

[a]IC50 values are a result of two or more experiments

TABLE 1B

ACCase Inhibitory Activity of Racemic Mixtures and Single Enantiomers

| Formula | Name | Retention Time | IC50 (μM) |
|---|---|---|---|
| Ia-ii | racemate | | 2.02 |
| Ia-ii-e1 | enantiomer 1* | 9.75 min | 12.86 |
| Ia-ii-e2 | enantiomer 2 | 7.89 min | 1.208 |
| Ia-iii | racemate | | 0.439 |
| Ia-iii-e1 | enantiomer 1* | 14.87 min | 0.547 |
| Ia-iii-e2 | enantiomer 2 | 18.51 min | 2.39 |
| Ia-xiv | racemate | | 0.092; 0.14 |
| Ia-xiv-e1 | enantiomer 1* | 15.64 min | 0.115; 0.129 |
| Ia-xiv-e2 | enantiomer 2 | 18.13 min | 0.44; 0.523 |

*More active enantiomer with a shorter retention time on the analytical Chiralpak IC column

Example 2

Fungal Growth Inhibition Assay

Spores were isolated from previously sub-cultured plates of *Botrytis cinerea, Phytophthora capsici, Fusarium moniliforme, Fusarium viguliforme, Collectotrichum graminicola,* and *Diplodia maydis.* All spores were filtered and collected in a sterile glass bowl to isolate the spores from the mycelia. The isolation and sub-culture plate condition for each pathogen is described below.

Spore isolation for *B. cinerea:* A 2-3 week old V8 (17%)+$CaCO_3$ (3 g/L)+20 g agar plate was removed from room temperature and the mycelia were treated with 5-10 ml of filter sterilized Triton X 100 (.05%). The mycelia were scraped to re-suspend the spores. The spores were then collected in a sterile filter bowl containing a fluted piece of filter paper and poured into a conical tube.

Spore isolation for *F. moniliforme:* A 1 week old PDA (potato dextrose agar, pre-mix) plate was removed from 26° C. incubator with a light/dark 12 hour cycle and the mycelia were treated with 5-10 ml of filter sterilized Triton X 100 (0.05%). The mycelia were scraped to re-suspend the spores. The spores were then collected in a sterile filter bowl containing a fluted piece of filter paper.

Spore isolation for *C. graminicola:* A 1-2 week old oatmeal agar (pre-mix) plate was removed from 26° C. incubator with a light/dark 12 hour cycle and the mycelia were treated with 10-15 ml of filter sterilized distilled water. The mycelia were scraped to re-suspend the spores. The spores were then collected in a sterile filter bowl containing a piece of sterile cheesecloth and poured into a conical tube.

Spore isolation for *F. virguliforme:* A 2-3 week old PDA (pre-mix) plate containing cefotaxime (100 mg/L) and kanamycin (50 mg/L) was removed from 26° C. incubator with a light/dark 12 hour cycle and the mycelia were treated with 5-10 ml of filter sterilized distilled water. The mycelia were scraped to re-suspend the spores. The spores were then collected in a sterile filter bowl containing a fluted piece of filter paper and poured into a conical tube.

Spore isolation for *D. maydis:* A 3-4 week old PDA (pre-mix) plate was removed from 26° C. incubator with a light/dark 12 hour cycle and the mycelia were treated with 6-7 ml of sterile distilled water, scraped into a sterile petri dish, and smashed to open the pycnidia. The spores were then collected in a sterile filter bowl containing a fluted piece of filter paper and poured into a conical tube.

Spore isolation for *P. capsici:* Three to five days prior to the assay a 2-3 week old V8 (17%)+$CaCO_3$ (3 g/L)+20 g agar plate was removed from a dark 25° C. incubator and cut up into small chunks. One plate was separated into two deep well plates and rinsed with sterile distilled water three times. The cut up pieces were incubated under light in a sterile filter hood with 25 ml of sterile distilled water. On the day of the assay the water was removed and 5-7 ml of fresh sterile distilled water was added. One plate was incubated at 4° C. for 45-60 minutes and then placed at room temperature for about 45-60 minutes. The spores were collected in a sterile filter bowl containing a fluted piece of filter paper. The spores were vortexed in a conical tube for 30-60 seconds to remove the flagella of the zoospores after isolation.

After spore isolation, pathogen spores were counted on a hemocytometer to calculate the spores/ml. In 17% V8 liquid media containing 3 g/L $CaCO_3$, isolated spores were diluted to individual concentrations based on the growth curves at 48 hours of each pathogen. The spore concentrations for each pathogen were as follows: *B. cinerea*—10,000 sp/ml; *P. capsici*—300 sp/ml; *F. monliforme*—500 sp/ml; *F. virguliforme*—500 sp/ml; *C. graminicola*—3,000 sp/ml; and *D. maydis*—3,000 sp/ml.

Chemistry stocks were dissolved in DMSO at 2.5 mg/ml. Chemistry was diluted in a 96-well stock plate in five-fold dilutions to obtain a final concentration of 50, 10, and 2 ppm in vitro. The final concentration of the positive control after the five-fold dilutions was as follows: soraphen—0.5, 0.1, and 0.02 ppm. Negative controls on each plate included 2% DMSO, water containing spores and media, and a blank for background subtraction.

In a 96-well plate the spore solution, chemistries, and controls were combined to make the final solution concentrations mentioned above. Upon addition of the chemistry, an OD600 reading was done to assess chemical precipitation. The 96-well plates were incubated in plastic tubs containing wet paper towels under the following conditions, 25° C. in the dark for P. capsici and *B. cinerea* or 26° C. with light/dark cycle for *C. graminicola, D. maydis, F. virguliforme, F. monliforme.* Plate readings were repeated at 24 and 48 hrs. Visual ratings were performed at 24 and 48 hrs to check for precipitation and confirm efficacy. Visual and OD600 ratings of the chemistry at 48 hours were compared to the 2% DMSO control to determine the percent of pathogen growth inhibition.

Fungal growth inhibition data for compounds of Formula I against several fungal species are shown in Table 2A through 2E.

TABLE 2A

Fungal Growth Inhibition of *Collectotrichum graminicola*

| | *C. graminicola* % growth inhibition at 48 hours | | |
|---|---|---|---|
| Formula | 50 ppm | 10 ppm | 2 ppm |
| Ia-i | 92 | 72 | 28 |
| Ia-iii | 91 | 98 | 27 |
| Ia-iv | 76 | 41 | 5 |
| Ia-v | 79 | 32 | 0 |
| Ia-vii | 71 | 19 | 11 |
| Ia-ix | 72 | 17 | 5 |
| Ia-xii | 80 | 35 | 6 |
| Ia-xiv | 79 | 32 | 6 |

TABLE 2B

Fungal Growth Inhibition of *Diplodia maydis*

| | *D. maydis* % growth inhibition at 48 hours | | |
|---|---|---|---|
| Formula | 50 ppm | 10 ppm | 2 ppm |
| Ia-i | 65 | 57 | 3 |
| Ia-iii | 82 | 87 | 0 |
| Ia-v | 52 | 61 | 0 |
| Ia-vii | 64 | 46 | 11 |
| Ia-ix | 70 | 37 | 32 |
| Ia-xi | 82 | 54 | 38 |
| Ia-xii | 86 | 59 | 42 |
| Ia-xiii | 40 | 13 | 20 |

TABLE 2C

Fungal Growth Inhibition of Fusarium virguliforme

| Formula | F. virguliforme % growth inhibition at 48 hours | | |
|---|---|---|---|
| | 50 ppm | 10 ppm | 2 ppm |
| Ia-iii | 90 | 84 | 2 |
| Ia-xv | | 48 | 10 |

TABLE 2D

Fungal Growth Inhibition of Botrytis cinerea

| Formula | B. cinerea % growth inhibition at 48 hours | | |
|---|---|---|---|
| | 50 ppm | 10 ppm | 2 ppm |
| Ia-x | 25 | 12 | 0 |
| Ia-xii | 19 | 6 | 0 |
| Ia-xiv | | 8 | 14 |
| Ia-xxviii | | 27 | 14 |

TABLE 2E

Fungal Growth Inhibition of Phytophthora capsici

| Formula | P. capsici % growth inhibition at 48 hours | | |
|---|---|---|---|
| | 50 ppm | 10 ppm | 2 ppm |
| Ia-iv | 90 | 11 | 0 |
| Ia-vii | 100 | 9 | 0 |
| Ia-ix | 34 | 39 | 10 |
| Ia-xii | 22 | 36 | 16 |

Example 3

Yeast Growth Inhibition Assay

Yeast cells (Ade2 strain) were grown in liquid YPD (1% yeast extract, 2% peptone, 2% dextrose) for 16 hours at 30° C. from previously sub-cultured plates of Saccharomyces cerevisiae. The OD600 of the overnight culture was checked via spectrophotometer and diluted to a concentration of $2 \times 10^4$ cells/ml.

Chemistry stocks were dissolved in DMSO to a concentration of 10 mM. Chemistry stocks were further diluted in a 96-well stock plate to obtain final concentrations of 100, 33, 10 and 1 µM in 1% DMSO. The final concentrations of the soraphen positive controls were 400, 40, and 3.2 nM. The negative controls on each plate included a background subtraction control containing yeast and 1% DMSO (without chemistry) and a second contamination control containing YPD (with no yeast) and 1% DMSO (without chemistry).

98 µl liquid YPD was added to 2 µl diluted stock of DMSO per well and mixed thoroughly. After mixing, 100 µl of the diluted yeast solution was added to bring the final yeast concentration to $1 \times 10^4$ cells/ml or 2000 cells per well. An initial spectrophotometric reading at OD600 was conducted on the entire plate and served as the 0 hour time point used to subtract any background. The plate was then incubated for 24 hours at 30° C. with mild shaking. At the 24 hour time point all wells of the plate were re-suspended by pipette to yield a uniform suspension, then read again at OD600. The OD600 reading at 0 hours (background) was subtracted from the 24 hour OD600 reading and all wells were compared to the negative control and subtracted from 100 to determine the percent inhibition. All experiments were conducted in triplicate. Averages were reported along with standard deviation calculation to generate error bars. Each plate contained its own controls and consisted of inoculated+DMSO, non-inoculated+DMSO, and a titration series of soraphen at 400, 40, and 3.2 nM. The results of growth inhibition for Saccharomyces cerevisiae are reported in Table 3 below.

TABLE 3

Growth Inhibition of Saccharomyces cerevisiae

| Formula | S. cerevisiae % growth inhibition at 48 hours | | | |
|---|---|---|---|---|
| | 100 µM | 33.3 µM | 11.1 µM | 3.7 µM |
| Ia-viii | 100 | 62 | 23 | 6 |
| Ia-x | 99 | 46 | 13 | 12 |
| Ia-ii | 51 | 12 | 0 | 7 |

Description of Synthesis of Compounds Described Herein

Generally, the compounds of Formulas I, Ia, Ib, II, IIa, and IIb may be prepared using methods known to those skilled in the art.

Example 4

Description of Synthesis of Compounds of Formula I

For example, compounds of Formula I can be prepared as set forth in Scheme 1 below. More particularly, the synthesis of compound 5 starts with the preparation of pyridine derivative 3 from a diketone 1 and cyanoacetamide 2, followed by alkylation with 1-bromophenyl acetic acid 4 in presence of aqueous KOH in acetone. Alternatively, alkylation can be accomplished with methyl a-bromophenylacetate and $K_2CO_3$ via formation of a methyl ester derivative 7 and subsequent hydrolysis with 1N NaOH to afford a desired carboxylic acid compound 5. The racemate compound 5 can be separated into single enantiomers by preparative HPLC using a chiral stationary column.

Substituents E and $R^6$ may be selected as set forth with regard to Formula I above.

Scheme 1: Synthetic scheme for the preparation of compounds of Formula I

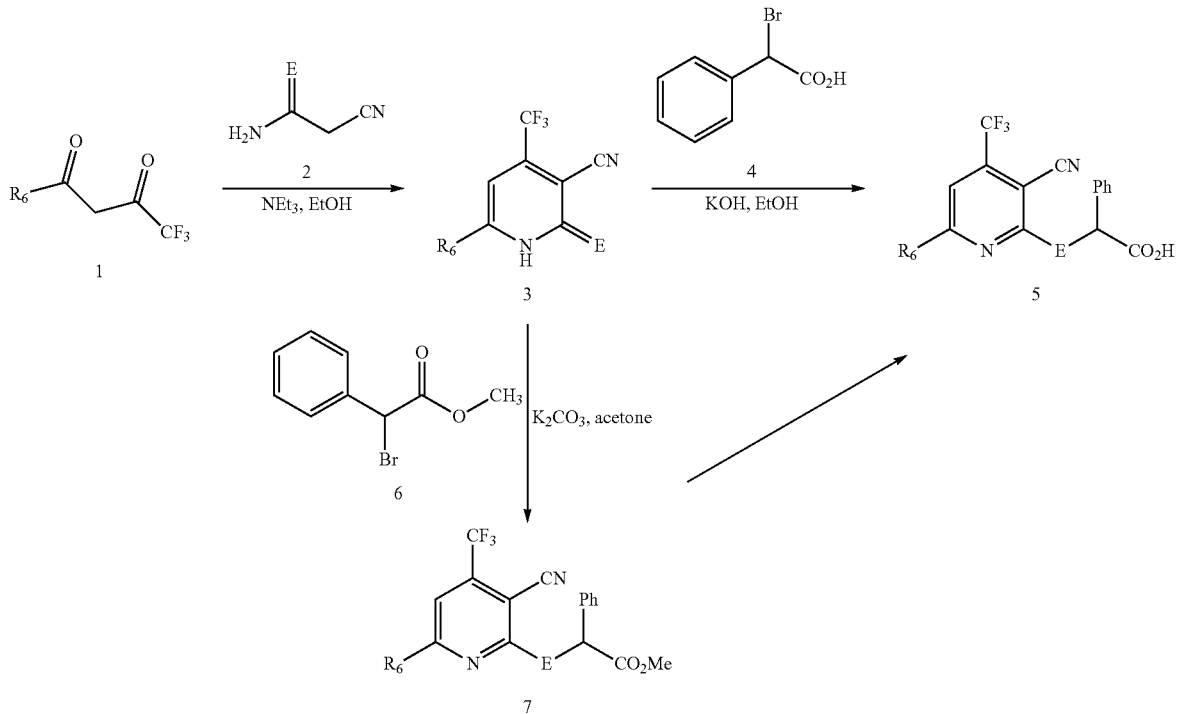

Alternatively, the compounds of Formula I may be prepared as generally set forth in Scheme 2 below. The general method depicted in Scheme 2 involves the formation of pyridine derivatives 5 from chalcone 3 and a 2-cyanoacetamide 4 in ethanol (EtOH) in the presence of catalytic amount of pyridine. The chalcone 3 can be prepared, for example, by a Claisen-condensation of the corresponding aldehyde 2 and acetyl-compound 1 in presence of aqueous NaOH in ethanol. Alkylation of pyridine derivative 5 with methyl α-bromophenylacetate 6 can be performed in the presence of $K_2CO_3$ in acetone. The saponification of the methyl ester 7 may be achieved with aqueous 1N LiOH in tetrahydrofuran (THF)/methanol (MeOH) mixture to yield the final product 8.

Substituents E and $R^4$ through $R^6$ may be selected as set forth with regard to Formula I above.

Scheme 2: Synthetic scheme for the preparation of compounds of Formula I

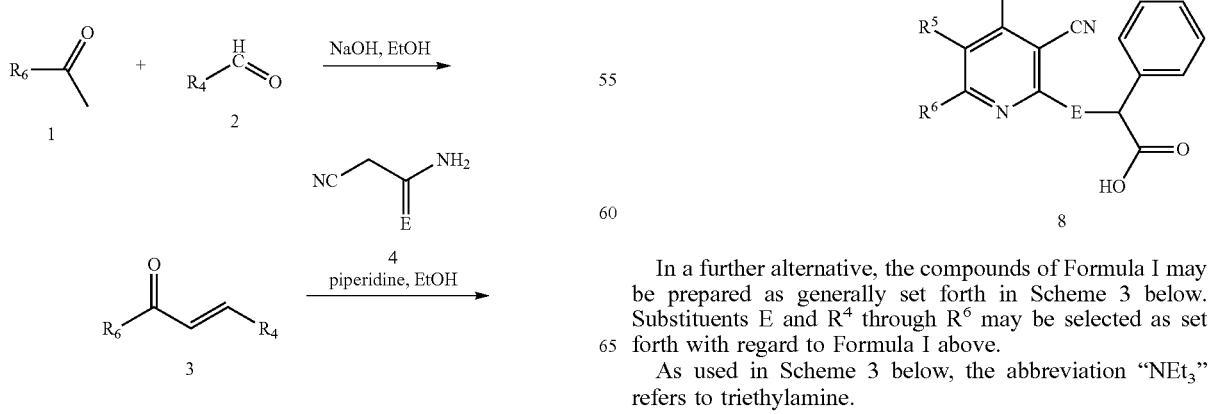

In a further alternative, the compounds of Formula I may be prepared as generally set forth in Scheme 3 below. Substituents E and $R^4$ through $R^6$ may be selected as set forth with regard to Formula I above.

As used in Scheme 3 below, the abbreviation "$NEt_3$" refers to triethylamine.

Scheme 3: Synthetic scheme for the preparation of compounds of Formula I

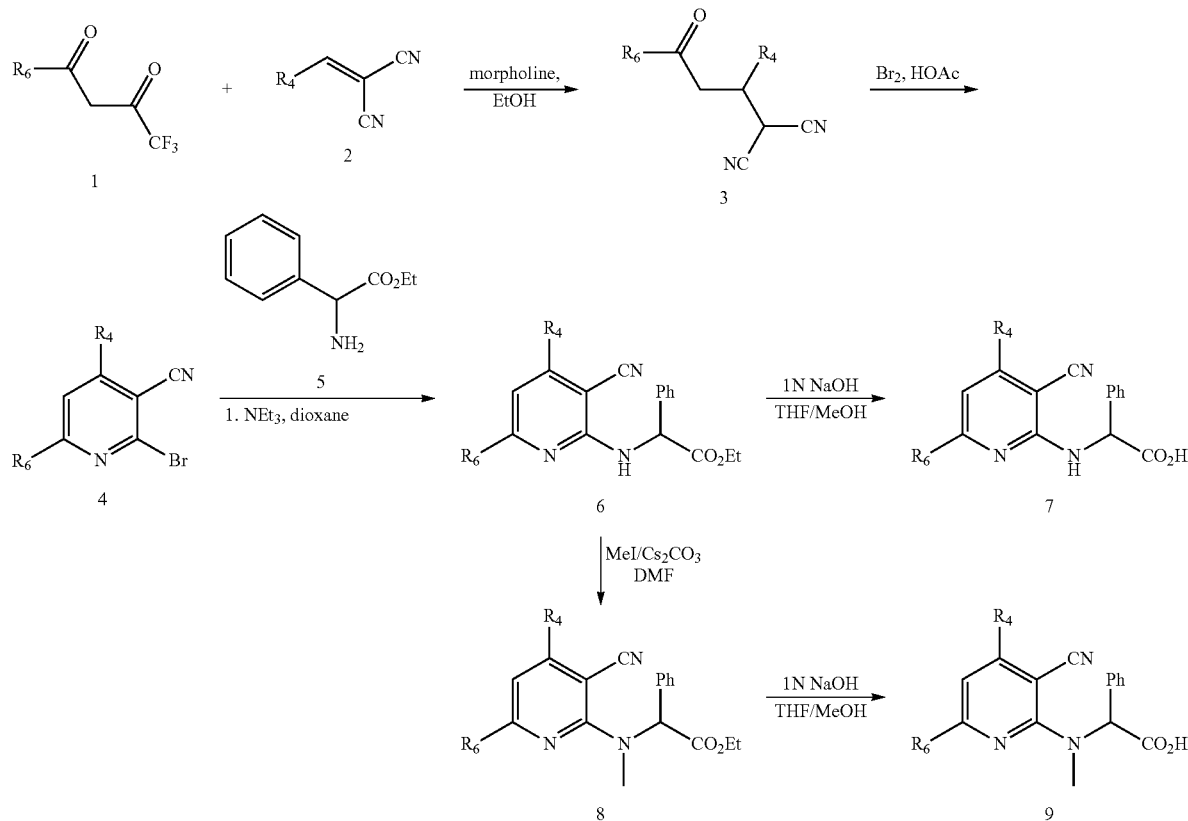

In a further alternative, the compounds of Formula I may be prepared as generally set forth in Scheme 4 below. More particularly, the method disclosed in Scheme 4 involves the formation of the thiopyridine derivative 5 via the thiopyran-intermediate 4, which is subsequently treated with the cyclohexanone-morpholine enamine.

Substituents E, $R^4$, and $R^6$ may be selected as set forth with regard to Formula I above.

Scheme 4: Synthetic scheme for the preparation of compounds of Formula I

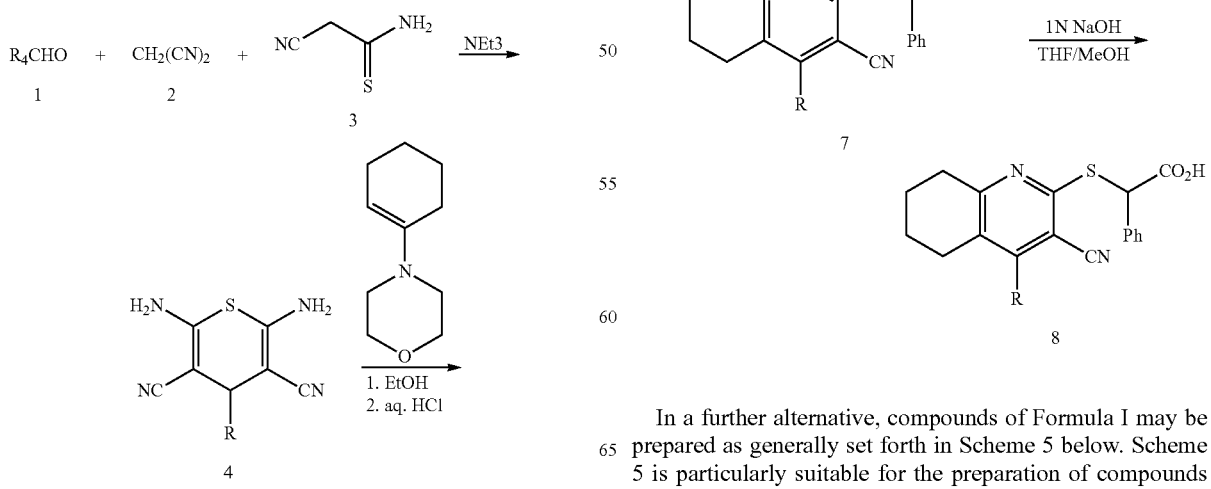

In a further alternative, compounds of Formula I may be prepared as generally set forth in Scheme 5 below. Scheme 5 is particularly suitable for the preparation of compounds wherein $R^4$ is heteroaryl.

More particularly, the process involves reaction of the 2-cyanothioacetamide 2 and the heteroaryl carboxaldehyde 1, followed by reaction with cyclohexanone to give the desired thiopyridine derivative 2. Alkylation of intermediate 2 with methyl α-bromophenylacetate, followed by saponification yields the product compound 5. Generally, substituent $R^4$ may be selected as set forth with regard to Formula I above.

Scheme 5: Synthetic scheme for the preparation of compounds of Formula I

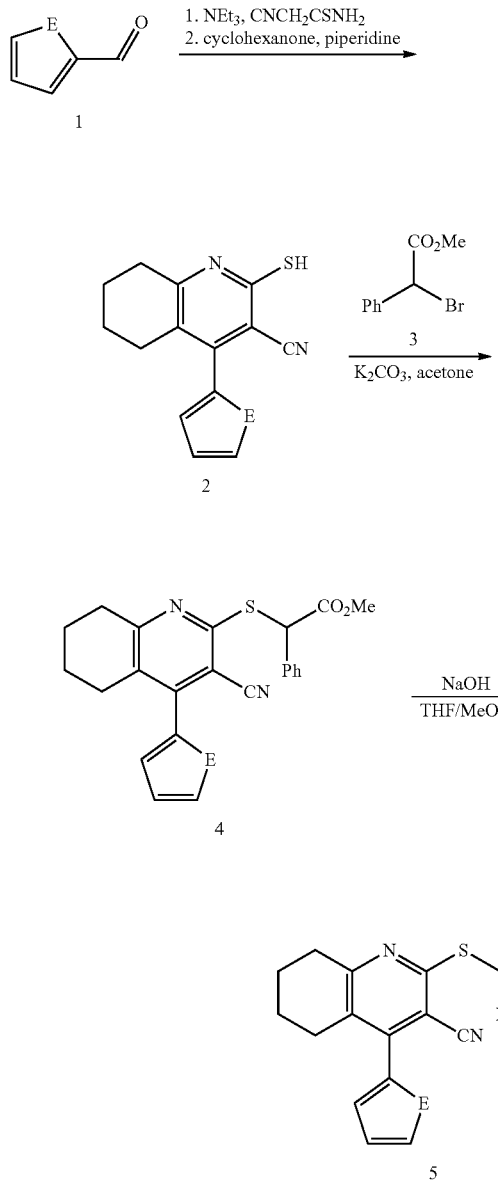

In a further alternative, compounds of Formula I may be prepared as generally set forth in Scheme 6 below. Scheme 6 is particularly suitable for the preparation of compounds wherein $R^3$ is hydrogen.

In a first step of the process, the chalcone 1 is treated with acetyl glycinamide in the presence of cesium carbonate and N,N-dimethylformamide (DMF) to give 2-hydroxypyridine 3. The intermediate 3 can be transformed with Lawesson's reagent to form the corresponding thiopyridine derivatives 4, followed by alkylation to form the methyl ester intermediate 6 and saponification to form the final product 7.

Alternatively, the intermediate 3 can be alkylated with methyl α-bromophenylacetate to form corresponding compounds of Formula I wherein the E substituent is O. Substituents $R^4$ and $R^6$ may be selected as generally set forth with regard to Formula I above.

Scheme 6: Synthetic scheme for the preparation of compounds of Formula I

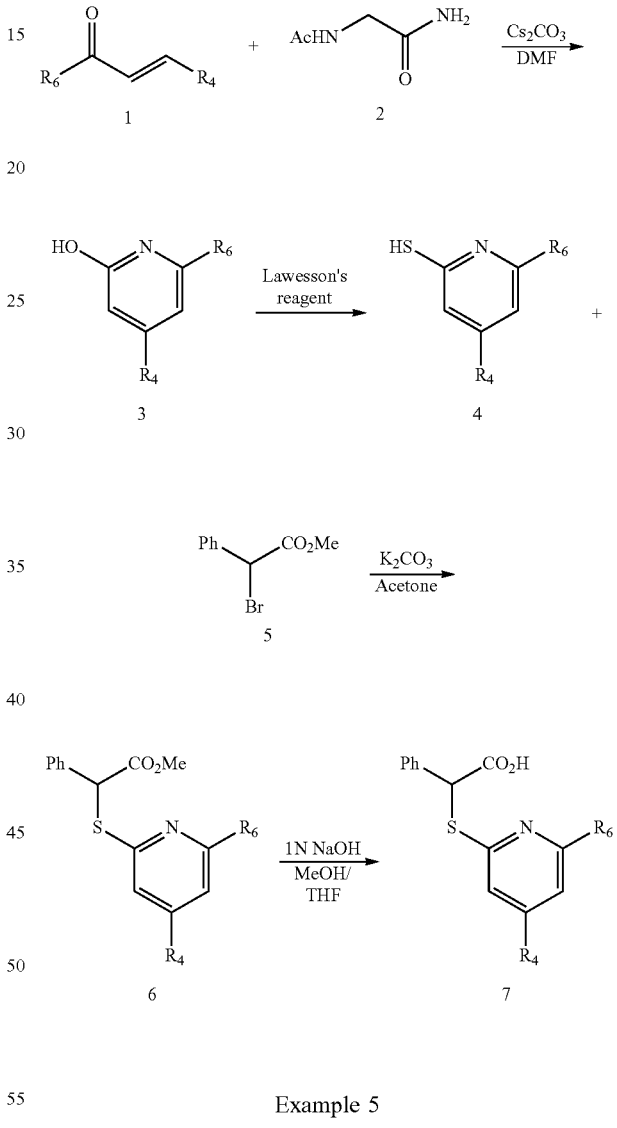

Example 5

Description of Synthesis of Compounds of Formula I

Compounds of Formula I may be prepared as set forth in exemplary Scheme 7 below. Substituents E and $R^3$ through $R^6$ may be selected as generally set forth with regard to Formula I above.

As used in Scheme 7 below, "AIBN" refers to azobisisobutyronitrile.

Scheme 7: Synthetic scheme for the preparation of compounds of Formula I

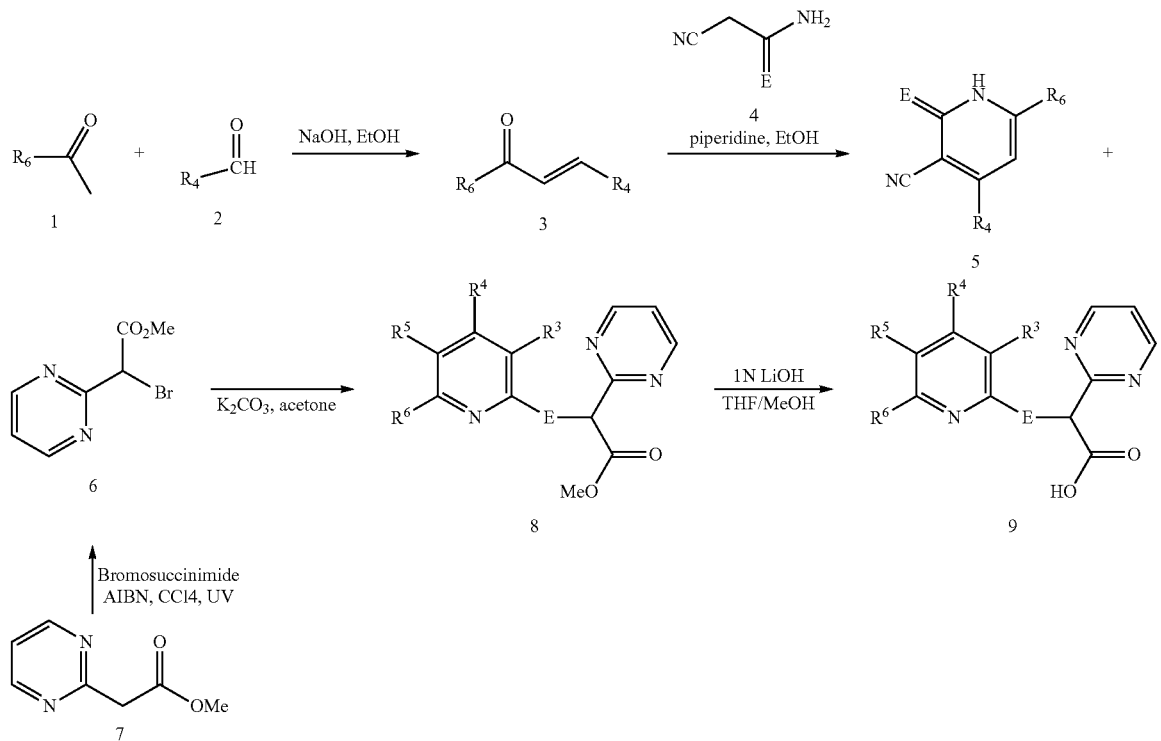

Alternatively, compounds of Formula I may be prepared as set forth in exemplary Scheme 8 below. Generally, preparation of the the pyridine derivative 5 may be accomplished using the same procedure as depicted in Scheme 7 above. The corresponding alcohol 7 is then prepared by alkylation of the pyridine derivative 5 with 2-bromo-2-phenylethanol 6. Substituents E and $R^3$ through $R^6$ may be selected as generally set forth with regard to Formula I above.

Scheme 8: Synthetic scheme for the preparation of compounds of Formula II

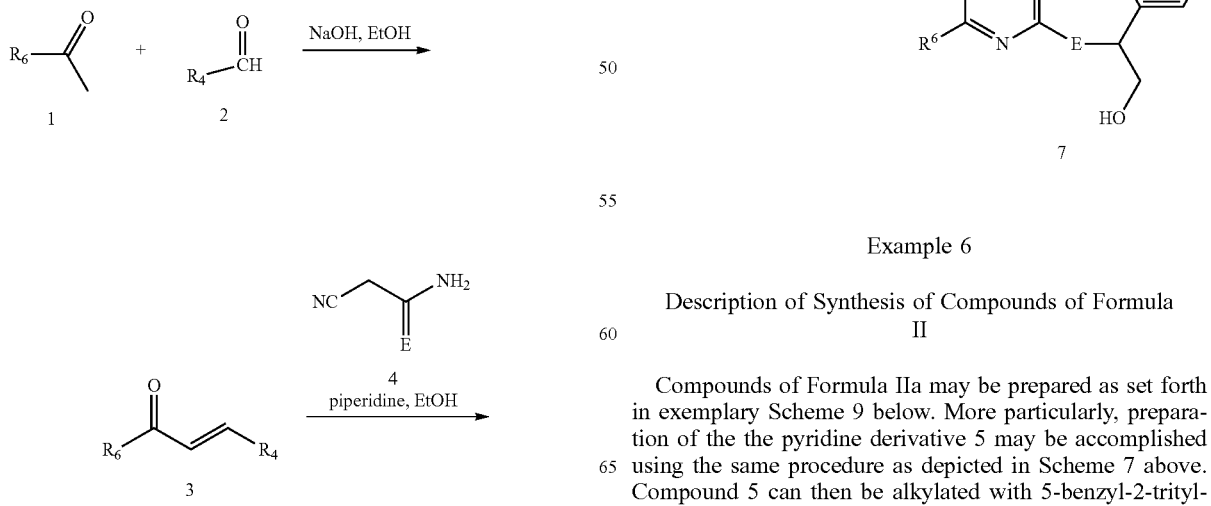

Example 6

Description of Synthesis of Compounds of Formula II

Compounds of Formula IIa may be prepared as set forth in exemplary Scheme 9 below. More particularly, preparation of the the pyridine derivative 5 may be accomplished using the same procedure as depicted in Scheme 7 above. Compound 5 can then be alkylated with 5-benzyl-2-trityl-tetrazole 4 to give, following deprotection, the corresponding tetrazole product 7. Substituents E and $R^4$ through $R^6$ may be selected as generally set forth with regard to Formula IIa above.

As used in Scheme 9 below, the abbreviation "$TMSN_3$," refers to trimethylsilyl azide, the abbreviation "TBAF" refers to tetra-n-butylammonium fluoride, and the abbreviation "DCM" refers to dichloromethane.

Scheme 9: Synthetic scheme for the preparation of compounds of Formula IIa

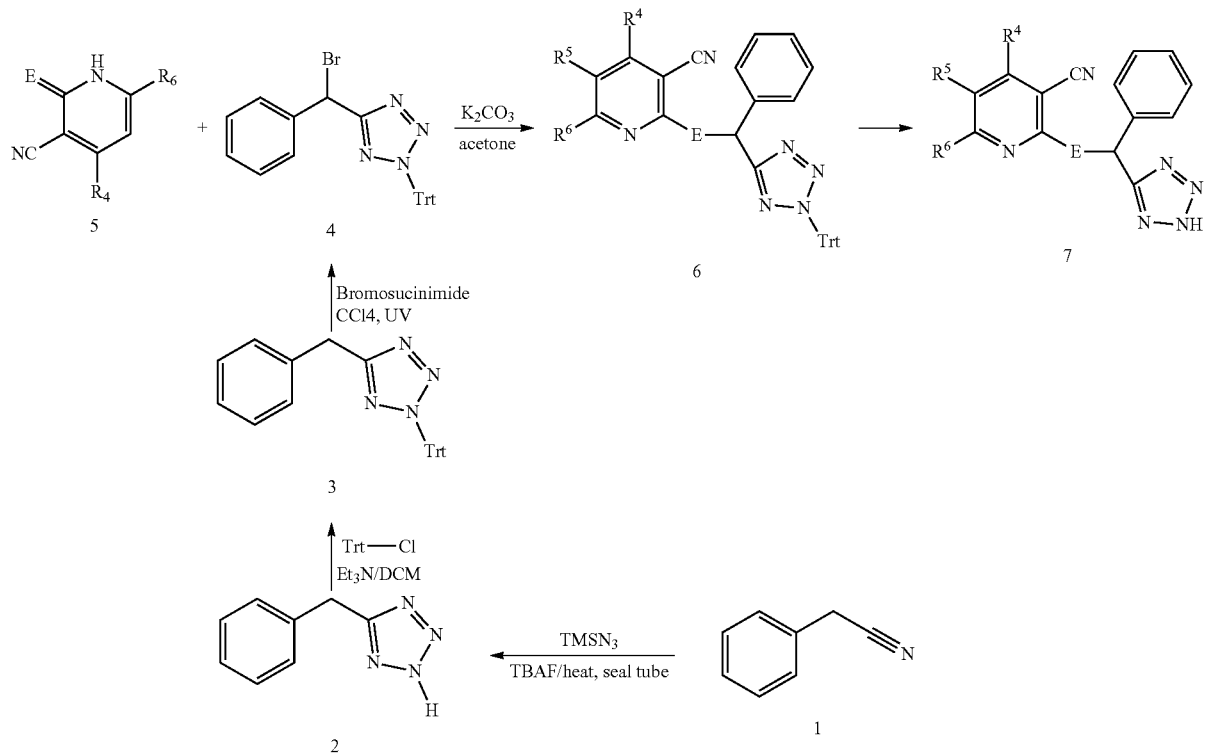

piperidine (0.1 mL) in ethanol (20 mL) was refluxed for 5 hours. The mixture was cooled down to room temperature. The resulting precipitate was filtered off and dried in the air affording the pyridine derivatives 5 in yields varying from 10 to 30%. If there was no precipitate water was added (10 mL) to induce precipitation. The resulting precipitate was filtered off and dried in air.

Example 7

General Procedure for the Preparation of Compounds of Formula I According to Exemplary Scheme 2

The following compounds and procedures, each of which is referenced in exemplary Scheme 2 above, were prepared and/or carried out using as set forth in detail below.

General Procedure of Preparation of Chalcones 3

Sodium hydroxide (3N, 46 mL, 3 equiv.) was added to a mixture of ketone 1 (46 mmol, 1 equiv.) and aldehyde 2 (46 mmol, 1 equiv.) in ethanol (100 mL). The mixture was stirred for 4 h. The resulting precipitate was filtered off and washed with a litte ethanol and water. The solid was dried in the air to afford the desired chalcone 3. If there was no precipitate water was added. The mixture was extracted with ethyl acetate (3×). The combined organic layers were dried over $Na_2SO_4$ and concentrated in vacuo. The residue was purified with automated column chromatography ($SiO_2$, heptane/ethyl acetate, gradient).

General Procedure of Preparation of Thiopyridine Derivatives 5

A mixture of chalcone 3 (5 mmol, 1 equiv.), 2-cyanothioacetamide (5 mmol, 1 equiv.) and a catalytic amount of If there was still no precipitate, the mixture was allowed to stand overnight and was then decanted. The residue was purified with column chromatography ($SiO_2$, heptane/ethyl acetate, gradient).

General Procedure of Alkylation of Pyridine Derivative 5

A mixture of pyridine derivatives 5 (1.0 equiv.), $K_2CO_3$ (1.1 equiv.) and methyl 1-bromo-phenylacetate (1.1 equiv.) in acetone (15 mL) was refluxed for 2 hours. The mixture was cooled to room temperature and filtered. The filtrate was concentrated to yield the desired methyl ester derivatives 7. If necessary purification was performed with an automated column chromatography ($SiO_2$, heptane/ethyl acetate, gradient).

General Procedure of Saponification of the Methylester Derivatives 7.

NaOH (1N, 2 mL) was added to a mixture of 7 (1 mmol) in THF (2 mL) and methanol (2 mL). After 4 h the mixture was concentrated and stripped to dryness with toluene. The residue was suspended in ethyl acetate and filtered. The filtrate was washed with ethyl acetate, until the filtrate was colorless. The solid was dissolved in water and the solution was acidified with 1N HCl. The resulting precipitate was filtered off and washed with a little water. The solid was dried to the air to afford an off-white solid.

Unless otherwise noted, the general procedures described above were used to synthesise these compounds, to the extent that they appear, in the further examples below.

Example 8

Preparation of 2-((3-cyano-6-(thiophen-2-yl)-4-(trifluoromethyl) pyridin-2-yl)thio)-2-phenylacetic acid (Formula Ia-ii)

2-Cyanoethanethioamide (1.4 g, 13.5 mmol) was added to a solution of 4,4,4-trifluoro-1-(thiophen-2-yl)butane-1,3-dione (3.0 g, 13.5 mmol) and triethylamine (3.0 mL) in ethanol (10 mL). The resulting mixture was refluxed for 2 hours, and then diluted with water (20 mL). The precipitate was filtered and washed with water (3×20 mL) and dried in air to give triethylamine salt of 2-mercapto-6-(thiophen-2-yl)-4-(trifluoromethyl)nicotinonitrile (4.25 g, 11.0 mmol, 81%) as a yellow solid.

Aqueous KOH (10%, 0.56 mL) was added to a solution of the triethylamine salt of 2-mercapto-6-(thiophen-2-yl)-4-(trifluoromethyl)-nicotinonitrile (387 mg, 1.0 mmol) in ethanol, followed by the addition of alpha-bromophenyl acetic acid (215 mg, 1.0 mmol). The mixture was refluxed for 3 hours and cooled to room temperature. The organic solvent was removed in vacuo and H$_2$O (20 mL) was added to the residue. The pH was adjusted to 6 with 1M HCl. The precipitate was filtered off and washed with H$_2$O (3×20 mL) and dried in air to give racemic 2-((3-cyano-6-(thiophen-2-yl)-4-(trifluoromethyl)-pyridin-2-yl)thio)-2-phenylacetic acid (370 mg, 0.88 mmol, yield 88%) as a reddish solid. LC-MS [M+H] 421 (C$_{19}$H$_{11}$F$_3$N$_2$O$_2$S$_2$+H, requires 421.02).

A portion of the racemic product (200 mg) was separated into enantiomers by preparative HPLC on a chiral stationary column (Chiralpak IA-column, 20×250 mm, Flow 10 ml/min) using as a mobile phase a mixture of heptane/ethanol/trifluoroacetic acid (85/15/0.2) to yield 63 mg of enantiomer 1 (Formula Ia-ii-e1) and 66 mg of enantiomer 2 (Formula Ia-ii-e2). Both enantiomers were analyzed for enantiomeric purity by HPLC using Chiralpak IC-column (0.46×20) and as a mobile phase a mixture of heptane/ethanol/trifluoroacetic acid (75/20/0.2) at 0.7 ml/min flow rate. The enantiomeric excess (ee) of the Enantiomer 1 (Formula Ia-ii-e1) that was eluted at R$_t$=9.75 min was determined to be 97.3% and Enantiomer 2 (Formula Ia-ii-e2) that was eluted at Rt=7.89 min was 99.8%, respectively. LC-MS and $^1$H-NMR spectra for both enantiomers were in accordance with the chemical structure. LC-MS LC-MS [M+H] 421 (C$_{19}$H$_{11}$F$_3$N$_2$O$_2$S$_2$+H, requires 421.02).

The absolute configuration of the enantiomer 2 (Formula Ia-ii-e2) was resolved by X-ray crystallography analysis and found to be the S configuration (see FIG. 1).

Table 4 below contains the x-ray crystallographic coordinates for enantiomer 2. The coordinates are listed in Angstroms. Enantiomer 2 crystallized in a unit cell with dimensions of a=5.257 Å, b=8.096 Å, c=19.325 Å with alpha=beta=gamma angles equal to 90° in a P 21 21 21 space group.

TABLE 4

| | X-ray crystallographic coordinates, space group and unit cell for Enantiomer 2 (Formula Ia-ii-e2) | | | | | |
|---|---|---|---|---|---|---|
| Atom Number | Atom Type | x | y | z | occupancy | temparature factor |
| ATOM 1 | 1 S1 | 4.517 | 16.195 | 3.23 | 1 | 1.11 |
| ATOM 2 | 2 F1 | 6.562 | 13.107 | 7.178 | 1 | 2.46 |
| ATOM 3 | 3 F2 | 5.123 | 11.551 | 7.448 | 1 | 2.67 |
| ATOM 4 | 4 F3 | 4.745 | 13.498 | 8.234 | 1 | 2.48 |
| ATOM 5 | 5 O1 | 4.048 | 14.287 | 0.878 | 1 | 1.25 |
| ATOM 6 | 6 O2 | 1.873 | 14.852 | 0.719 | 1 | 1.25 |
| ATOM 7 | 7 H2 | 1.825 | 14.161 | 0.243 | 1 | 1.87 |
| ATOM 8 | 8 N1 | 3.086 | 13.988 | 3.683 | 1 | 1.01 |
| ATOM 9 | 9 N2 | 6.751 | 16.049 | 5.911 | 1 | 1.84 |
| ATOM 10 | 10 C1 | 3.205 | 16.256 | 1.987 | 1 | 0.98 |
| ATOM 11 | 11 H1 | 2.33 | 16.426 | 2.44 | 1 | 1.17 |
| ATOM 12 | 12 C2 | 3.507 | 17.402 | 1.034 | 1 | 0.93 |
| ATOM 13 | 13 C3 | 2.631 | 18.467 | 0.932 | 1 | 1.26 |
| ATOM 14 | 14 H3 | 1.874 | 18.513 | 1.505 | 1 | 1.51 |
| ATOM 15 | 15 C4 | 2.852 | 19.465 | 0.001 | 1 | 1.58 |
| ATOM 16 | 16 H4 | 2.25 | 20.197 | −0.063 | 1 | 1.89 |
| ATOM 17 | 17 C5 | 3.953 | 19.395 | −0.837 | 1 | 1.49 |
| ATOM 18 | 18 H5 | 4.101 | 20.075 | −1.483 | 1 | 1.79 |
| ATOM 19 | 19 C6 | 4.834 | 18.338 | −0.735 | 1 | 1.44 |
| ATOM 20 | 20 H6 | 5.591 | 18.295 | −1.307 | 1 | 1.72 |
| ATOM 21 | 21 C7 | 4.617 | 17.34 | 0.199 | 1 | 1.26 |
| ATOM 22 | 22 H7 | 5.225 | 16.614 | 0.27 | 1 | 1.51 |
| ATOM 23 | 23 C8 | 3.101 | 14.994 | 1.161 | 1 | 0.97 |
| ATOM 24 | 24 C9 | 4.086 | 14.746 | 4.125 | 1 | 0.99 |
| ATOM 25 | 25 C10 | 4.853 | 14.428 | 5.26 | 1 | 1.02 |
| ATOM 26 | 26 C11 | 4.562 | 13.235 | 5.918 | 1 | 1.1 |
| ATOM 27 | 27 C12 | 3.565 | 12.425 | 5.438 | 1 | 1.19 |
| ATOM 28 | 28 H12 | 3.371 | 11.6 | 5.866 | 1 | 1.43 |
| ATOM 29 | 29 C13 | 2.835 | 12.822 | 4.312 | 1 | 1.02 |
| ATOM 30 | 30 C14 | 5.916 | 15.311 | 5.648 | 1 | 1.22 |
| ATOM 31 | 31 C15 | 5.256 | 12.849 | 7.194 | 1 | 1.42 |
| ATOM 32 | 32 C16A | 1.771 | 12.014 | 3.744 | 0.799 | 0.97 |
| ATOM 33 | 33 C17A | 0.833 | 12.31 | 2.781 | 0.799 | 1.49 |
| ATOM 34 | 34 H17A | 0.817 | 13.138 | 2.316 | 0.799 | 1.79 |
| ATOM 35 | 35 C18A | −0.088 | 11.3 | 2.546 | 0.799 | 1.24 |
| ATOM 36 | 36 H18A | −0.797 | 11.371 | 1.917 | 0.799 | 1.48 |
| ATOM 37 | 37 C19A | 0.132 | 10.199 | 3.311 | 0.799 | 1.36 |

TABLE 4-continued

X-ray crystallographic coordinates, space group and unit cell for Enantiomer 2 (Formula Ia-ii-e2)

| | Atom Number | Atom Type | x | y | z | occupancy | temparature factor |
|---|---|---|---|---|---|---|---|
| ATOM 38 | 38 | H19A | −0.394 | 9.409 | 3.274 | 0.799 | 1.63 |
| ATOM 39 | 39 | S2A | 1.479 | 10.412 | 4.353 | 0.799 | 1.44 |
| ATOM 40 | 40 | C16B | 1.757 | 11.936 | 3.921 | 0.201 | 0.97 |
| ATOM 41 | 41 | C17B | 1.439 | 10.678 | 4.309 | 0.201 | 1.49 |
| ATOM 42 | 42 | H17B | 1.864 | 10.208 | 5.017 | 0.201 | 1.79 |
| ATOM 43 | 43 | C19B | 0.417 | 10.175 | 3.54 | 0.201 | 1.36 |
| ATOM 44 | 44 | H19B | 0.035 | 9.32 | 3.703 | 0.201 | 1.63 |
| ATOM 45 | 45 | C18B | −0.008 | 10.973 | 2.541 | 0.201 | 1.24 |
| ATOM 46 | 46 | H18B | −0.694 | 10.75 | 1.923 | 0.201 | 1.48 |
| ATOM 47 | 47 | S2'B | 0.868 | 12.452 | 2.544 | 0.201 | 1.44 |

Example 9

Preparation of methyl 2-((3-cyano-6-(thiophen-2-yl)-4-(trifluoromethyl) pyridin-2-yl)thio)-2-phenylacetate (Formula IIb-iii)

A mixture of triethylamine salt of 2-mercapto-6-(thiophen-2-yl)-4-(trifluoromethyl)-nicotinonitrile (387 mg, 1.0 mmol), methyl α-bromophenylacetate (225 mg, 1.0 mmol) and $K_2CO_3$ (150 mg, 1.1 mmol) in acetone (10 mL) was refluxed for 2 hours under a $N_2$-atmosphere. The mixture was cooled to room temperature and filtered. The filtrate was concentrated in vacuo to give methyl 2-((3-cyano-6-(thiophen-2-yl)-4-(trifluoromethyl)pyridin-2-yl)thio)-2-phenylacetate (380 mg, 0.87 mmol, yield 87%) as a yellowish solid with an HPLC purity of 94.4%. LC-MS [M+H] 435 ($C_{20}H_{13}F_3N_2O_2S_2$+H, requires 435.04). The $^1$H-NMR spectrum was in accordance with the chemical structure.

Example 10

Preparation of 2-((3-cyano-4-(4-methoxyphenyl)-6-(thiophen-2-yl)pyridin-2-yl)thio)-2-phenylacetic acid (Formula Ia-xiv)

The reaction of 2-acetylthiophene (2.05 mL, 2.38 g, 18.9 mmol) and p-anisaldehyde (2.3 mL, 18.9 mmol) afforded chalcone (E)-3-(4-methoxyphenyl)-1-(thiophen-2-yl)prop-2-en-1-one with 89% yield (4.13 g, 16.9 mmol) as an off-white solid (Obtained by precipitation). The $^1$H-NMR spectrum was in accordance with the chemical structure.

The reaction of chalcone (E)-3-(4-methoxyphenyl)-1-(thiophen-2-yl)prop-2-en-1-one (1.5 g, 6.1 mmol) with 1 equivalent 2-cyanothioacetamide afforded the desired thiopyridine derivative that was purified by silica gel chromatography. The pure 4-(4-methoxyphenyl)-6-(thiophen-2-yl)-2-thioxo-1,2-dihydropyridine-3-carbonitrile was obtained with 24% yield (470 mg, 1.4 mmol) as an orange solid. The $^1$H-NMR spectrum was in accordance with the chemical structure.

Alkylation of the 4-(4-methoxyphenyl)-6-(thiophen-2-yl)-2-thioxo-1,2-dihydropyridine-3-carbonitrile (214 mg, 0.66 mmol) with methyl α-bromophenylacetate (167 mg, 0.73 mmol, 1.1 equiv.) afforded after purification methyl 2-((3-cyano-4-(4-methoxyphenyl)-6-(thiophen-2-yl)pyridin-2-yl)thio)-2-phenylacetate with 78% yield (242 mg, 0.51 mmol) as an off-white solid after precipitation from ethyl acetate (3 mL). The $^1$H-NMR spectrum was in accordance with the chemical structure.

The saponification of the methyl 2-((3-cyano-4-(4-methoxyphenyl)-6-(thiophen-2-yl)pyridin-2-yl)thio)-2-phenylacetate (242 mg, 0.530 mmol) was carried out with 1N NaOH in the THF/methanol mixture and the desired product 2-((3-cyano-4-(4-methoxyphenyl)-6-(thiophen-2-yl)pyridin-2-yl)thio)-2-phenylacetic acid was isolated as described in the general procedure.

The racemic crude product was separated into enantiomers by preparative HPLC on a chiral stationary column (Chiralpak IC-column, 20×250 mm, Flow rate at 17 ml/min) using as a mobile phase a mixture of heptane/ethanol/trifluoroacetic acid (80/20/02) to yield 30 mg (0.065 mmole, yield 12%) of enantiomer 1 (Formula Ia-xiv-e1) as off-white solid and 33 mg (0.074 mmol, yield 14%) of enantiomer 2 (Formula Ia-xiv-e2) as off-white soild. Both enantiomers were analyzed for enantiomeric purity by HPLC using Chiralpak IC-column (0.46×25) and as a mobile phase a mixture of heptane/ethanol/trifluoroacetic acid (80/20/02) at 0.7 ml/min flow rate. The enantiomeric excess (ee) of the Enantiomer 1 (Formula Ia-xiv-e1) that was eluted at $R_t$=15.64 min was determined to be 99.3% and Enantiomer 2 (Formula Ia-xiv-e2) that was eluted at $R_t$=18.13 min was 99.2%, respectively. LC-MS and The $^1$H-NMR spectra for both enantiomers are in accordance with the chemical structure. LC-MS LC-MS [M+H] 459.1 ($C_{25}H_{18}N_2O_3S_2$+H, requires 459.08).

Example 11

Preparation of 2-((3-cyano-4,6-di(thiophen-2-yl) pyridin-2-yl) thio)-2-phenylacetic Acid (Formula Ia-iii)

The reaction of 2-acetylthiophene (2.5 mL, 23.0 mmol) and 2-thiophene carboxaldehyde (2.15 mL, 23.0 mmol) afforded chalcone (E)-1,3-di(thiophen-2-yl)prop-2-en-1-one with 93% yield (4.7 g, 21.3 mmol) as a brown solid (Obtained by precipitation). The $^1$H-NMR spectrum was in accordance with the chemical structure.

The reaction of chalcone (E)-3-(4-methoxyphenyl)-1-(thiophen-2-yl)prop-2-en-1-on (1.5 g, 6.1 mmol) with 1 equivalent 2-cyanothioacetamide afforded the desired thiopyridine derivative that was purified by silica gel chromatography. The pure 4-(4-methoxyphenyl)-6-(thiophen-2-yl)-2-thioxo-1,2-dihydropyridine-3-carbonitrile was obtained with a 24% yield (470 mg, 1.4 mmol) as an orange solid. The $^1$H-NMR spectrum was in accordance with the chemical structure.

Alkylation of the 4-(4-methoxyphenyl)-6-(thiophen-2-yl)-2-thioxo-1,2-dihydropyridine-carbonitrile (500 mg, 1.7 mmol) with methyl a-bromophenylacetate (428 mg, 1.87 mmol, 1.1 equiv.) afforded methyl 2-((3-cyano-4,6-di(thiophen-2-yl)pyridin-2-yl)thio)-2-phenylacetate (150 mg, 0.33 mmol, 20%) as a beige solid. The $^1$H-NMR spectrum was in accordance with the chemical structure.

The saponification of the methyl 2-((3-cyano-4,6-di(thiophen-2-yl)pyridin-2-yl)thio)-2-phenylacetate (150 mg, 0.330 mmol) was carried out with 1N NaOH in the THF/methanol mixture and the crude product 2-((3-cyano-4,6-di(thiophen-2-yl)pyridin-2-yl)thio)-2-phenylacetic acid was isolated using the general procedure as described in the examples above.

The racemic acid product was separated into enantiomers by preparative HPLC on a chiral stationary column (Chiralpak IC-column, 20×250 mm, Flow rate at 17 ml/min) using as a mobile phase a mixture of heptane/ethanol/trifluoroacetic acid (80/20/02) to yield 2.36 mg (0.0 5.4 mmol, 1.6%) of enantiomer 1(Formula Ia-iii-e1) as an off-white solid and 17.8 mg (0.041 mmol, yield 12%) of enantiomer 2 (Formula Ia-iii-e2) as an off-white soild. Both enantiomers were analyzed for enantiomeric purity by HPLC using Chiralpak IC-column (0.46×25) and as a mobile phase a mixture of heptane/ethanol/trifluoroacetic acid (80/20/02) at 0.7 ml/min flow rate. The enantiomeric excess (ee) of the Enantiomer 1 (Formula Ia-iii-e1) that was eluted at $R_t$=14.87 min was determined to be 90.7% and Enantiomer 2 (Formula Ia-iii-e2) that was eluted at $R_t$=18.51 min was 98.7%, respectively. LC-MS and The $^1$H-NMR spectra for both enantiomers are in accordance with the chemical structure. LC-MS LC-MS [M+H] 435 ($C_{22}K_{14}N_2O_2S_3$ +H, requires 435.02).

Example 12

Preparation of 2-((4-(4-methoxyphenyl)-6-(thiophen-2-yl) pyridin-2-yl)thio)-2-phenylacetic acid (Formula Ia-xix)

The reaction of 2-acetylthiophene (2.05 mL, 2.38 g, 18.9 mmol) and p-anisaldehyde (2.3 mL, 18.9 mmol) afforded chalcone (E)-3-(4-methoxyphenyl)-1-(thiophen-2-yl)prop-2-en-1-one with 89% yield (4.13 g, 16.9 mmol) as an off-white solid (Obtained by precipitation). The $^1$H-NMR spectrum was in accordance with the chemical structure.

A mixture of chalcone (E)-3-(4-methoxyphenyl)-1-(thiophen-2-yl)prop-2-en-1-one (1.5 g, 6.1 mmol), N-acetylglycinamide (850 mg, 7.3 mmol, 1.2 equiv.) and $Cs_2CO_3$ (2.4 g, 7.3 mmol, 1.2 equiv.) in DMF (15 mL) was refluxed until TLC showed complete conversion. After 1 d conversion was complete and the mixture was poured into 3N HCl (50 mL). The mixture was extracted with $CH_2Cl_2$ (2×30 mL). The combined organic layers were washed with $H_2O$ (100 mL) and brine (100 ml) and dried over $Na_2SO_4$. The solvent was evaporated in vacuo and the residue was taken up in $CH_2Cl_2$. A solid precipitated and the filtrate was purified by automated column chromatography on the ISCO-companion (SiO$_2$, gradient ethyl acetate/heptane) to give 4-(4-methoxyphenyl)-6-(thiophen-2-yl)pyridin-2(1H)-one (839 mg, 2.96 mmol, 48%) as a brown solid. The $^1$H-NMR spectrum was in accordance with the chemical structure.

A mixture of 4-(4-methoxyphenyl)-6-(thiophen-2-yl)pyridin-2(1H)-one (400 mg, 1.41 mmol) and Lawesson's reagent (344 mg, 0.85 mmol) in THF (20 mL) was heated to reflux for 20 hours. It was concentrated and the residue was purified by automated column chromatography on the ISCO-companion (SiO$_2$, gradient ethyl acetate/heptane) to give 4-(4-methoxyphenyl)-6-(thiophen-2-yl)pyridine-2(1H)-thione (80 mg, 0.27 mmol, 31%) as a brown solid.

Alkylation of compound 4-(4-methoxyphenyl)-6-(thiophen-2-yl)pyridine-2(1H)-thione (80 mg, 0.27 mmol) with alpha-bromophenylacetic acid following the general procedure afforded methyl 2-((4-(4-methoxyphenyl)-6-(thiophen-2-yl)pyridin-2-yl)thio)-2-phenylacetate (75 mg, 0.17 mmol, 63%) as a tan solid.

Saponification of methyl 2-((4-(4-methoxyphenyl)-6-(thiophen-2-yl)pyridin-2-yl)thio)-2-phenylacetate (75 mg, 0.17 mmol) following the general procedure afforded final product 2-((4-(4-methoxyphenyl)-6-(thiophen-2-yl)pyridin-2-yl)thio)-2-phenylacetic acid (1.82 mg, 0.004 mmol, yield 3%) as a tan solid and with an HPLC purity of 87.4%. LC-MS [M+H] 434 ($C_{24}H_{19}NO_3S_2$+H, requires 434.08). The $^1$H-NMR spectrum was in accordance with the chemical structure.

Example 13

Preparation of 2-((3-cyano-6-(furan-2-yl)-4-(4-methoxyphenyl) pyridin-2-yl) thio)-2-phenylacetic acid (Formula Ia-xx)

The reaction of 2-acetylfuran (1.57 mL, 18.9 mmol) and 4-methoxybenzaldehyde (2.57 g, 18.9 mmol) afforded chalcone (E)-1-(furan-2-yl)-3-(4-methoxyphenyl)prop-2-en-1-one (3.67 g, 16.1 mmol, yield 85%) as a yellow solid (purification by column chromatography). The $^1$H-NMR spectrum was in accordance with the chemical structure.

Reaction of chalcone (E)-1-(furan-2-yl)-3-(4-methoxyphenyl)prop-2-en-1-one (1.5 g, 6.6 mmol) with 1 equivalent 2-cyanothioacetamide afforded the desired thiopyridine derivative that was purified by silica gel chromatography. The pure 6-(furan-2-yl)-4-(4-methoxyphenyl)-2-thioxo-1,2-dihydropyridine-3-carbonitrile was obtained with a 34% yield (695 mg, 2.2 mmol) as an orange solid. The $^1$H-NMR spectrum was in accordance with the chemical structure.

Alkylation of 6-(furan-2-yl)-4-(4-methoxyphenyl)-2-thioxo-1,2-dihydropyridine-3-carbonitrile (695 mg, 2.2 mmol) with methyl a-bromophenylacetate (343 mg, 0.25 mmol, 1.1 equiv.) afforded methyl 2-((3-cyano-6-(furan-2-yl)-4-(4-methoxyphenyl)pyridin-2-yl)thio)-2-phenylacetate in a 84% yield (870 mg, 1.9 mmol) as a brown solid. The $^1$H-NMR spectrum was in accordance with the chemical structure.

Saponification of methyl 2-((3-cyano-6-(furan-2-yl)-4-(4-methoxyphenyl) pyridin-2-yl)thio)-2-phenylacetate (400 mg, 0.88 mmol) with 1N NaOH in THF-methanol mixture afforded final product 2-((3-cyano-6-(furan-2-yl)-4-(4-methoxyphenyl)pyridin-2-yl)thio)-2-phenylacetic acid (70 mg, 0.16 mmol, yield 18%) as a brown solid and with an HPLC purity of 98.1%. LC-MS [M+H] 443.0 ($C_{25}H_{18}N_2O_4S_2$+H, requires 442.1). The $^1$H-NMR spectrum was in accordance with the chemical structure.

Example 14

Preparation of 2-((3-cyano-6-(thiophen-2-yl)-4-(p-tolyl)pyridin-2-yl) thio)-2-phenylacetic acid (Formula Ia-xxi)

The reaction of 2-acetylthiophene (2.05 mL, 2.38 g, 18.9 mmol) and p-tolylaldehyde (2.2 mL, 18.9 mmol) afforded chalcone (E)-1-(thiophen-2-yl)-3-(p-tolyl)prop-2-en-1-one (3.63 g, 15.9 mmol, 84%) as an off-white solid (obtained by precipitation). The $^1$H-NMR spectrum was in accordance with the chemical structure.

The reaction of chalcone (E)-1-(thiophen-2-yl)-3-(p-tolyl)prop-2-en-1-one (1.0 g, 4.38 mmol) with 1 equivalent 2-cyanothioacetamide afforded the desired thiopyridine derivative that was purified by silica gel chromatography. The pure 6-(thiophen-2-yl)-2-thioxo-4-(p-tolyl)-1,2-dihydro-pyridine-3-carbonitrile was obtained with a 46% yield (620 mg, 2.0 mmol) as an orange solid. The $^1$H-NMR spectrum was in accordance with the chemical structure.

Alkylation of compound 6-(thiophen-2-yl)-2-thioxo-4-(p-tolyl)-1,2-dihydro-pyridine-3-carbonitrile (331 mg, 1.07 mmol) with methyl α-bromophenylacetate (270 mg, 1.18 mmol, 1.1 equiv.) afforded methyl 2-((3-cyano-6-(thiophen-2-yl)-4-(p-tolyl)pyridin-2-yl)thio)-2-phenylacetate in a quantitative yield (515 mg, max. 1.07 mmol) as a brown solid. The $^1$H-NMR spectrum was in accordance with the chemical structure.

Saponification of methyl 2-((3-cyano-6-(thiophen-2-yl)-4-(p-tolyl)pyridin-2-yl)thio)-2-phenylacetate (515 mg, 1.13 mmol) with 1N NaOH in THF-methanol mixture afforded final product 2-((3-cyano-6-(thiophen-2-yl)-4-(p-tolyl)pyridin-2-yl)thio)-2-phenylacetic acid (18.2 mg, 0.04 mmol, yield 4%) as a tan solid with an HPLC purity of 95.4%. LC-MS [M+H] 443.1 ($C_{25}H_{18}N_2O_2S_2$+H, requires 443.08). The $^1$H-NMR spectrum was in accordance with the chemical structure.

Example 15

Preparation of 2-((3-cyano-4-(4-fluorophenyl)-6-(thiophen-2-yl) pyridin-2-yl)thio)-2-phenylacetic acid (Formula Ia-xxii)

The reaction of 2-acetylthiophene (2.05 mL, 2.38 g, 18.9 mmol) and p-fluorbenzaldehyde (2.35 g, 18.9 mmol) afforded chalcone (E)-3-(4-fluorophenyl)-1-(thiophen-2-yl)prop-2-en-1-one (4.03 g, 17.3 mmol, 92%) as an off-white solid (obtained by precipitation). The $^1$H-NMR spectrum was in accordance with the chemical structure.

The reaction of chalcone (E)-3-(4-fluorophenyl)-1-(thiophen-2-yl)prop-2-en-1-one with 1 equivalent of 2-cyanothioacetamide afforded the desired 4-(4-fluorophenyl)-6-(thiophen-2-yl)-2-thioxo-1,2-dihydropyridine-3-carbonitrile with a 10% yield (136 mg, 0.44 mmol) as an orange solid, which was used as such in the next reaction. The $^1$H-NMR spectrum was in accordance with the chemical structure.

Alkylation of 4-(4-fluorophenyl)-6-(thiophen-2-yl)-2-thioxo-1,2-dihydropyridine-3-carbonitrile (136 mg, 0.44 mmol) with methyl α-bromophenylacetate (110 mg, 0.48 mmol, 1.1 equiv.) afforded methyl 2-((3-cyano-4-(4-fluorophenyl)-6-(thiophen-2-yl)pyridin-2-yl)thio)-2-phenylacetate (60 mg, 0.13 mmol, yield 30%) as a brown solid. The $^1$H-NMR spectrum was in accordance with the chemical structure.

Saponification of methyl 2-((3-cyano-4-(4-fluorophenyl)-6-(thiophen-2-yl)pyridin-2-yl)thio)-2-phenylacetate (515 mg, 1.13 mmol) with 1N NaOH in a THF-methanol mixture afforded 2-((3-Cyano-4-(4-fluorophenyl)-6-(thiophen-2-yl)pyridin-2-yl)thio)-2-phenylacetic acid (18.17 mg, 0.04 mmol, yield 31%) as a tan solid with an HPLC purity of 98.5%. LC-MS [M+H] 447.1 ($C_{24}H_{15}FN_2O_2S_2$+H, requires 447.06). The $^1$H-NMR spectrum was in accordance with the chemical structure.

Example 16

Preparation of 2-((4-(4-bromophenyl)-3-cyano-6-(thiophen-2-yl) pyridin-2-yl)thio)-2-phenylacetic acid (Formula Ia-xxiii)

The reaction of 2-acetylthiophene (2.05 mL, 2.38 g, 18.9 mmol) and 4-bromobenzaldehyde (3.5 g, 18.9 mmol) afforded chalcone (E)-3-(4-bromophenyl)-1-(thiophen-2-yl)prop-2-en-1-one (4.99 g, 17.1 mmol, 90%) as an off-white solid (Obtained by precipitation). The $^1$H-NMR spectrum was in accordance with the chemical structure.

The reaction of chalcone (E)-3-(4-bromophenyl)-1-(thiophen-2-yl)prop-2-en-1-one (1.0 g, 3.4 mmol) with 1 equivalent 2-cyanothioacetamide afforded the desired 4-(4-bromophenyl)-6-(thiophen-2-yl)-2-thioxo-1,2-dihydropyridine-3-carbonitrile with a 12% yield ((152 mg, 0.41 mmol) as an orange solid which was used as such in the next reaction. The $^1$H-NMR spectrum was in accordance with the chemical structure.

Alkylation of 4-(4-bromophenyl)-6-(thiophen-2-yl)-2-thioxo-1,2-dihydropyridine-3-carbonitrile (152 mg, 0.41 mmol) with methyl α-bromophenylacetate (110 mg, 0.48 mmol, 1.1 equiv.) afforded methyl 2-((4-(4-bromophenyl)-3-cyano-6-(thiophen-2-yl)pyridin-2-yl)thio)-2-phenylacetate (74 mg, 0.14 mmol, yield 35%) as a yellow solid. The $^1$H-NMR spectrum was in accordance with the chemical structure.

Saponification of methyl 2-((4-(4-bromophenyl)-3-cyano-6-(thiophen-2-yl)pyridin-2-yl)thio)-2-phenylacetate (74 mg, 0.14 mmol) with 1N NaOH in THF-methanol mixture afforded 2-((4-(4-bromophenyl)-3-cyano-6-(thiophen-2-yl)pyridin-2-yl)thio)-2-phenylacetic acid (0.4 mg, 0.8 μmol, yield 0.6%) as a tan solid with an HPLC purity of 81%. LC-MS [M+H] 507/509 ($C_{24}H_{15}BrN_2O_2S_2$+H, requires 506.98/508.98). The $^1$H-NMR spectrum was in accordance with the chemical structure.

Example 17

Preparation of 2-((3-cyano-6-(furan-2-yl)-4-(thiophen-2-yl) pyridin-2-yl)thio)-2-phenylacetic acid (Formula Ia-xxiv)

The reaction of 2-acetylthiophene (2.5 g, 19.8 mmol) and 2-furaldehyde (1.9 g, 19.8 mmol) afforded chalcone (E)-3-(furan-2-yl)-1-(thiophen-2-yl)prop-2-en-1-one (3.66 g, 17.9 mmol, 90%) as an orange oil, which solidified overnight (purification by column chromatography). The $^1$H-NMR spectrum was in accordance with the chemical structure.

The reaction of chalcone (E)-3-(furan-2-yl)-1-(thiophen-2-yl)prop-2-en-1-one (2.8 g, 13.7 mmol) with 1 equivalent 2-cyanothioacetamide afforded the desired 6-(Furan-2-yl)-4-(thiophen-2-yl)-2-thioxo-1,2-dihydropyridine-3-carbonitrile with a 22% yield (863 mg, 3.0 mmol) as an orange solid. The $^1$H-NMR spectrum was in accordance with the chemical structure.

Alkylation of 6-(furan-2-yl)-4-(thiophen-2-yl)-2-thioxo-1,2-dihydropyridine-3-carbonitrile with (863 mg, 3.0 mmol) methyl α-bromophenylacetate (765 mg, 3.3 mmol, 1.1 equiv.) afforded methyl 2-((3-cyano-6-(furan-2-yl)-4-(thiophen-2-yl)pyridin-2-yl)thio)-2-phenylacetate (1.3 g, 3.0 mmol, yield 99%) as a yellow solid. The $^1$H-NMR spectrum was in accordance with the chemical structure.

Saponification of methyl 2-((3-cyano-6-(furan-2-yl)-4-(thiophen-2-yl)pyridin-2-yl)thio)-2-phenylacetate (392 mg, 0.91 mmol) with 1N NaOH in THF-methanol mixture afforded 2-((3-Cyano-6-(furan-2-yl)-4-(thiophen-2-yl)pyridin-2-yl)thio)-2-phenylacetic acid (112.11 mg, 0.27 mmol, yield 30%) as a tan solid with as a grey solid with an HPLC purity of 96.2%. LC-MS [M+H] 419 ($C_{22}H_{14}N_2O_3S_2$+H, requires 419.04). The $^1$H-NMR spectrum was in accordance with the chemical structure.

Example 18

Preparation of 2-((3-cyano-4,6-di(furan-2-yl)pyridin-2-yl)thio)-2-phenylacetic acid (Formula Ia-xxv)

The reaction of furylmethylketone (2.5 g, 22.7 mmol) and 2-furaldehyde (2.2 g, 22.7 mmol) afforded chalcone (E)-1,3-di(furan-2-yl)prop-2-en-1-one (3.33 g, 17.7 mmol, yield 78%) as an yellow solid (obtained by precipitation). The $^1$H-NMR spectrum was in accordance with the chemical structure.

The reaction of chalcone (E)-1,3-di(furan-2-yl)prop-2-en-1-one (1.75 g, 9.3 mmol) with 1 equivalent 2-cyanothioacetamide afforded the desired 4,6-Di(furan-2-yl)-2-thioxo-1,2-dihydropyridine-3-carbonitrile with a 29% yield (720 mg, 2.7 mmol) as an orange solid. The $^1$H-NMR spectrum was in accordance with the chemical structure.

Alkylation of 4,6-di(furan-2-yl)-2-thioxo-1,2-dihydropyridine-3-carbonitrile (1.5 mmol) with methyl α-bromophenylacetate (1.7 mmol, 1.1 equiv.) afforded the desired methyl 2-((3-cyano-4,6-di(furan-2-yl)pyridin-2-yl)thio)-2-phenylacetate in a 80% yield that was used as is in the next step.

Saponification of methyl 2-((3-cyano-4,6-di(furan-2-yl)pyridin-2-yl)thio)-2-phenylacetate (500 mg, 1.2 mmol) with 1N NaOH in THF-methanol mixture afforded 2-((3-cyano-4,6-di(furan-2-yl)pyridin-2-yl)thio)-2-phenyl acetic acid (191 mg, 0.47 mmol, yield 40%) as a grey solid with an HPLC purity of 97.8%. LC-MS [M+H] 403.1 ($C_{22}H_{14}N_2O_4S$+H, requires 403.07). The $^1$H-NMR spectrum was in accordance with the chemical structure.

Example 19

Preparation of 2-((3-cyano-4-(furan-2-yl)-6-(thiophen-2-yl) pyridin-2-yl)thio)-2-phenylacetic acid (Formula Ia-xxxii)

The reaction of 2-acetylthiophene (2.5 g, 19.8 mmol) and 2-furaldehyde (1.9 g, 19.8 mmol) afforded chalcone (E)-3-(furan-2-yl)-1-(thiophen-2-yl)prop-2-en-1-one (3.66 g, 17.9 mmol, yield 90%) as an orange oil, which solidified overnight (purification by column chromatography). The $^1$H-NMR spectrum was in accordance with the chemical structure.

The reaction of chalcone (E)-3-(furan-2-yl)-1-(thiophen-2-yl)prop-2-en-1-one (3.66 g, 17.9 mmol) with 1 equivalent 2-cyanothioacetamide afforded the desired 4-(Furan-2-yl)-6-(thiophen-2-yl)-2-thioxo-1,2-dihydropyridine-3-carbonitrile with a 39% yield (2.0 g, 7.0 mmol) as an orange solid. The $^1$H-NMR spectrum was in accordance with the chemical structure.

Alkylation of 4-(furan-2-yl)-6-(thiophen-2-yl)-2-thioxo-1,2-dihydropyridine-3-carbonitrile with (1.0 mmol) with methyl α-bromophenylacetate (1.1 mmol, 1.1 equiv.) afforded the desired methyl 2-((3-cyano-4-(furan-2-yl)-6-(thiophen-2-yl)pyridin-2-yl)thio)-2-phenylacetic acetate in a 76% yield.

Saponification of methyl 2-((3-cyano-4-(furan-2-yl)-6-(thiophen-2-yl)pyridin-2-yl)thio)-2-phenylacetic acetate (319 mg, 0.76 mmol) with 1N NaOH in THF-methanol mixture afforded 2-((3-cyano-4-(furan-2-yl)-6-(thiophen-2-yl)pyridin-2-yl)thio)-2-phenylacetic acid (94.9 mg, 0.227 mmol, yield 30%) as a grey solid with an HPLC purity of 96.9%. LC-MS [M+H] 419 ($C_{22}H_{14}N_2O_3S_2$+H, requires 419.04). The $^1$H-NMR spectrum was in accordance with the chemical structure.

Example 20

Preparation of 2-((3-cyano-4-(4-methoxyphenyl)-6-(thiophen-2-yl) pyridin-2-yl)thio)butanoic acid (Formula Ia-xxix)

The reaction of 2-acetylthiophene (2.05 mL, 2.38 g, 18.9 mmol) and p-anisaldehyde (2.3 mL, 18.9 mmol) afforded chalcone (E)-3-(4-methoxyphenyl)-1-(thiophen-2-yl)prop-2-en-1-one (4.13 g, 16.9 mmol, 89%) as an off-white solid (obtained by precipitation).

The reaction of chalcone 4-(4-methoxyphenyl)-6-(thiophen-2-yl)-2-thioxo-1,2-dihydropyridine-3-carbonitrile (1.5 g, 6.1 mmol) with 1 equivalent 2-cyanothioacetamide afforded the desired 4-(4-methoxyphenyl)-6-(thiophen-2-yl)-2-thioxo-1,2-dihydropyridine-3-carbonitrile with a 24% yield (470 mg, 1.4 mmol) as an orange solid. The $^1$H-NMR spectrum was in accordance with the chemical structure.

Alkylation of 4-(4-methoxyphenyl)-6-(thiophen-2-yl)-2-thioxo-1,2-dihydropyridine-3-carbonitrile (200 mg, 0.62 mmol) with 2-bromobutyric acid methyl ester (0.68 mmol, 1.1 equiv.) afforded the desired methyl 2-((3-cyano-4-(4-methoxyphenyl)-6-(thiophen-2-yl)pyridin-2-yl)thio)butanoate (221 mg, 0.52 mmol, yield 76%) as a yellow solid. The $^1$H-NMR spectrum was in accordance with the chemical structure.

Saponification of methyl 2-((3-cyano-4-(4-methoxyphenyl)-6-(thiophen-2-yl)pyridin-2-yl)thio)butanoate (221 mg, 0.50 mmol) with 1N NaOH in THF-methanol mixture afforded the crude desired product that was purified by preparative HPLC chromatography. The purified 2-((3-cyano-4-(4-methoxyphenyl)-6-(thiophen-2-yl)pyridin-2-yl)thio)butanoic acid (68.9 mg, 0.17 mmol) was obtained in 32% yield as an off-white solid with an HPLC purity of 95.2%. LC-MS [M+H] 411.0 ($C_{21}H_{18}N_2O_3S_2$+H, requires 411.08). The $^1$H-NMR spectrum was in accordance with the chemical structure.

Example 21

Preparation of 2-((3-cyano-4-(4-methoxyphenyl)-6-(thiophen-2-yl) pyridin-2-yl)thio)-2-phenylacetamide (Formula Ib-ii)

A mixture of methyl 2-((3-cyano-4-(4-methoxyphenyl)-6-(thiophen-2-yl)pyridin-2-yl)thio)-2-phenylacetate (prepared as described in Example 4) (100 mg, 0.212 mmol) and 7N $NH_3$ in methanol (10 mL) was stirred at 50° C. in a pressure tube for 2 days. The mixture was concentrated and triturated with ethyl acetate to yield final product 2-((3-cyano-4-(4-methoxyphenyl)-6-(thiophen-2-yl)pyridin-2-yl)thio)-2-phenylacetamide (30 mg, 0.065 mmol, yield 31%) as a tan solid with an HPLC purity of 97.0%. LC-MS [M+H]

458.1 ($C_{25}H_{19}N_3O_2S_2$+H, requires 458.09). The $^1$H-NMR spectrum was in accordance with the chemical structure.

Example 22

Preparation of 2-((3-cyano-4-(4-methoxyphenyl)-6-(thiophen-2-yl) pyridin-2-yl)thio)-N-hydroxy-2-phenylacetamide (Formula Ib-iii)

A mixture of methyl 2-((3-cyano-4-(4-methoxyphenyl)-6-(thiophen-2-yl)pyridin-2-yl)thio)-2-phenylacetate (prepared as described in Example 4) (100 mg, 0.212 mmol), 50% aqueous $NH_2OH$ (1.0 mL), 1M NaOH (0.41 mL, 0.42 mmol) in THF (1 mL) was stirred for 3 days at room temperature. The mixture was diluted with $H_2O$ (3 mL) and extracted with ethyl acetate (2×10 mL). The combined organic layers were dried over $Na_2SO_4$ and the solvent evaporated in vacuo. The residue was purified by preparative HPLC (reversed phase, acetonitrile, aqueous ($NH_4$)$HCO_3$) and the product fractions were lyophilized to give the desired 2-((3-cyano-4-(4-methoxyphenyl)-6-(thiophen-2-yl) pyridin-2-yl)thio)-N-hydroxy-2-phenylacetamide (50 mg, 0.106 mmol, 50%) as a fluffy off-white solid with an HPLC purity of 97.3%. LC-MS [M+H] 474.0 ($C_{25}H_{19}N_3O_3S_2$+H, requires 474.09). The $^1$H-NMR spectrum was in accordance with the chemical structure.

Example 23

Preparation of 2-((2-hydroxy-1-phenylethyl)thio)-4-(4-methoxyphenyl) -6-(thiophen-2-yl)nicotinonitrile (Formula IIb-i)

A mixture of 4-(4-methoxyphenyl)-6-(thiophen-2-yl)-2-thioxo-1,2-dihydropyridine-3-carbonitrile (prepared as described in Example 4) (156 mg, 0.48 mmol), $K_2CO_3$ (73 mg, 0.528 mmol, 1.1 equiv.) and 2-bromo-2-phenyl-ethanol (107 mg, 0.53 mmol, 1.1 equiv.) in acetone was refluxed for 3 hours. After cooling to room temperature, the mixture was filtered and the solvent was evaporated in vacuo. Purification by repeated automated column chromatography on the ISCO-companion ($SiO_2$, gradient ethyl acetate/heptane) gave 2-((2-hydroxy-1-phenylethyl)thio)-4-(4-methoxyphenyl)-6-(thiophen-2-yl)nicotinonitrile (135 mg, 0.30 mmol, yield 63%) as an off-white solid with an HPLC purity of 97.4%. LC-MS [M+H] 445 ($C_{25}H_{20}N_2O_2S_2$+H, requires 445.1). The $^1$H-NMR spectrum was in accordance with the chemical structure.

Example 24

Preparation of 2-((3-cyano-4-(thiophen-2-yl)-5,6,7,8-tetrahydroquinolin-2-yl) thio)-2-phenylacetic acid (Formula Ia-xii)

A mixture of thiophene-2-carboxaldehyde (0.93 mL, 1.12 g, 10.0 mmol), 2-cyanothioacetamide (1.0 g, 10.0 mmol) and 2 drops of $NEt_3$ (12 mL) was refluxed for 25 min. The mixture was cooled to room temperature and filtered. The solid was washed with ethanol (20 mL) and dried in air to give the desired alkene as yellow crystals (1.5 g, 7.7 mmol, 77%). A mixture of these crystals, cyclohexanone (0.88 mL, 833 mg, 8.5 mmol, 1.1 equiv.) and 3 drops of piperidine in ethanol (50 mL) was refluxed for 3 hours. It was concentrated in vacuo until ~25 mL of solvent were left. The mixture was cooled to room temperature and left for ~2 h. The resulting solid was filtered off, washed with ethanol (10 mL) and heptane (50 mL) and dried in air to give 2-mercapto-4-(thiophen-2-yl)-5,6,7,8-tetrahydroquinoline-3-carbonitrile (586 mg, 2.15 mmol, 28%) as an orange solid. The $^1$H-NMR spectrum was in accordance with the chemical structure.

A mixture of 2-mercapto-4-(thiophen-2-yl)-5,6,7,8-tetrahydroquinoline-3-carbonitrile (272 mg, 1.0 mmol), $K_2CO_3$ (152 mg, 1.1 mmol) and methyl α-bromophenylacetate (229 mg, 1.0 mmol) in acetone (15 mL) was refluxed for 2 hours. The mixture was cooled to room temperature and filtered. The solvent was removed in vacuo and the residue was purified by automated column chromatography on the ISCO-companion ($SiO_2$, gradient ethyl acetate/heptane) to give methyl 2-((3-cyano-4-(thiophen-2-yl)-5,6,7,8-tetrahydroquinolin-2-yl)thio)-2-phenylacetate (276 mg, 0.66 mmol, 65%) as a yellowish solid. The $^1$H-NMR spectrum was in accordance with the chemical structure.

A mixture of methyl 2-((3-cyano-4-(thiophen-2-yl)-5,6,7,8-tetrahydroquinolin-2-yl)thio)-2-phenylacetate (276 mmol, 0.656 mmol) in THF (2 mL), methanol (2 mL) and 2N NaOH (2 mL) was stirred for 2 hours at room temperature. After completion of the reaction, the organic solvent was removed in vacuo and the aqueous residue was diluted with $H_2O$ (5 mL). The pH was adjusted to 5 by addition of 1M HCl. The solid was filtered off, washed with $H_2O$ (3×10 mL) and dried in air to give the crude 2-((3-cyano-4-(thiophen-2-yl)-5,6,7,8-tetrahydroquinolin-2-yl)thio)-2-phenylacetic acid as a tan solid.

The racemic acid product was separated into enantiomers by preparative HPLC on a chiral stationary column (Chiralpak IC-column, 20×250 mm, Flow rate at 17 ml/min) using as a mobile phase a mixture of heptane/ethanol/trifluoroacetic acid (80/20/02) to yield (73.6 mg, 0.18 mmol, 28%) of enantiomer 1 (Formula Ia-xii-e1) as an off-white solid and (97.2 mg, 0.24 mmol, 36%) of enantiomer 2 (Formula Ia-xii-e2) as an off-white soild. Both enantiomers were analyzed for enantiomeric purity by HPLC using Chiralpak IC-column (0.46×25) and as a mobile phase a mixture of heptane/ethanol/trifluoroacetic acid (80/20/02) at 0.7 ml/min flow rate. The enantiomeric excess (ee) of the Enantiomer 1 (Formula Ia-xii-e1) that was eluted at $R_t$=14.18 min was determined to be 72.1% and Enantiomer 2 (Formula Ia-xii-e2) that was eluted at $R_t$=18.18 min was 65.8%, respectively. LC-MS and the $^1$H-NMR spectra for both enantiomers are in accordance with the chemical structure. LC-MS LC-MS [M+H] 407 ($C_{22}H_{18}N_2O_2S_2$+H, requires 407.08).

Example 25

Preparation of 2-((3-cyano-4-phenyl-5,6,7,8-tetrahydroquinolin-2-yl) thio)-2-phenylacetic acid (Formula Ia-xvii)

A mixture of benzaldehyde (605 mg, 5.7 mmol), malononitrile (376 mg, 5.7 mmol), 2-cyanothioacetamide (570 mg, 5.7 mmol) and three drops of piperidine in ethanol (25 mL) was refluxed for 5 hours. $H_2O$ (25 mL) was added and the solid was filtered off and washed with $H_2O$ (2×50 ml) and dried in air to give 2,6-diamino-4-phenyl-4H-thiopyran-3,5-dicarbonitrile (1.12 g, 4.4 mmol, 77%) as a tan solid. The $^1$H-NMR spectrum was in accordance with the chemical structure.

A mixture of 2,6-diamino-4-phenyl-4H-thiopyran-3,5-dicarbonitrile (1.12 g, 4.4 mmol) and 4-(1-cyclohexen-1-yl) morpholine (0.71 mL, 721 mg, 4.4 mmol) in ethanol (50 mL) was refluxed for 2 hours. The mixture was cooled to room temperature and the pH was adjusted to 5 by addition of 6M HCl. The mixture was stirred overnight at room temperature, concentrated to half-volume in vacuo and filtered. H$_2$O (25 mL) was added and the resulting solid was washed with H$_2$O (25 mL), acetic acid (25 mL) and heptane (50 mL) and dried in air to give a yellow solid. Recrystallization from acetic acid (10 mL) gave, after filtration, washing with acetic acid (5 mL) and heptane (25 mL) and drying in air, 2-mercapto-4-phenyl-5,6,7,8-tetrahydroquinoline-3-carbonitrile (325 mg, 1.21 mmol, 28%) as a yellow solid. The $^1$H-NMR spectrum was in accordance with the chemical structure.

A mixture of 2-mercapto-4-phenyl-5,6,7,8-tetrahydroquinoline-3-carbonitrile (266 mg, 1.0 mmol), K$_2$CO$_3$ (152 mg, 1.1 mmol) and methyl α-bromophenylacetate (229 mg, 1.0 mmol) in acetone (15 mL) was refluxed for 2 hours. The mixture was cooled to room temperature and filtered. The solvent was removed in vacuo and the residue was purified by automated column chromatography on the ISCO-companion (SiO$_2$, gradient ethyl acetate/heptane) to give methyl 2-((3-cyano-4-phenyl-5,6,7,8-tetrahydroquinolin-2-yl)thio)-2-phenylacetate (276 mg, 0.66 mmol, yield 65%) as a yellowish solid. The $^1$H-NMR spectrum was in accordance with the chemical structure.

A mixture of methyl 2-((3-cyano-4-phenyl-5,6,7,8-tetrahydroquinolin-2-yl)thio)-2-phenylacetate (280 mg, 0.67 mmol) in THF (2 mL), methanol (2 mL) and 2M LiOH (2 mL) was stirred for 2 hours at room temperature. After completion of the reaction, the solvent was removed in vacuo and the residue was stirred in ethyl acetate (10 mL). The solid was filtered and washed with ethyl acetate (3×5 mL) and dried in air. It was dissolved in H$_2$O (5 mL) and the pH of the solution was adjusted to 5 by addition of 1M HCl. The resulting solid was filtered and washed with H$_2$O (3×10 mL) and dried in air to give the desired 2-((3-Cyano-4-phenyl-5,6,7,8-tetrahydroquinolin-2-yl)thio)-2-phenylacetic acid (150 mg, 0.375 mmol, yield 6%) as an off-white solid with an HPLC purity of 99.5%. LC-MS [M+H] 401 (C$_{24}$H$_{20}$N$_2$O$_2$S+H, requires 401.12). The $^1$H-NMR spectrum was in accordance with the chemical structure.

Example 26

Preparation of 2-((4-(4-chlorophenyl)-3-cyano-5,6,7,8-tetrahydroquinolin-2-yl) thio)-2-phenylacetic acid (Formula Ia-xviii)

A mixture of 4-chlorobenzaldehyde (562 mg, 5.0 mmol), malononitrile (330 mg, 5.0 mmol), 2-cyanothioacetamide (500 mg, 5.0 mmol) and three drops of piperidine in ethanol (25 mL) was refluxed for 5 hours. H$_2$O (25 mL) was added and the solid was filtered off and washed with H$_2$O (2×50 ml) and dried in air to give 2,6-diamino-4-(4-chlorophenyl)-4H-thiopyran-3,5-dicarbonitrile (1.07 g, 3.8 mmol, 76%) as a yellow solid. The $^1$H-NMR spectrum was in accordance with the chemical structure.

A mixture of 2,6-diamino-4-(4-chlorophenyl)-4H-thiopyran-3,5-dicarbonitrile (1.07 g, 3.7 mmol) and 4-(1-cyclohexen-1-yl)morpholine (0.62 mL, 620 mg, 3.7 mmol) in ethanol (25 mL) was refluxed for 2 hours. The mixture was cooled to room temperature and the pH was adjusted to 5 by addition of 6M HCl. The mixture was stirred overnight at room temperature, concentrated to half-volume in vacuo and filtered. The solid was washed with H$_2$O (25 mL) and heptane (50 mL) and dried in air to give an orange solid. Recrystallization from acetic acid (10 mL) gave, after filtration, washing with acetic acid (5 mL) and heptane (25 mL) and drying in air, compound 2-mercapto-4-(4-chlorophenyl)-5,6,7,8-tetrahydroquinoline-3-carbonitrile (325 mg, 1.08 mmol, yield 29%) as a yellow solid. The $^1$H-NMR spectrum was in accordance with the chemical structure.

A mixture of 2-mercapto-4-phenyl-5,6,7,8-tetrahydroquinoline-3-carbonitrile (300 mg, 1.0 mmol), K$_2$CO$_3$ (152 mg, 1.1 mmol) and methyl α-bromophenylacetate (229 mg, 1.0 mmol) in acetone (15 mL) was refluxed for 2 hours. The mixture was cooled to room temperature and filtered. The solvent was removed in vacuo to give the desired methyl 2-((3-cyano-4-(4-chlorophenyl)-5,6,7,8-tetrahydroquinolin-2-yl)thio)-2-phenylacetate (463 mg, 1.0 mmol, yield 100%) as a as a brownish foam, that was used in the next step without further purification. The $^1$H-NMR spectrum was in accordance with the chemical structure.

A mixture of methyl 2-((3-cyano-4-(4-chlorophenyl)-5,6,7,8-tetrahydroquinolin-2-yl)thio)-2-phenylacetate (463 mg, 1.0 mmol) in THF (2 mL), methanol (2 mL) and 2M NaOH (2 mL) was stirred for 3 hours at room temperature. After completion of the reaction, the organic solvent was removed in vacuo and the aqueous residue was diluted with H$_2$O (5 mL). The pH was adjusted to 5 by addition of 1M HCl. The solid was filtered off, washed with H$_2$O (3×10 mL) and dried in air to give the crude acid as a tan solid. Purification by repeated automated column chromatography on the ISCO-companion (SiO$_2$, gradient CH$_2$Cl$_2$/methanol) gave 2-((4-(4-Chlorophenyl)-3-cyano-5,6,7,8-tetrahydroquinolin-2-yl) thio)-2-phenylacetic acid (61 mg, 0.14 mmol, yield 14%) as a pinkish foam with an HPLC purity of 99.8%. LC-MS [M+H] 435 (C$_{24}$H$_{19}$ClN$_2$O$_2$S+H, requires 435.09). The $^1$H-NMR spectrum was in accordance with the chemical structure.

Example 27

Preparation of 2-((3-cyano-4-(4-methoxyphenyl)-5,6,7,8-tetrahydroquinolin-2-yl) thio)-2-phenylacetic acid (Formula Ia-xxvi)

A mixture of p-anisaldehyde (681 mg, 5.0 mmol), malononitrile (330 mg, 5.0 mmol), 2-cyanothioacetamide (500 mg, 5.0 mmol) and three drops of piperidine in ethanol (25 mL) was refluxed for 5 hours. H$_2$O (25 mL) was added and the solid was filtered off and washed with H$_2$O (2×50 ml) and dried in air to give 2,6-diamino-4-(4-methoxyphenyl)-4H-thiopyran-3,5-dicarbonitrile (570 mg, 2.0 mmol, yield 40%) as a tan solid. The $^1$H-NMR spectrum was in accordance with the chemical structure.

A mixture of 2,6-diamino-4-(4-methoxyphenyl)-4H-thiopyran-3,5-dicarbonitrile (570 mg, 1.97 mmol) and 4-(1-cyclohexen-1-yl)morpholine (0.32 mL, 330 mg, 1.97 mmol) in ethanol (10 mL) was refluxed for 2 hours. The mixture was cooled to room temperature and the pH was adjusted to 5 by addition of 6M HCl. The mixture was stirred for 2 d at room temperature and filtered. The solid was washed with H$_2$O (25 mL) and heptane (50 mL) and dried in air to give the desired 2-mercapto-4-(4-methoxyphenyl)-5,6,7,8-tetrahydroquinoline-3-carbonitrile (210 mg, 0.7 mmol, yield 35%) as a yellow solid. The $^1$H-NMR spectrum was in accordance with the chemical structure.

Alkylation of 2-mercapto-4-(4-methoxyphenyl)-5,6,7,8-tetrahydroquinoline-3-carbonitrile (210 mg, 0.71 mmol) with methyl alpha-bromophenylacetate (0.78 mmol, 1.1 eq) in presence of K$_2$CO$_3$ in acetone gave compound the desired product as a colorless oil, after purification by automated column chromatography on the ISCO-companion (SiO$_2$, gradient ethyl acetate/heptane). Additional purification was achieved by triturition from methanol (2 mL). Filtration of the solid, washing with a small volume of methanol (1 mL) and drying in air afforded methyl 2-((3-cyano-4-(4-methoxyphenyl)-5,6,7,8-tetrahydroquinolin-2-yl)thio)-2-phenylacetate (160 mg, 0356 mmol, yield 50%) as a white solid. The $^1$H-NMR spectrum was in accordance with the chemical structure.

A mixture of methyl 2-((3-cyano-4-(4-methoxyphenyl)-5,6,7,8-tetrahydroquinolin-2-yl)thio)-2-phenylacetate (288 mg, 0.65 mmol) in THF (2 mL), methanol (2 mL) and 2M NaOH (1.3 mL) was stirred for 18 hours at room temperature. After completion of the reaction, the solvent was removed in vacuo and the residue was stirred in ethyl acetate (10 mL). The solid was filtered and washed with ethyl acetate (3×5 mL) and dried in air. It was dissolved in $H_2O$ (5 mL) and the pH of the solution was adjusted to 5 by addition of 1M HCl. The resulting solid was filtered and washed with $H_2O$ (3×10 mL) and dried in air to give 24(3-Cyano-4-(4-methoxyphenyl)-5,6,7,8-tetrahydroquinolin-2-yl)thio)-2-phenylacetic acid (125 mg, 0.29 mmol, yield 45%) as an off-white solid as an of with an HPLC purity of 99.9%. LC-MS [M+H] 431 ($C_{25}H_{22}N_2O_3S$+H, requires 431.14). The $^1$H-NMR spectrum was in accordance with the chemical structure.

Example 28

Preparation of 2-((3-cyano-4-(thiophen-2-yl)-5,6,7,8-tetrahydroquinolin-2-yl) oxy)-2-phenylacetic acid (Formula Ia-xxvii)

A mixture of thiophene-2-carboxaldehyde (1.9 mL, 2.24 g, 20 mmol), ethyl cyanoacetate (2.1 mL, 2.26 g, 20 mmol) and 3 drops of piperidine in ethanol (30 mL) was stirred for 2 hours. The solid was filtered off, washed with a little ethanol and dried in air to give (E)-ethyl 2-cyano-3-(thiophen-2-yl)acrylate (3.1 g, 14.9 mmol, 75%) as off-white crystals.

A mixture of (E)-ethyl 2-cyano-3-(thiophen-2-yl)acrylate (1.5 g, 7.2 mmol), cyclohexanone (0.75 mL, 710 mg, 7.2 mmol), $NH_4OAc$ (210 mg, 3.65 mmol) in ethanol (10 mL) was refluxed overnight. The mixture was cooled to room temperature and the resulting solid was filtered off, washed with some ethanol (2 mL) and dried in air to give 2-hydroxy-4-(thiophen-2-yl)-5,6,7,8-tetrahydro-quinoline-3-carbonitrile (70 mg, 0.27 mmol, 3.8%) as a yellow solid.

A mixture of 2-hydroxy-4-(thiophen-2-yl)-5,6,7,8-tetrahydroquinoline-3-carbonitrile (70 mg, 0.27 mmol), $K_2CO_3$ (56 mg, 0.405 mmol) and methyl α-bromophenylacetate (62 mg, 0.27 mmol) in acetone (10 mL) was refluxed for 18 hours. The mixture was cooled to room temperature and filtered. The solvent was removed in vacuo and the residue was purified by automated column chromatography on the ISCO-companion ($SiO_2$, gradient ethyl acetate/heptane) to give methyl 2-((3-cyano-4-(thiophen-2-yl)-5,6,7,8-tetrahydroquinolin-2-yl)oxy)-2-phenylacetate (60 mg, 0.148 mmol, 55%) as a white solid.

A mixture of methyl 2-((3-cyano-4-(thiophen-2-yl)-5,6,7,8-tetrahydroquinolin-2-yl)oxy)-2-phenylacetate (60 mmol, 0.148 mmol) in THF (1 mL), methanol (1 mL) and 2M NaOH (1 mL) was stirred for 2 hours at room temperature. After completion of the reaction, the solvents were removed in vacuo and the solid residue was stirred in ethyl acetate (10 mL). The solid was filtered off and the filtrate was concentrated in vacuo and taken up in $H_2O$ (5 mL). The pH was adjusted to 5 by addition of 1M HCl. The solid was filtered off, washed with $H_2O$ (3×10 mL) and dried in air to give 2-((3-cyano-4-(thiophen-2-yl)-5,6,7,8-tetrahydroquinolin-2-yl)oxy)-2-phenylacetic acid (50 mg, 0128 mmol, yield 87%) as an off-white solid with an HPLC purity of 96.5%. LC-MS [M+H] 391 ($C_{22}H_{18}N_2O_3S$+H, requires 391.1). The $^1$H-NMR spectrum was in accordance with the chemical structure.

Example 29

Preparation of 2-((3-cyano-4-(thiophen-2-yl)-5,6,7,8-tetrahydroquinolin-2-yl) thio)-2-phenylacetamide (Formula Ib-i)

A mixture of methyl 2-((3-cyano-4-(thiophen-2-yl)-5,6,7,8-tetrahydroquinolin-2-yl)thio)-2-phenylacetate (prepared as described in Example 18) (124 mg, 0.29 mmol) in 7N $NH_3$ in methanol (10 mL) was stirred for 3 d at room temperature. After 3 d the mixture had become clear and the solvent was evaporated in vacuo. The residue was stirred in ethyl acetate (5 mL) and filtered, washed with a little ethyl acetate (5 mL) and dried in air to give 2-((3-cyano-4-(thiophen-2-yl)-5,6,7,8-tetrahydroquinolin-2-yl)thio)-2-phenylacetamide (25 mg, 0.062 mmol, 21%) as a yellowish solid with an HPLC purity of 96.3%. LC-MS [M+H] 406 ($C_{22}H_{19}N_3OS_2$+H, requires 406.1). The $^1$H-NMR spectrum was in accordance with the chemical structure.

Example 30

Preparation of 2-((2-hydroxy-1-phenylethyl)thio)-4-(thiophen-2-yl) -5,6,7,8-tetrahydroquinoline-3-carbonitrile (Formula IIb-ii)

A mixture of thiophene-2-carboxaldehyde (0.93 mL, 1.12 g, 10.0 mmol), 2-cyanothioacetamide (1.0 g, 10.0 mmol) and 2 drops of triethylamine ($NEt_3$) (12 mL) was refluxed for 25 min. The mixture was cooled to room temperature and filtered. The solid was washed with ethanol (20 mL) and dried in air to give the alkene as yellow crystals (1.5 g, 7.7 mmol, 77%). A mixture of these crystals, cyclohexanone (0.88 mL, 833 mg, 8.5 mmol, 1.1 equiv.) and 3 drops of piperidine in ethanol (50 mL) was refluxed for 3 hours. It was concentrated in vacuo until ~25 mL of solvent were left. The mixture was cooled to room temperature and left for ~2 h. The resulting solid was filtered off, washed with ethanol (10 mL) and heptane (50 mL) and dried in air to give 2-mercapto-4-(thiophen-2-yl)-5,6,7,8-tetrahydroquinoline-3-carbonitrile (586 mg, 2.15 mmol, 28%) as an orange solid.

A mixture of 2-mercapto-4-(thiophen-2-yl)-5,6,7,8-tetrahydroquinoline-3-carbonitrile (100 mg, 0.367 mmol), $K_2CO_3$ (56 mg, 0.404 mmol, 1.1 equiv.) and 2-bromo-2-phenylethanol (74 mg, 0.367 mmol) in acetone was refluxed for 3 hours. After cooling to room temperature, the mixture was filtered and the solvent was evaporated in vacuo. Purification by repeated automated column chromatography on the ISCO-companion ($SiO_2$, gradient ethyl acetate/heptane) gave 2-((2-hydroxy-1-phenylethyl)thio)-4-(thiophen-2-yl)-5,6,7,8-tetrahydroquinoline-3-carbonitrile (73 mg, 0.186 mmol, yield 51%) as a yellow solid with an HPLC purity of 95.3%. LC-MS [M+H] 393 ($C_{22}H_{20}N_2OS_2$+H, requires 393.1). The $^1$H-NMR spectrum was in accordance with the chemical structure.

When introducing elements of the present disclosure, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. A method of controlling fungal pathogens, the method comprising administering to a plant, a seed or soil a composition comprising an effective amount of a compound selected from the group consisting of:
   2-((4-(4-chlorophenyl)-3-cyano-6-(thiophen-2-yl)pyridin-2-yl)thio)-2-phenylacetic acid, or a salt thereof,
   2-((3-cyano-6-(thiophen-2-yl)-4-(trifluoromethy)pyridin-2-yl)thio)-2-phenylacetic acid, or a salt thereof,
   2((3-cyano-4,6-di(thiophen-2-yl)pyridin-2-yl)thio)-2-phenylacetic acid, or a salt thereof,
   2-((3-cyano-4-phenyl-6-(thiophen-2-yl)pyridin-2-yl)thio)-2-phenylacetic acid, or a salt thereof,
   2-((3-cyano-4-(4-methoxyphenyl)-6-(thiophen-2-yl)pyridin-2-yl)thio)-2-phenylacetic acid, or a salt thereof,
   2-((3-cyano-8-methyl-4-(thiophen-2-yl)-5,6,7,8-tetrahydro-1,8-naphthyridin-2-yl)thio)-2-phenylacetic acid,
   2-((4-cyano-1-(thiophen-2-yl)-5,6,7,8-tetrahydroisoquinolin-3-yl)thio)-2-phenylacetic acid, or a salt thereof,
   2((3-cyano-6-(2,4-dimethoxyphenyl)-4-(trifluoromethy)pyridin-2-yl)thio)-2-phenylacetic acid, or a salt thereof,
   2-((3-cyano-6-(3,4-dimethoxyphenyl)-4-(trifluoromethyl)pyridin-2-yl)thio)-2-phenylacetic acid, or a salt thereof,
   2-((6-(4-bromophenyl)-3-cyano-4-(trifluoromethyl)pyridin-2-yl)thio)-2-phenylacetic acid, or a salt thereof,
   2-((3-cyano-6-(furan-2-yl)-4-(trifluoromethyl)pyridin-2-yl)thio)-2-phenylacetic acid, or a salt thereof,
   2-((3-cyano-4,6-diphenylpyridin-2-yl)thio)-2-phenylacetic acid, or a salt thereof,
   2-((3-cyano-4-(thiophen-2-yl)-5,6,7,8-tetrahydroquinolin-2-yl)thio)-2-phenylacetic acid, or a salt thereof,
   2-(3-cyano-4-(4-methoxyphenyl)-6-(thiophen-2-yl)pyridin-2-yl)thio)-2-phenylacetic acid, or a salt thereof,
   2((4-cyano-1-ethyl-5,6,7,8-tetrahydroisoquinolin-3-yl)thio)-2-phenylacetic acid, or a salt thereof,
   2-((3-cyano-6-methyl-4-(trifluoromethyl)pyridin-2-yl)thio)-2-phenylacetic acid, or a salt thereof,
   2-((3-cyano-4-phenyl-5,6,7,8-tetrahydroquinolin-2-yl)thio)-2-phenylacetic acid or a salt thereof,
   2-((4-(4-chlorophenyl)-3-cyano-5,6,7,8-tetrahydronaphthalen-2-yl)thio)-2-phenylacetic acid, or a salt thereof,
   2-((4-(4-methoxyphenyl)-6-(thiophen-2-yl)pyridin-2-yl)thio-2-phenylacetic acid, or a salt thereof,
   2-((3-cyano-6-(furan-2-yl)-4-(4-methoxyphenyl)pyridin-2-yl)thio)-2-phenylacetic acid, or a salt thereof,
   2-((3-cyano-6-(thiophen-2-yl)-4-(p-tolyl)pyridin-2-yl)thio)-2-phenylacetic acid, or a salt thereof,
   2-((3-cyano-4-(4-fluorophenyl)-6-(thiophen-2-yl)pyridin-2-yl)thio)-2-phenylacetic acid, or a salt thereof,
   2-((4-(4-bromophenyl)-3-cyano-6-(thiophen-2-yl)pyridin-2-yl)thio)-2-phenylacetic acid, or a salt thereof,
   2-((3-cyano-6-(furan-2-yl)-4-(thiophen-2-yl)pyridin-2-yl)thio)-2-phenylacetic acid, or a salt thereof,
   2-((3-cyano-4,6-di(furan-2-yl)pyridin-2-yl)thio)-2-phenylacetic acid, or a salt thereof,
   2-((3-cyano-4-(4-methoxyphenyl)-5,6,7,8-tetrahydroquinolin-2-yl)thio)-2-phenylacetic acid, or a salt thereof,
   2-((3-cyano-4-(thiophen-2-yl)-5,6,7,8-tetrahydroquinolin-2-yl)oxy)-2-phenylacetic acid, or a salt thereof,
   2-((3-cyano-4-(4-methoxyphenyl)-6-(1-oxidothiophen-2-yl)pyridin-2-yl-oxy-2-phenylacetic acid, or a salt thereof,
   2-((3-cyano-4-(4-methoxyphenyl)-6-(thiophen-2-yl)pyridin-2-yl)thio)butanoic acid, or a salt thereof,
   2-((3-cyano-4-(4-methoxyphenyl)-6-(pyrimidin-2-yl)pyridin-2-yl)thio)-2-phenylacetic acid, or a salt thereof,
   2-(3-cyano-6-(3-methoxy-1-methyl-1H-pyrrol-2-yl)-4-(4-methoxyphenyl)pyridin-2-yl)thio)-2-phenylacetic acid, or a salt thereof,
   2-((3-cyano-4-(furan-2-yl)-6-(thiophen-2-yl)pyridin-2-yl)thio)-2-phenylacetic acid, or a salt thereof,
   2-((3-cyano-4-(thiophen-2-yl)-5,6,7,8-tetrahydroquinolin-2-phenylacetamide, or a salt thereof,
   2-((3-cyano-4-(4-methoxyphenyl)-6-(thiophen-2-y)pyridin-2-yl)thio)-2-phenylacetamide, or a salt thereof,
   2-((3-cyano-4-(4-methoxyphenyl)-6-(thiophen-2-yl)pyridin-2-yl)thio)-N-hydroxy-2-phenylacetamide, or a salt thereof,
   4-(4-methoxyphenyl)-2-((phenyl(1H-tetrazol-5-yl)methyl)thio)-6-(thiophen-2-yl)nicotinonitrile, or a salt thereof,
   (((3-cyano-4-(4-methoxyphenyl)-6-(thiophen-2-yl)pyridin-2 yl)thio)(phenyl)methyl)phosphonic acid, or a salt thereof,
   (((3-cyano-4-(4-methoxyphenyl)-6-(thiophen-2-yl)pyridin-2-yl)thio)(phenyl)methyl)phosphinic acid, or a salt thereof,
   ((3-cyano-4-(4-methoxyphenyl)-6-(thiophen-2-yl)pyridin-2-yl)thio)(phenyl)methanesulfonic acid, or a salt thereof,
   ((3-cyano-4-(4-methoxypheriyl)-6-(thiophen-2-yl)pyridin-2-yl)thio)(phenyl)methanesulfonamide, or a salt thereof,
   2-((3-cyano-4-(4-methoxyphenyl)-6-(thiophen-2-yl)pyridin-2-yl)thio)-N -(methylsulfonyl)-2-phenylacetamide, or a salt thereof,
   2-(((2,4-dioxothiazolidin-5-yl)(phenyl)methyl)thio)-4-(4-methoxyphenyl)-6-(thiophen-2-yl)nicotinonitrile, or a salt thereof,
   2-(((2,4-dioxooxazolidin-5-yl)(phenyl)methyl)thio)-4-(4-methoxyphenyl)-6-(thiophen-2-yl)nicotinonitrile, or a salt thereof,
   4-(4-methoxyphenyl)-2-(((5-oxo-4,5-dihydro-1,2,4-oxadiazol-3-yl)(phenyl)methyl)thio)-6-(thiophen-2-yl)nicotinonitrile, or a salt thereof,
   2-((2-hydroxy-1-phenylethypthio)-4-(4-methoxyphenyl)-6-(thiophen-2-yl)nicotinonitrile, or a salt thereof,
   2-((2-hydroxy-1-phenylethyl)thio)-4-(thiophen-2-yl)-5,6,7,8-tetrahydroquinoline-3-carbonitrile, or a salt thereof,
   methyl 2-((3-cyano-6-(thiophen-2-yl)-4-(trifluoromethyl)pyridin-2-yl)thio)-2-phenylacetate, or a salt thereof, and
   4-(furan-2-yl)-2-((2-hydroxy-1-phenylethyl)thio)-6-(thiophen-2-yl)nicotinonitrile, or a salt thereof.

2. The method of claim 1, wherein the method comprises administering the composition to a seed.

3. The method of claim 1, wherein the method comprises exogenously administering the composition to a plant.

4. The method of claim 3 wherein the composition is applied to the foliage of a plant.

5. The method of claim 3 wherein the method comprises applying the composition to the soil surrounding the root zone of a plant.

6. The method of claim 3 wherein the composition is applied directly to the base of the plants or to the soil immediately adjacent to the plants.

7. The method of claim 3 wherein the exogenous treatment composition is applied such that it drains through the soil to the root area of the plant.

8. The method of claim 3 wherein the composition is applied using a drench application, drip irrigation technique, or tilled into the soil or applied in furrow.

9. The method of claim 1 wherein the composition comprises an effective amount of 2-((3-cyano-4,6-di(thiophen-2-yl)pyridin-2-yl)thio)-2-phenylacetic acid or a salt thereof.

10. The method of claim 1 wherein the composition comprises an effective amount of 2-((4-(4-chlorophenyl)-3-cyano-6-(thiophen-2-yl)pyridin-2-yl)thio)-2-phenylacetic acid or a salt thereof.

11. The method of claim 1 wherein the composition comprises an effective amount of 2-((3-cyano-4,6-diphenylpyridin-2-yl)thio)-2-phenylacetic acid.

12. The method of claim 1 wherein the composition comprises an effective amount of 2-((3-cyano-4-(4-methoxyphenyl)-6-(thiophen-2-yl)pyridin-2-yl)thio)-2-phenylacetic acid.

13. The method of claim 1 wherein the composition comprises an effective amount of 2-((6-(4-bromophenyl)-3-cyano-4-(trifluoromethyl)pyridin-2-yl)thio)-2-phenylacetic acid.

14. A seed comprising a coating comprising a compound selected from the group consisting of:
- 2-((4-(4-chlorophenyt)-3-cyano-6-(thiophen-2-yl)pyridin-2-yl)thio)-2-phenylacetic acid, or a salt thereof,
- 2-((3-cyano-6-(thiophen-2-yl)-4-(trifluoromethyl)pyridin-2-yl)thio)-2-phenylacetic acid, or a salt thereof,
- 2-((3-cyano-4,6-di(thiophen-2-yl)pyridin-2-yl)thio)-2-phenylacetic acid, or a salt thereof,
- 2-((3-cyano-4-phenyl-6-(thiophen-2-yl)pyridin-2-yl)thio)-2-phenylacetic acid, or a salt thereof,
- 2-((3-cyano-4-(4-methoxyphenyl)-6-(thiophen-2-yl)pyridin-2-yl)thio)-2-phenylacetic acid, or a salt thereof,
- 2-((3-cyano-8-methyl-4-(thiophen-2-yl)-5,6,7,8-tetrahydro-1,8-naphthyridin-2-yl)thio)-2-phenylacetic acid,
- 2-((4-cyano-1-(thiophen-2-yl)-5,6,7,8-tetrahydroisoquinolin-3-yl)thio)-2-phenylacetic acid, or a salt thereof,
- 2-((3-cyano-6-(2,4-dimethoxyphenyl)-4-(trifluoromethyl)pyridin-2-yl)thio)-2-phenylacetic acid, or a salt thereof,
- 2-(3-cyano-6-(3,4-dimethoxyphenyl)-4-(trifluoromethyl)pyridin-2-yl)thio)-2-phenylacetic acid, or a salt thereof,
- 2-((6-(4-bromophenyl)-3-cyano-4-(trifluoromethyl)pyridin-2-yl)thio)-2-phenylacetic acid, or a salt thereof,
- 2-((3-cyano-6-(furan-2-yl)-4-(trifluoromethyl)pyridin-2-yl)thio)-2-phenylacetic acid, or a salt thereof,
- 2-((3-cyano-4,6-diphenylpyridin-2-yl)thio)-2-phenylacetic acid, or a salt thereof,
- 2-((3-cyano-4-(thiophen-2-yl)-5,6,7,8-tetrahydroquinolin-2-yl)thio)-2-phenylacetic acid, or a salt thereof,
- 2-((3-cyano-4-(4-methoxyphenyl)-6-thiophen-2-yl)pyridin-2-yl)thio-2-phenylacetic acid, or a salt thereof,
- 2-((4-cyano-1-ethyl-5,6,7,8-tetrahydroisoquinolin-3-yl)thio)-2-phenylacetic acid, or a salt thereof,
- 2-((3-cyano-6-methyl-4-(trifluoromethyl)pyridin-2-yl)thio)-2-phenylacetic acid, or a salt thereof,
- 2-((3-cyano-4-phenyl-5,6,7,8-tetrahydroquinolin-2-thio)-2-phenylacetic acid or a salt thereof,
- 2-((4-(4-chlorophenyl)-3-cyano-5,6,7,8-tetrahydronaphthalen-2-yl)thio)-2-phenylacetic acid, or a salt thereof,
- 2-((4-(4-methoxyphenyl)-6-(thiophen-2-yl)pyridin-2-yl)thio)-2-phenylacetic acid, or a salt thereof,
- 2-((3-cyano-6-(furan-2-yl)-4-(4-methoxyphenyl)pyridin-2-yl)thio)-2-phenylacetic acid, or a salt thereof,
- 2-((3-cyano-6-(thiophen-2-yl-4-(p-tolyl)pyridin-2-yl)thio)-2-phenylacetic acid, or a salt thereof,
- 2-((3-cyano-4-(4-fluorophenyl)-6-(thiophen-2-yl)pyridin-2-yl)thio)-2-phenylacetic acid, or a salt thereof,
- 2-((4-(4-bromophenyl)-3-cyano-6-(thiophen-2-yl)pyridin-2-yl)thio)-2-phenylacetic acid, or a salt thereof,
- 2-((3-cyano-6-(furan-2-yl)-4-(thiophen-2-yl)pyridin-2-yl)thio)-2-phenylacetic acid, or a salt thereof,
- 2-((3-cyano-4,6-di(furan-2-yl)pyridin-2-yl)thio)-2-phenylacetic acid, or a salt thereof,
- 2-((3-cyano-4-(4-methoxyphenyl)-5,6,7,8-tetrahydroquinolin-2-yl)thio-2-phenylacetic acid, or a salt thereof,
- 2-((3-cyano-4-(thiophen-2-yl)-5,6,7,8-tetrahydroquinolin-2-yl)oxy)-2-phenylacetic acid, or a salt thereof,
- 2-((3-cyano-4-(4-methoxyphenyl)-6-(1-oxidothiophen-2-yl)pyridin-2-yl)oxy)-2-phenylacetic acid, or a salt thereof,
- 2-((3-cyano-4-(4-methoxyphenyl)-6-(thiophen-2-yl)pyridin-2-yl)thio)butanoic acid, or a salt thereof,
- 2-((3-cyano-4-(4-methoxyphenyl)6-(pyrimidin-2-yl)pyridin-2-yl)thio)-2-phenylacetic acid, or a salt thereof,
- 2-((3-cyano-6-(3-methoxy-1-methyl-1H-pyrrol-2-yl)-4-4-methoxyphenyl)pyridin-2-yl)thio)-2-phenylacetic acid, or a salt thereof,
- 2-((3-cyano-4-(furan-2-yl)-6-(thiophen-2-yl)pyridin-2-yl)thio)-2-phenylacetic acid, or a salt thereof,
- 2-((3-cyano-4-(thiophen-2-yl)-5,6,7,8-tetrahydrouninolin-2-yl)thio)-2-phenylacetamide, or a salt thereof,
- 2((3-cyano-4-(4-methoxyphenyl)-6-(thiophen-2-yl)pyridin-2-yl)thio)-2-phenylacetamide, or a salt thereof,
- 2(((3-cyano-4-(4-methoxyphenyl)-6-(thiophen-2-yl)pyridin-2-yl)thio)-N-hydroxy-2-phenylacetamide, or a salt thereof,
- 4-(4-methoxyphenyl)-2-((phenyl(1H-tetrazol-5-yl)methyl)thio)-6-(thiophen-2-yl)nicotinonitrile, or a salt thereof,
- (((3-cyano-4-(4-methoxyphenyl)-6-(thiophen-2-yl)pyridin-2yl)thio)(phenyl)methyl)phosphonic acid, or a salt thereof,
- (((3-cyano-4-(4-methoxyphenyl)-6-(thiophen-2-yl)pyridin-2-yl)thio)(phenyl)methyl)phosphinic acid, or a salt thereof,
- ((3-cyano-4-(4-methoxyphenyl)-6-(thiophen-2-yl)pyridin-2-yl)thio)(phenyl)methanesulfonic acid, or a salt thereof,
- ((3-cyano-4-(4-methoxyphenyl)-6-(thiophen-2-yl)pyridin-2-yl)thio)(phenyl)methanesulfonamide, or a salt thereof,
- 2-((3-cyano-4-(4-methoxyphenyl)-6-(thiophen-2-yl)pyridin-2-yl)thio)-N -(methylsulfonyl)-2-phenylacetamide, or a salt thereof,
- 2-(((2,4-dioxothiazolidin-5-yl)(phenyl)methyl)thio)-4-(4-methoxyphenyl)-6-(thiophen-2-yl)nicotinonitrile, or a salt thereof,
- 2-(((2,4-dioxooxazolidin-5-yl)(phenyl)methyl)thio)-4-(4-methoxyphenyl-6-(thiophen-2-yl)nicotinonitrile, or a salt thereof, 4-(4-methoxyphenyl)-2-(((5-oxo-4,5-dihydro-1,2,4-oxadiazol-3-yl)(phenyl)methyl)thio)-6-(thiophen-2-yl)nicotinonitrile, or a salt thereof, 2-((2-hydroxy-1-phenylethyl)thio)-4-(4-methoxyphenyl)-6-(thiophen-2-yl)nicotinonitrile, or a salt thereof, 2-((2-hydroxy-1-phenylethyl)thio)-4-(thiophen-2-yl)-5,6,7,8-tetrahydroquinoline-3-carbonitrile, or a salt thereof, methyl 2-((3-cyano-6-(thiophen-2-yl)-4-(trifluoromethyl)pyridin-2-yl)thio)-2-phenylacetate, or a salt thereof, and 4-(furan-2-yl)-2-((2-hydroxy-1-phenylethyl)thio)-6-(thionhen-2yl)nicotinonitrile, or a salt thereof.

15. The seed of claim 14 wherein the coating comprises the compound in an amount of at least about 0.005 mg/seed.

16. The seed of claim 14 wherein the coating comprises the compound in an amount of from about 0.005 to about 1 mg/seed.

17. The seed of claim 14 wherein the coating comprises the compound 2((3-cyano-4,6-di(thiophen-2-yl)pyridin-2-yl)thio)-2-phenylacetic acid or a salt thereof.

18. The seed of claim 14 wherein the coating comprises the compound 2-((4-cyano-1-(thiophen-2-yl)-5,6,7,8-tetrahydroisoquinolin-3-yl)thio)-2-phenylacetic.

19. The seed of claim 14 wherein the coating comprises the compound 2-((3-cyano-4,6-diphenylpyridin-2-yl)thio)-2-phenylacetic acid.

20. The seed of claim 14 wherein the coating comprises the compound 2-((3-cyano-4-(4-methoxyphenyl)-6-(thiophen-2-yl)pyridin-2-yl)thio)-2-phenylacetic acid.

* * * * *